US007307541B2

(12) United States Patent
Ikeda et al.

(10) Patent No.: US 7,307,541 B2
(45) Date of Patent: Dec. 11, 2007

(54) LIGHT OUTPUT DEVICE, RELAY AND PROGRAM FOR CONTROLLING THE LIGHT OUTPUT DEVICE

(75) Inventors: Takumi Ikeda, Kobe (JP); Naoaki Yamamoto, Ota-ku (JP); Kazuhisa Watanabe, Yokohama (JP); Hiroshi Takase, Matsudo (JP); Tatsuo Yamamoto, Fujisawa (JP); Keiichi Koshiba, Miura-gun (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 219 days.

(21) Appl. No.: 10/506,886

(22) PCT Filed: Mar. 7, 2003

(86) PCT No.: PCT/JP03/02714

§ 371 (c)(1),
(2), (4) Date: Apr. 27, 2005

(87) PCT Pub. No.: WO03/077216

PCT Pub. Date: Sep. 18, 2003

(65) Prior Publication Data
US 2005/0200452 A1   Sep. 15, 2005

(30) Foreign Application Priority Data
Mar. 8, 2002   (JP) .............................. 2002-062954

(51) Int. Cl.
*G08B 5/00* (2006.01)
(52) U.S. Cl. .................. 340/815.4; 340/321; 340/540; 340/573.1; 340/693.5; 340/815.45; 340/815.65; 398/126

(58) Field of Classification Search ............. 340/815.4, 340/815.45, 815.65, 573.1, 691.6, 521, 531, 340/540, 693.5, 665, 539.11–539.13, 539.16–539.17, 340/539.2, 539.22, 321, 326, 331, 332; 600/587, 600/300; 128/903; 455/67.7
See application file for complete search history.

(56) References Cited

U.S. PATENT DOCUMENTS 4,611,198 A * 9/1986 Levinson et al. ...... 340/539.11

(Continued)

FOREIGN PATENT DOCUMENTS

EP   0 770 349   5/1997

(Continued)

OTHER PUBLICATIONS

International Search Report corresponding to application No. PCT/JP03/02714 dated Jun. 24, 2003.

(Continued)

*Primary Examiner*—Thomas Mullen
(74) *Attorney, Agent, or Firm*—RatnerPrestia

(57) ABSTRACT

An information processing system formed with a relay and light output devices. In the system, an external information receiver receives first external information transmitted from an outside. An external information acquisition unit acquires second external information. A light output controller controls, based on the first and second external information, the light output to be in one or more number of output states, among three or more number of output states. At the relay, an external information receiver receives a sender identifier for identifying sender of the external information, and the external information. A transmission control information memory stores one or more sets of a transmission destination identifier and transmission control information. A transmission destination identifier acquisition unit acquires transmission destination identifier from the transmission control information memory. An external information transmitter transmits external information to a destination identified by the transmission destination identifier.

53 Claims, 45 Drawing Sheets

U.S. PATENT DOCUMENTS

| | | | |
|---|---|---|---|
| 4,978,946 A * | 12/1990 | Nordholm et al. | 340/573.1 |
| 5,652,570 A | 7/1997 | Lepkofker | |
| 5,905,442 A | 5/1999 | Mosebrook et al. | |
| 6,611,297 B1 * | 8/2003 | Akashi et al. | 348/739 |
| 6,998,984 B1 * | 2/2006 | Zittrain et al. | 340/573.1 |
| 2002/0145522 A1 * | 10/2002 | Pembroke | 340/573.1 |

FOREIGN PATENT DOCUMENTS

| | | |
|---|---|---|
| EP | 0 875 821 | 11/1998 |
| JP | 59-187883 | 12/1984 |
| JP | 1-70389 | 5/1989 |
| JP | 5-233980 | 9/1993 |
| JP | 5-265387 | 10/1993 |
| JP | 6-23339 | 3/1994 |
| JP | 08-077463 | 3/1996 |
| JP | 08-106349 | 4/1996 |
| JP | 2000-173783 | 6/2000 |
| JP | 2001-160849 | 6/2001 |
| JP | 2001-210114 | 8/2001 |
| JP | 2001-222317 | 8/2001 |
| JP | 2001-344675 | 12/2001 |

OTHER PUBLICATIONS

European Office Action Dated Apr. 19, 2006.

\* cited by examiner

| Voltage | Own pressure information(n) | Other's pressure information (m) |
|---|---|---|
| 0 | 0 | — |
|  | — | 0 |
| min(n,m) | 1~9 | — |
|  | — | 1~9 |
| n+m but,max30 | Not less than 10 | Not less than 10 |

FIG. 8

| Light control parameter | ON/OFF pattern |
|---|---|
| 0 | ON ──────────<br>OFF ━━━━━━━━━━ |
| 1 | ON ─── 9 ┌1┐ 9 ┌1┐ 9 ┌1┐<br>OFF ━━━━┛ ┗━━━━┛ ┗━━━━┛ ┗ |
| 2 | ON ── 8 ┌2─┐ 8 ┌2─┐ 8 ┌2─┐<br>OFF ━━━┛  ┗━━┛  ┗━━┛  ┗ |
| 3 | ON ─ 7 ┌─3─┐ 7 ┌─3─┐ 7 ┌─3─┐<br>OFF ━━┛   ┗━┛   ┗━┛   ┗ |
| ⋮ |  |
| 9 | ON ──┐1┌──┐1┌──┐1┌<br>　　9 │ │9 │ │9 │ │<br>OFF   ┗┛  ┗┛  ┗┛ |
| Not less than 10 | ON ━━━━━━━━━━<br>OFF ────────── |

Pressure information

| Value of sensor 1 | Value of sensor 2 | ...... | Value of sensor 6 |
|---|---|---|---|
| | | | |

| Pressure information | 0 | 0 | 20 | 5 | 5 | 20 |
|---|---|---|---|---|---|---|

| | X(Latitude) | Y(Longitude) | Z(altitude) |
|---|---|---|---|
| Location information | 136 | 110 | 5 |

FIG. 20

| Type information | ID | value information |
|---|---|---|
| Location information | 2 | (136,110,5) |
| Pressure information | 1 | 12.5 |

FIG. 21

| Type information | ID | value information |
|---|---|---|
| Pressure information | 1 | 5 |
| Location information | 2 | (136,109,0) |

FIG. 22

| Voltage | Distance between two devices (km) |
|---|---|
| 20 | 0~1 |
| 15 | 1.1~5 |
| 10 | 5.1~10 |
| 5 | 10.1~20 |
| 0 | 20.1~ |

FIG. 27

| Light output unit identifier | Type information | Light output method identifier |
|---|---|---|
| First light output unit | Pressure information | Light ON/OFF |
| Second light output unit | Position information | Light rotation |

FIG. 28

| Light output method identifier |
|---|
| Light intensity |
| Light color |
| Light ON/OFF |
| Light rotation |
| Light source size |

FIG. 29

| Type information · light output method identifier setting panel |||
|---|---|---|
| Input type information and/or light output method identifier |||
| Light output unit | Type information | Light output method identifier |
| First light output unit | Pressure information | Light ON/OFF |
| Second light output unit | Location information | Menu |
| | | Light intensity |
| | | Light color |
| | | Light ON/OFF |
| | | Light rotation |
| | | Light source size |

Enter

FIG. 35

| Time | External information from first light output device | External information from second light output device |
|---|---|---|
| 9:00 | 134 | 133 |
| 9:05 | 190 | 180 |
| 9:10 | 480 | 70 |
| ⋮ | ⋮ | ⋮ |

FIG. 36

| Difference of two sets of external information | Light control parameter |
|---|---|
| Not less than 200 | 0 |
| 100~199 | 5 |
| 50~99 | 10 |
| 10~49 | 15 |
| 0~9 | 20 |

Left  3701 3702 3703  Right

FIG. 45
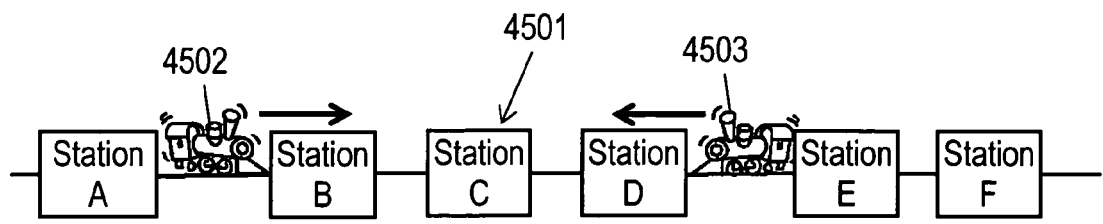
FIG. 46
| Station identifier | Station A | Station B | Station C | Station D | Station E | Station F |
|---|---|---|---|---|---|---|
| Distance | 0 | 5.2km | 8.4km | 10.3km | 15.0km | 21.3km |
4601
FIG. 47
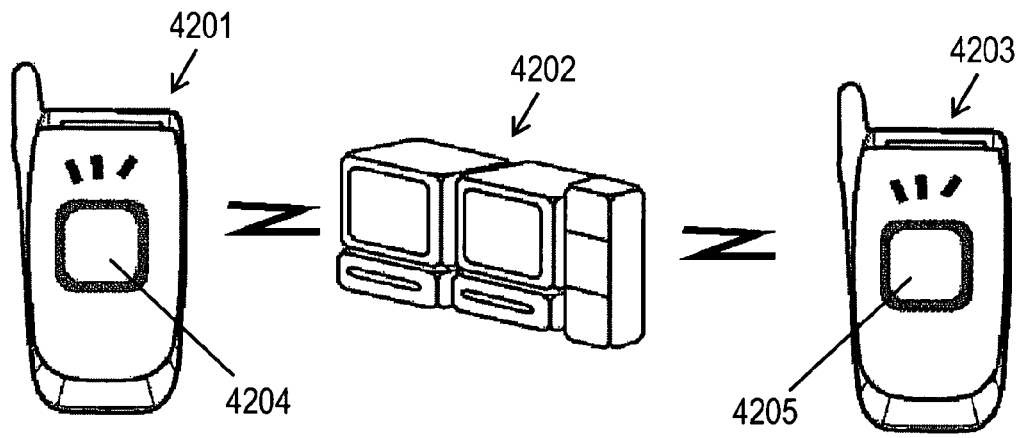

| Point | Heart beat | Blood temperature | Blood sugar | Blood pressure | |
|---|---|---|---|---|---|
| 0 | 91~ | 40.1~ | 151~ | High ( Not less than 180 / Not more than 70 ) | |
| | | | | Low ( 130~140 / 30~40 ) | |
| 5 | 81~90 | 39.1~40.0 | 141~150 | High ( 170~180 / 70~80 ) | |
| | | | | Low ( 120~130 / 40~50 ) | |
| 10 | 71~80 | 38.1~39.0 | 131~140 | High ( 160~170 / 80~90 ) | |
| | | | | Low ( 110~120 / 40~50 ) | |
| 15 | 61~70 | ~35.9 / 37.3~38.0 | 121~130 | High ( 150~160 / 90~100 ) | |
| | | | | Low ( 100~110 / 50~60 ) | |
| 20 | 51~60 | 36.0~36.2 / 36.9~37.2 | 111~120 | High ( 140~150 / 100~110 ) | |
| | | | | Low ( 90~100 / 60~70 ) | |
| 25 | ~50 | 36.3~36.8 | ~110 | High 110~140 | |
| | | | | Low 70~90 | |

FIG. 52

| First external information 5201 | | Second external information 5202 | |
|---|---:|---|---:|
| <Heart beat pulse information> | 78 | <Heart beat pulse information> | 50 |
| <Blood temperature information> | 36.5 | <Blood temperature information> | 35.5 |
| <Blood sugar information> | 80 | <Blood sugar information> | 140 |
| <Blood pressure information> | 133.70 | <Blood pressure information> | 150,105 |
| <Health condition information> | 85 | <Health condition information> | 65 |

FIG. 55

| Parameter | First light output device | Second light output device |
|---|---|---|
| 0 | NO | NO |
| 1 | YES | YES |
| 1 | NO | YES |
| 5 | YES | YES |

LIGHT OUTPUT DEVICE, RELAY AND PROGRAM FOR CONTROLLING THE LIGHT OUTPUT DEVICE

This application is a U.S. national phase application of PCT international application PCT/JP03/02714.

TECHNICAL FIELD

The present invention relates to an information processing system consisting of a light output device, a relay and a program for controlling the light output device. Users of the information processing system can softly communicate their general conditions, sentiments, etc. among each other by means of a light output.

BACKGROUND ART

Portable telephones, computers connected via the internet, etc. are the popular communication tools between one person and other person.

The internet and the broadband networks have now become handy communication means readily available anywhere; the transmission/reception of information can be made through a network connected around-the-clock.

With the above-described conventional communication technologies, however, it is impossible for one person to get an obscure general knowledge about the present conditions, sentiments or affections of his, or her, specific partner (e.g. a sweetheart, a family member) in a soft obscure manner; also, it is impossible to communicate his, or her, present conditions, sentiments or affections to the partner in a soft obscure mood. The expressions, "getting an obscure general knowledge in a soft manner" and "communicating conditions, sentiments or affections in a soft obscure mood" do not mean, for example, to be informed about the busy status through a telephone conversation, or letting a partner understand how he, or she, is busy concentrating on an assignment, through an e-mail via the internet. However, these expressions mean, for example, to let the partner recognize his, or her, strong wishes to meeting the partner immediately, or to confirm that his, or her, strong love affections are towards the partner.

Portable telephones and e-mails, on the other hand, can carry out an active communication on a certain specific status of affairs; but in this case, the act of communicating with respect to the status of affairs can not help remaining as the main point of interest among the communicating parties.

DISCLOSURE OF INVENTION

An information processing system in the present invention has a first light output device, a relay and a second light output device. Each of the light output devices includes an external information receiver, an external information acquisition unit, a light output unit and a light output controller.

The external information acquisition unit receives the first external information, which is external information of an outside. The external information acquisition unit receives second external information, which is another external information of the other outside. The light output unit outputs a light. The light output controller controls the light output unit in multi-stages when outputting the light based on the first external information and the second external information, so that the light output unit outputs the light in one or more number of output states from among three or more number of output states.

In the present DESCRIPTION, the first light output device and the second light output device, respectively, are sometimes referred to simply as a light output device, because the two light output devices have the same structure.

The relay includes an external information receiver, a transmission control information memory, a transmission destination identifier acquisition unit and an external information transmitter. The external information receiver receives a sender identifier for identifying a sender of external information and external information. The transmission control information memory stores one or more sets of transmission control information consisting of a transmission destination identifier for identifying destination of transmission and a sender identifier. The transmission destination identifier acquisition unit acquires, from the transmission control information memory, a transmission destination identifier, which is a counterpart of the sender identifier contained in the external information received at the external information receiver. The external information transmitter sends the external information received at the external information receiver to a transmission destination identified by the transmission destination identifier acquired at the transmission destination identifier acquisition unit.

Another information processing system may be formed with a first light output device and a second light output device, with the relay eliminated. In this system, the external information are transmitted/received directly between the first and the second light output devices, and the light output devices output the light based on two pieces of external information.

Furthermore, still another information processing system may be formed in the following configuration: The information processing system is formed with a first light output device, a relay and a second light output device. The relay includes an external information receiver, a light control parameter determination unit and a parameter transmitter. The external information receiver receives a plurality of external information delivered from a plurality of external origins. The light control parameter determination unit determines a light control parameter based on a plurality of external information. The parameter transmitter transmits a light control parameter determined by the light control parameter determination unit to the light output device. The light output devices output the light based on a light control parameter transmitted from the relay.

BRIEF DESCRIPTION OF THE DRAWINGS

FIG. 8 shows an example of light output control information in the first embodiment.

FIG. 20 shows an example of external information in the third embodiment.

FIG. 21 shows an example of external information in the third embodiment.

FIG. 22 is a table used for determining a light control parameter in the third embodiment.

FIG. 27 shows a light output control table in the fourth embodiment.

FIG. 28 shows data constituting a menu for selecting a light output control method identifier in the fourth embodiment.

FIG. 29 illustrates a panel used for designating a type information light output method identifier in the fourth embodiment.

FIG. 35 shows exemplary history information in the fifth embodiment.

FIG. 36 shows a table for determining a light control parameter in the fifth embodiment.

FIG. 45 shows an application example of a light output device in the seventh embodiment.

FIG. 46 shows a distance control table in the seventh embodiment.

FIG. 47 illustrates the concept of an information processing system in the seventh embodiment.

FIG. 52 shows an example of external information in the eighth embodiment.

FIG. 55 shows a table for determining a light control parameter in the ninth embodiment.

BEST MODES FOR CARRYING OUT THE INVENTION

Embodiment 1

Figure 1:
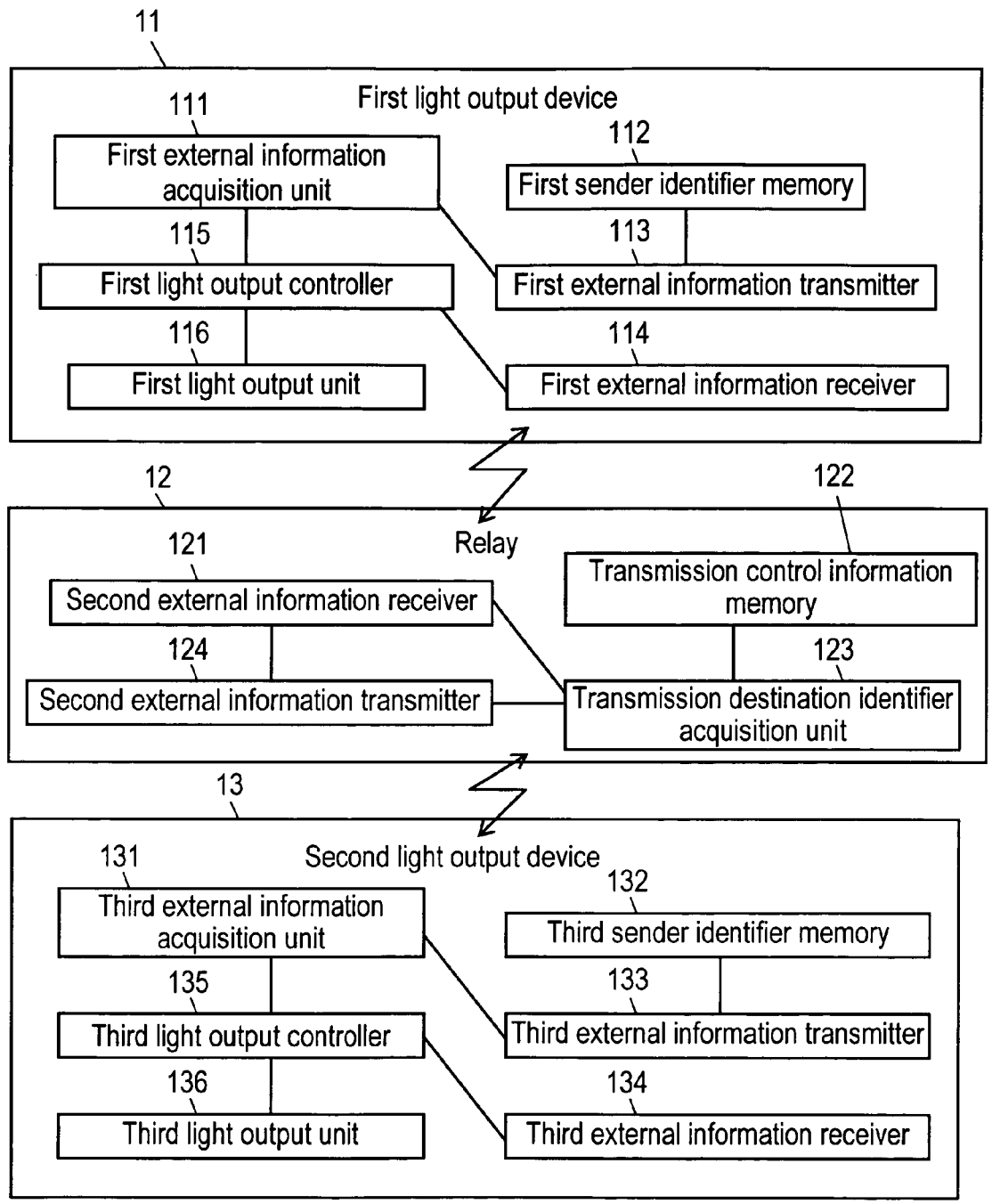
FIG. 1 is a block diagram of an information processing system in accordance with a first exemplary embodiment of the present invention.

FIG. 1 is a block diagram of an information processing system in accordance with the present embodiment.

The present information processing system includes first light output device 11, relay 12 and second light output device 13. First light output device 11 and second light output device 13, respectively, acquire external information, which external information indicating the conditions of respective users holding the devices. And the external information is transmitted to each other.

First light output device 11 and second light output device 13 output the light based on the external information received from the partner and the external information that each of the devices acquires itself. Relay 12 receives external information delivered from first light output device 11, and transmits the external information to second light output device 13.

Relay 12 receives the external information delivered from second light output device 13, and transmits the external information to first light output device 11.

First light output device 11 includes first external information acquisition unit 111, first sender identifier memory 112, first external information transmitter 113, first external information receiver 114, first light output controller 115 and first light output unit 116.

First external information acquisition unit 111 acquires first external information, which is information about the condition of first light output device 11's user. The external information can be any information, in so far as it bears something related with the condition of a person who uses the device.

Examples of the external information include such information as follows:

Speed of typing on a keyboard (an indication of how busy the user is);

Location information indicating where a (terminal) holder is;

Place information indicating where a (terminal) holder is in;

Pressure information indicating how strongly a terminal is grasped;

Pulse count information, body temperature information of a user;

Information indicating how strongly a terminal is shaken.

First external information acquisition unit 111 is structured in different configurations, depending on the nature of the external information above. This point will be detailed in embodiment 2, and thereafter.

First sender identifier memory 112 stores a first sender identifier, which is information for identifying first light output device 11. First sender identifier memory 112 can be implemented with a semiconductor memory, a hard disk, a CD-ROM or the like memory media. Normally, a non-volatile memory is used; but a volatile memory can be used instead. Any information can be the first sender identifier, in so far as it identifies a sender; for example, an IP address attached to the present first light output device 11 can be used. When the technology of IP Ver. 6 becomes widespread, many apparatus will have their own IP address, and they will be able to communicate with each other. Mail address and so on of a user of first light output device 11 can also be used for the sender identifier. In a case where first light output device 11 is a portable telephone unit, the telephone number may be used for the sender identifier.

First external information transmitter 113 transmits the first external information acquired by first external information acquisition unit 111 and a first sender identifier stored in first sender identifier memory 112.

First external information receiver 114 receives the second external information delivered from second light output device 13 via relay 12. The second external information is the external information acquired at second light output device 13.

First external information transmitter 113 and first external information receiver 114 can be implemented with a communication apparatus. A broadcasting apparatus may be used instead. The communication apparatus may either be a wireless apparatus or a wired apparatus; a suitable type of apparatus may be selected depending on the external information to be transmitted.

First light output controller 115 controls first light output unit 116 based on the first external information and the second external information. The control of light output here is a multi-level control; where, first light output unit 116 is instructed to output the light in one or more light output states, among three or more light output states (including OFF state). First light output controller 115 is normally implemented with software, but a dedicated circuit (hardware) may be used instead.

First light output unit 116 outputs light in accordance with the control by first light output controller 115. Any light-emitting media, such as an LED, a miniature lamp, an LCD display, a CRT, etc. may be used for first light output unit 116. However, first light output unit 116 needs to be capable of outputting the light in at least three states, including OFF state; namely, it has to be capable of outputting the light in multi-level states (at two or more levels). In other words, those light output media having only ON and OFF states can not be used for first light output unit 116.

Relay 12 includes second external information receiver 121, transmission control information memory 122 and transmission destination identifier acquisition unit 123 and second external information transmitter 124.

Second external information receiver 121 receives the external information (the first external information or the second external information) and a sender identifier which identifies a sender of the external information. Second external information receiver 121 can be implemented normally with a wireless, or wired, communication apparatus. An apparatus for receiving broadcasting may be used instead for the purpose.

Transmission control information memory 122 stores transmission control information, which is formed as a set of transmission destination identifier for identifying a transmitting destination of the external information and a sender identifier, for one or more number of sets. Normally, transmission control information memory 122 is formed of a non-volatile memory such as a hard disk, but a volatile memory may be used instead. The transmission destination identifier and the sender identifier do not always correspond in 1-to-1 relationship, but they can be in n-to-1, 1-to-n or n-to-n relationships.

Transmission destination identifier acquisition unit 123 acquires from transmission control information memory 122 one or more transmission destination identifiers, which will be the counterpart of the sender identifier received at second external information receiver 121. Normally transmission destination identifier acquisition unit 123 is implemented with software, but a dedicated circuit (hardware) may be used instead.

Second external information transmitter 124 transmits the external information received at second external information receiver 121 to a destination identified by a transmission destination identifier acquired by transmission destination identifier acquisition unit 123. Second external information transmitter 124 can be implemented with a wireless, or wired, communication apparatus (e.g. a modem and the driver software, etc.), but a broadcasting apparatus may be used instead.

Second light output device 13 includes third external information acquisition unit 131, third sender identifier memory 132, third external information transmitter 133, third external information receiver 134, third light output controller 135 and third light output unit 136.

Third external information acquisition unit 131, third sender identifier memory 132, third external information transmitter 133, third external information receiver 134, third light output controller 135 and third light output unit 136, of second light output device 13 perform, respectively, identical functions as those of first external information acquisition unit 111, first sender identifier memory 112, first external information transmitter 113, first external information receiver 114, first light output controller 115 and first light output unit 116, of first light output device 11.

Therefore, following portions of the system will sometimes be referred to as follows:

First external information acquisition unit and third external information acquisition unit, referred to as external information acquisition unit;

First sender identifier memory and third sender identifier memory, as sender identifier memory;

First external information transmitter and third external information transmitter, as external information transmitter;

First external information receiver and third external information receiver, as an external information receiver;

First light output controller and third light output controller, as light output controller; and First light output unit and third light output unit, as light output unit.

Third external information acquisition unit 131 acquires the second external information. Third external information acquisition unit 131 performs the identical function as that of first external information acquisition unit 111.

Third sender identifier memory 132 stores a second sender identifier which is an information for identifying second light output device 13. Third sender identifier memory 132 is implemented with a semiconductor memory, a hard disk, a CD-ROM or the like memory media. Normally, a non-volatile memory is used, but a volatile memory may be used instead. Any information that can identify a sender may be used for the sender identifier; for example, an IP address attached to the present second light output device 13 may be used. When the technology of IP Ver. 6 becomes wide-spread, many apparatus will have their IP address, and they will be able to communicate with each other. Mail address and so on of a user of first light output device 11 may be used for the sender identifier. In a case where second light output device 13 is a portable telephone unit, the telephone number may be used for the sender identifier.

Third external information transmitter 133 transmits the second external information acquired by third external information acquisition unit 131 and a second sender identifier stored in third sender identifier memory 132.

Third external information receiver 134 receives the first external information delivered from first light output device 11 via relay 12. The first external information is that which is acquired at first light output device 11.

Third external information transmitter 133 and third external information receiver 134 can be implemented with communication apparatus. A broadcasting apparatus may be used instead. Either a wireless communication apparatus or a wired communication apparatus may be used for the communication apparatus; a suitable type of the apparatus may be selected depending on the external information to be transmitted.

Third light output controller 135 controls third light output unit 136 based on the first external information and the second external information. The control of light output here is a multi-level control; where, third light output unit 136 is instructed to output the light in one or more light output states, among three or more light output states (including OFF state). Third light output controller 135 is normally implemented with software for controlling third light output unit 136, but hardware may be used instead.

Third light output unit 136 outputs light. Any light-emitting media, such as an LED, a miniature lamp, an LCD display, a CRT, etc. may be used. However, third light output unit 136 needs to be capable of outputting the light in at least three states, including OFF state; namely, it has to be capable of outputting the light in multi-level states (at two or more levels). In other words, those light output media having only ON and OFF states can not be used for third light output unit 136.

As described in the above, first light output device 11 and second light output device 13 have the same structure.

Next, operation of the present information processing system is described. In the first place, operation of first light output device 11 is described referring to FIG. 2, a flow chart.

(Step S201) First external information acquisition unit 111 judges if an instruction to start acquiring external information is received, or not. If such instruction is received; then, it proceeds to S202. If no such instruction is received; then, it repeats S201. The starting instruction can be interpreted as an instruction to start acquiring external information; at the same time, it can be understood as an instruction to start the entire processing of FIG. 2.

(Step S202) First external information acquisition unit 111 acquires external information of its own side (first external information).

(Step S203) First external information transmitter 113 acquires a sender identifier from first sender identifier memory 112.

(Step S204) First external information transmitter 113 acquires a relay identifier, which is an information for identifying a relay. The relay identifier is stored in advance in a memory not shown in the drawing. The relay identifier is information needed for communicating with a relay, e.g. an IP address of a relay.

(Step S205) First external information transmitter 113 transmits the external information of its own side and the sender identifier to a relay identified by the relay identifier.

(Step S206) First external information receiver 114 judges if an external information of the other side (second external information) is received, or not. If received, it proceeds to S207; if not received, it returns to S206.

(Step S207) First light output controller determines a control parameter for controlling the light output based on the own external information acquired at S202 and an external information of the other side received at S206.

(Step S208) First light output unit 116 outputs the light in accordance with the control parameter determined at S207.

(Step S209) First light output device 11 judges if a finish signal is received, or not. If yes, the procedure is finished; if not received, it returns to S201.

Figure 2:
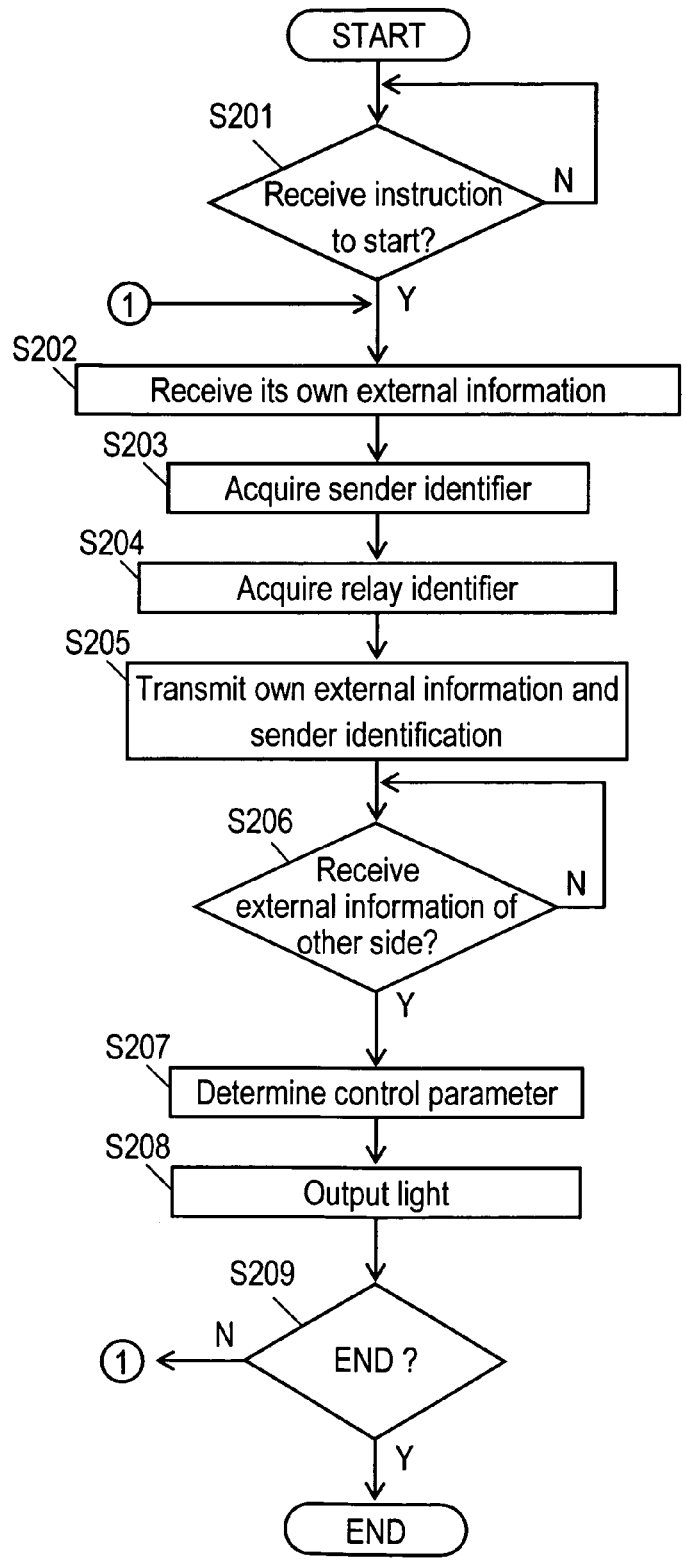
FIG. 2 is a flow chart used to describe the operation of a light output device in the first embodiment.

In the flow chart, FIG. 2, the acquisition of external information is triggered by reception of a starting instruction. In a practical case, a starting instruction is generated by a user pressing a start button (not shown). The starting instruction can be generated also by second light output device 13, relay 12 or other devices. However, the operation shown in the flow chart, FIG. 2, may be started without having any triggering.

Figure 3:
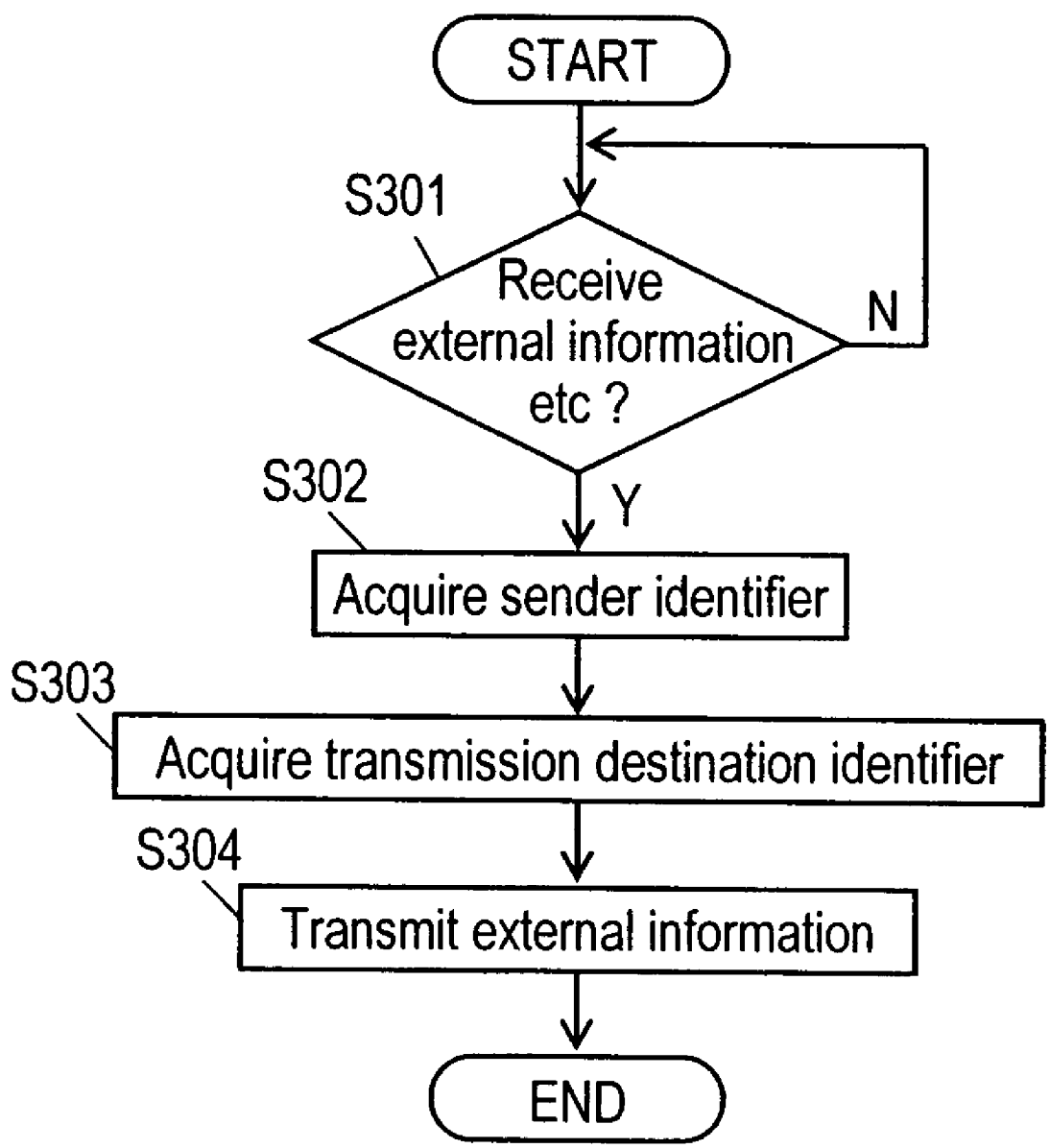
FIG. 3 is a flow chart used to describe the operation of a relay in the first embodiment.

Operation of relay 12 is described referring to a flow chart shown in FIG. 3.

(Step S301) Second external information receiver 121 judges if external information and a sender identifier are received from first light output device 11 or second light output device 13. If external information and sender identifier are received, it proceeds to S302; if not received, it repeats S301.

(Step S302) Transmission destination first identifier acquisition unit 123 acquires a sender identifier out of the information received at second external information receiver 121.

(Step S303) Transmission destination identifier acquisition unit 123 acquires from transmission control information memory 122 all of the transmission destination identifiers which correspond to the sender identifier acquired at step 302. The transmission destination identifier may be a single piece of information, or in pluralities.

(Step S304) Second external information transmitter 124 transmits the external information received at S301 to a transmission destination identified by the transmission destination identifier acquired at S303. The external information may be sent either together with a sender identifier, or the external information alone.

In the flow chart, FIG. 3, the relay transmits the external information after being triggered by the reception of the external information. The external information, however, may be transmitted when an access demand is raised from second light output device 13 or first light output device 11.

Operation of second light output device 13 remains the same as that of first light output device 11. Therefore, the description on device 13 is eliminated.

Now in the following, the practical operation of the information processing system in the present embodiment and the shape of light output devices constituting the system are described.

Figures 4, 5:
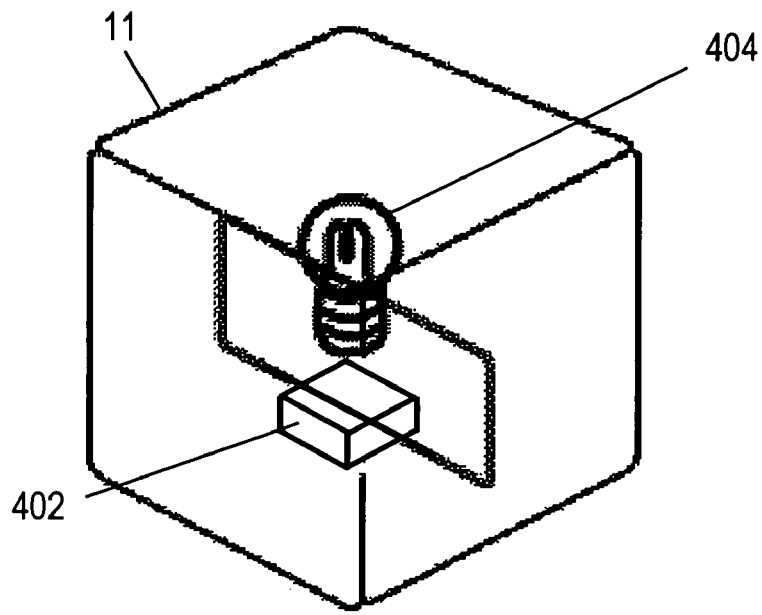
FIG. 4 shows the appearance of a light output device in the first embodiment.
FIG. 5 is a table held by a light output controller in the first embodiment.

Suppose first light output device 11 and second light output device 13 have exactly the same configuration, and they are shaped, for example, in a cube form as illustrated in FIG. 4.

Light output device 11 includes light output unit 404 and voltage control unit 402 for controlling the light output in voltage. Each of the light output devices is provided with a pressure sensor in the six faces. When each of the light output devices is grasped, the pressure information indicating the grasping force is acquired by each of the devices at the external information acquisition unit. The respective external information is transmitted via the relay to the other device. Namely, in the present example, the external information acquired by respective light output devices to be transmitted to the other side includes the pressure information; and the external information acquisition unit works as the pressure information acquisition unit.

Each of the light output devices determines a light control parameter based on the own pressure information and the pressure information delivered from the other side. FIG. 5 shows a table used when respective light output controllers determine a light control parameter.

Table in FIG. 5 has such property items as "Voltage", "Own pressure information (n)" and "Other's pressure information (m)". "Voltage" means a voltage for outputting the light. The higher the voltage, the brighter are the light output units. According to FIG. 5, "Voltage" is "0" when either one of the own pressure information and the other's pressure information is "0". This means that the light output unit does not respond unless both of the first light output device and the second light output device are pressurized. Namely, there will be no light output. In a case where the own pressure information or the other's pressure information is "1 to 9", the smaller value of the own pressure information and the other's pressure information makes the "Voltage" value. This is shown as "min (n, m)"; where, "n" is representing the own pressure information while "m" is representing the other's. When the own pressure information and the other's pressure information are higher than 10, "Voltage" becomes to be "n+m (max. 30)".

As described in the above, when respective light output devices are firmly grasped by the respective holders, they generate intense lights; whereas, no light is generated if either one of the devices is not grasped.

Figure 6:
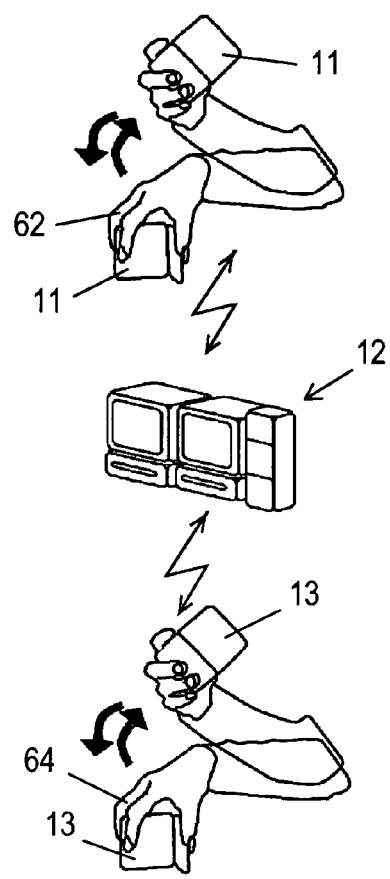
FIG. 6 illustrates the concept of an information processing system in the first embodiment.

FIG. 6 illustrates a practical example. Respective light output devices 11 and 13 are firmly grasped by the hands 62 and 64, and both of the devices are outputting intense lights.

Respective light output devices are provided at each of the faces (6 faces) with a pressure sensor. When the devices are grasped by the user, the pressure values detected by the pressure sensor at the 6 faces are acquired by respective external information acquisition units. Each of the external information transmitters transmits the external information to other's light output device via relay 12. At this stage, respective external information transmitters may transmit the external information acquired at respective external information acquisition units after it is processed. Since the transmitting information is that which has been processed on the basis of the acquired external information, it is referred to as external information. The other light output device outputs light based on the external information received from the other's device and own external information acquired by itself. Referring to FIG. 5 and FIG. 6, a voltage controller controls the voltage based on the pressure information.

Light output controller of respective light output devices controls the light output in multi-levels, based on the relationship among "external information received", "own external information" and "voltage".

Thus in the present embodiment, external information indicating the conditions of respective users of light output devices are transmitted via a relay to the other light output device. Respective light output devices output the information in the form of light output implicating the users' conditions with an obscure and soft mood.

Suppose, lovers each bearing the present light output device with them, for example, firmly grasp their own device with a strong desire for meeting together; then, each of the devices will be brilliantly lit. The lovers would feel happy when each of the couple is convinced that his, or her, partner is keeping a strong love affection to the other.

In the present embodiment, and in all of the following embodiments, a relay is not an essential item. The first light output device and the second light output device may transmit/receive external information to each other directly.

In the present embodiment, respective light output devices and a relay transmit/receive a sender identifier, and the relay acquires a transmission destination identifier from the received sender identifier. Such relay is referred to as first relay.

Instead, transmission destination identifier may be transmitted from respective light output devices to a relay. Furthermore, the relay may be structured in the following configuration:

In the relay, second external information receiver receives a transmission destination identifier for identifying the destination of an external information and the external information. Second external information transmitter transmits an external information received at second external information receiver to a destination identified by a transmission destination identification information contained in the external information received at second external information receiver.

Second external information transmitter may transmit an external information automatically, or upon an access request from light output device for external information. Such a relay is referred to as second relay.

In the present embodiment, respective light output devices determine a light control parameter based on the first external information and the second external information. A relay may determine the light control parameter based on the first external information and the second external information. Such a relay is referred to as third relay, which will be detailed in embodiment 2.

The relay can be in the above three types. This applies likewise in all of the embodiments in the present description.

In the present embodiment, a light control parameter is determined by respective light output devices. However, the parameter may be determined instead by a relay; this will be described in embodiment 2. In the latter case, a light control parameter determined by a relay is transmitted to each of the light output devices, and the light output devices output the light in accordance with the light control parameter. This applies likewise also in the other embodiments.

Figure 7:
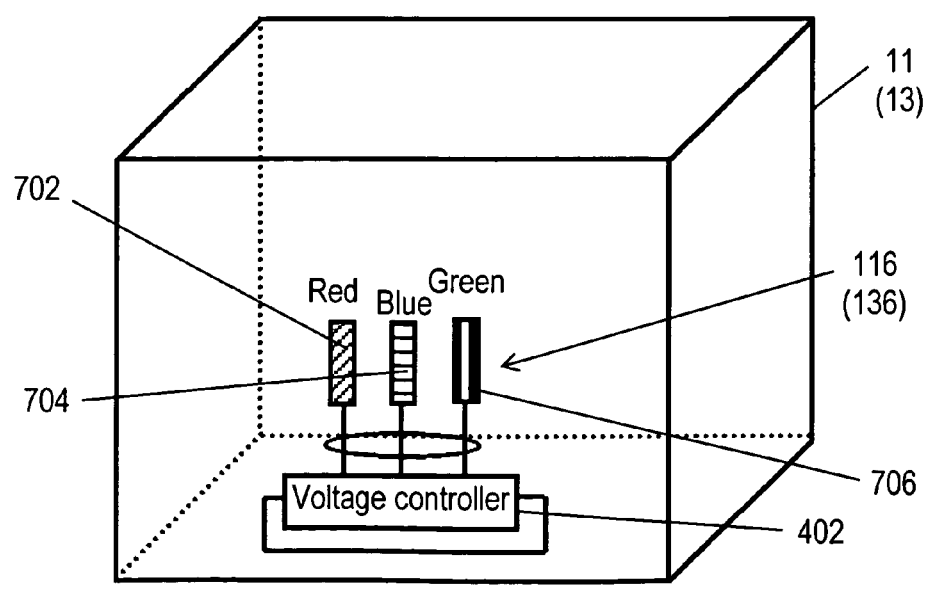
FIG. 7 shows an example of light outputting in the first embodiment.

In the present embodiment, respective light output controllers control the light intensity based on the light control parameter. However, the light may be controlled by other methods. Examples of the other methods of controlling the light include the following:

Respective light output controllers may instruct, based on light control parameter, to output one color among three or more colors. Suppose there are three LEDs, 702, 704 and 706, constituting the light source for "red", "blue" and "green" in light output unit 116, or 136, as shown in FIG. 7. Light output controller 135 determines the voltages, based on an external information received at third external information receiver 134, to be applied by voltage controller 402 on the three LEDs, R 702, B 704 and G 706; or, the intensity of three colors. Thus color of the light output can be controlled by controlling the light intensity of the three LEDs.

Other exemplary method of control is outputting the light in one of the three, or more, ON/OFF patterns. For example, light output controller keeps information on "Light control parameter" and "ON/OFF pattern", as shown in FIG. 8, under its control. An ON/OFF pattern for a miniature lamp is determined based on the light control parameter.

Figure 9:
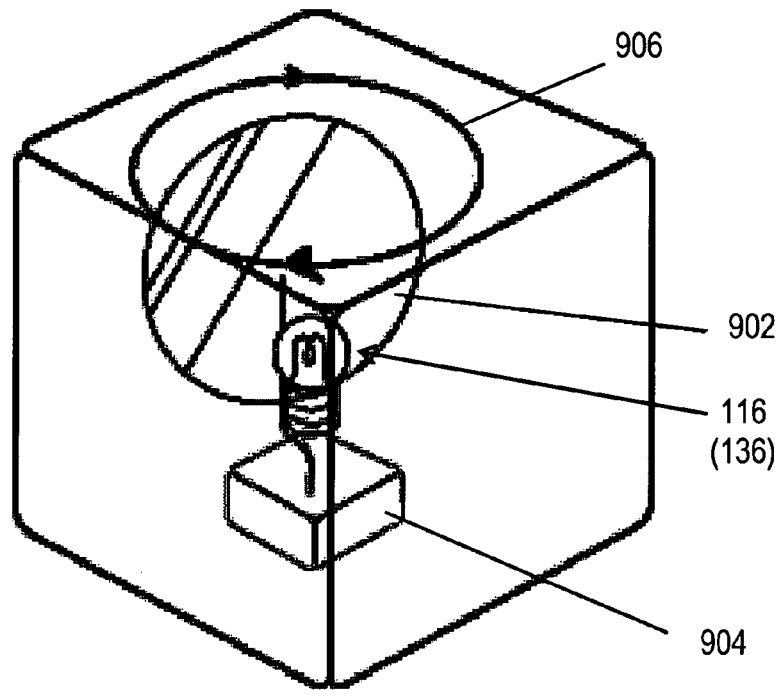
FIG. 9 shows an example of light outputting in the first embodiment.

Still other exemplary method of control is outputting the light in one of the three, or more, revolving modes. A practical structure is as follows:

As shown in FIG. 9, light output unit, 116 or 136, is provided at its side with rotating reflector 902. Reflector 902 is rotated by drive gear 904, e.g. a motor, in direction 906. The pattern of rotation and the speed of rotation, etc. of reflector 902 are determined based on external information received. A value of rotation speed, for example, is received as the external information, and the value is used for driving reflector 902.

Still other exemplary method of control is outputting the light at one of the three, or more, light source sizes. A practical structure is as follows.

Figure 10:
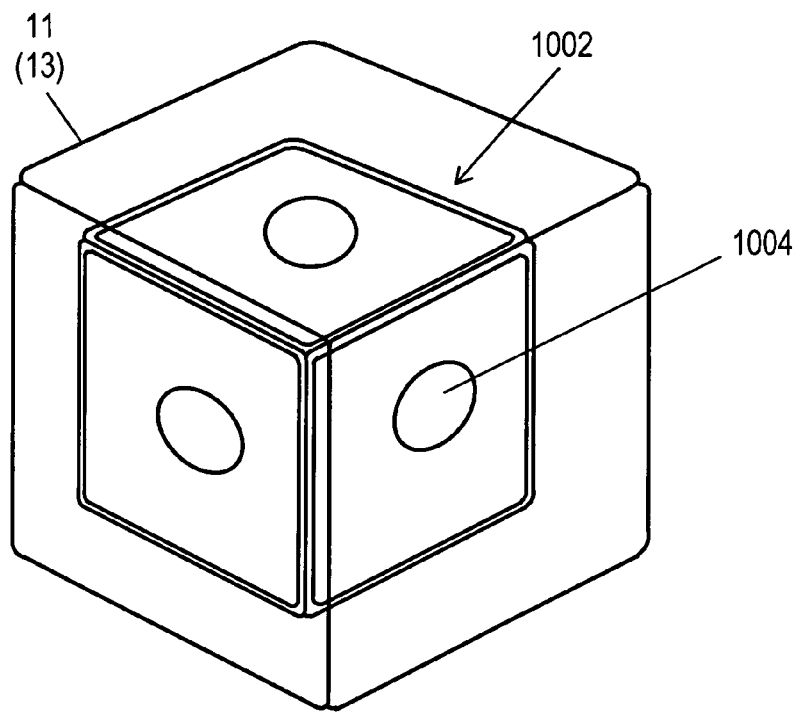
FIG. 10 shows an example of light outputting in the first embodiment.

As shown in FIG. 10, cube 1002 is provided within inside of cube 11 or 13. Cube 1002 has six light-emitting displays (e.g. LCD displays). Each of the six displays works as an individual light output unit. Due to light 1004 (e.g. a round graphic display in red color) from the display, respective light output devices appear to be faintly glowing in a red color. The light output control is conducted by changing the size of light output on display (graphic display) based on the external information received.

It is to be noted that it is important to control the light output in multi-levels (in three or more levels, including OFF state). Transmission of information may be conducted by making use of a change in the light intensity, by taking advantage of a difference in the light ON/OFF pattern, or any other means. Namely, any one of the optional light control methods (five methods have been exemplified in the above, but there can be still more different methods) may be used. This statement applies likewise also in all of the following exemplary embodiments.

Although the information processing terminals and the light output devices in the present embodiment are shaped cubic, they can assume instead a rectangular parallelepiped form, a spherical shape, a doll shape, shape of an animal, or any other forms. This applies likewise also in all of the embodiments.

Each of the operations described in the present embodiment may be implemented by means of software; the software may be distributed by placing the relevant software on a server, for example, and down-loaded. Or, the software may be stored in a CD-ROM or the like memory media for distribution. This applies likewise also in all of the embodiments.

Embodiment 2

Figure 11:
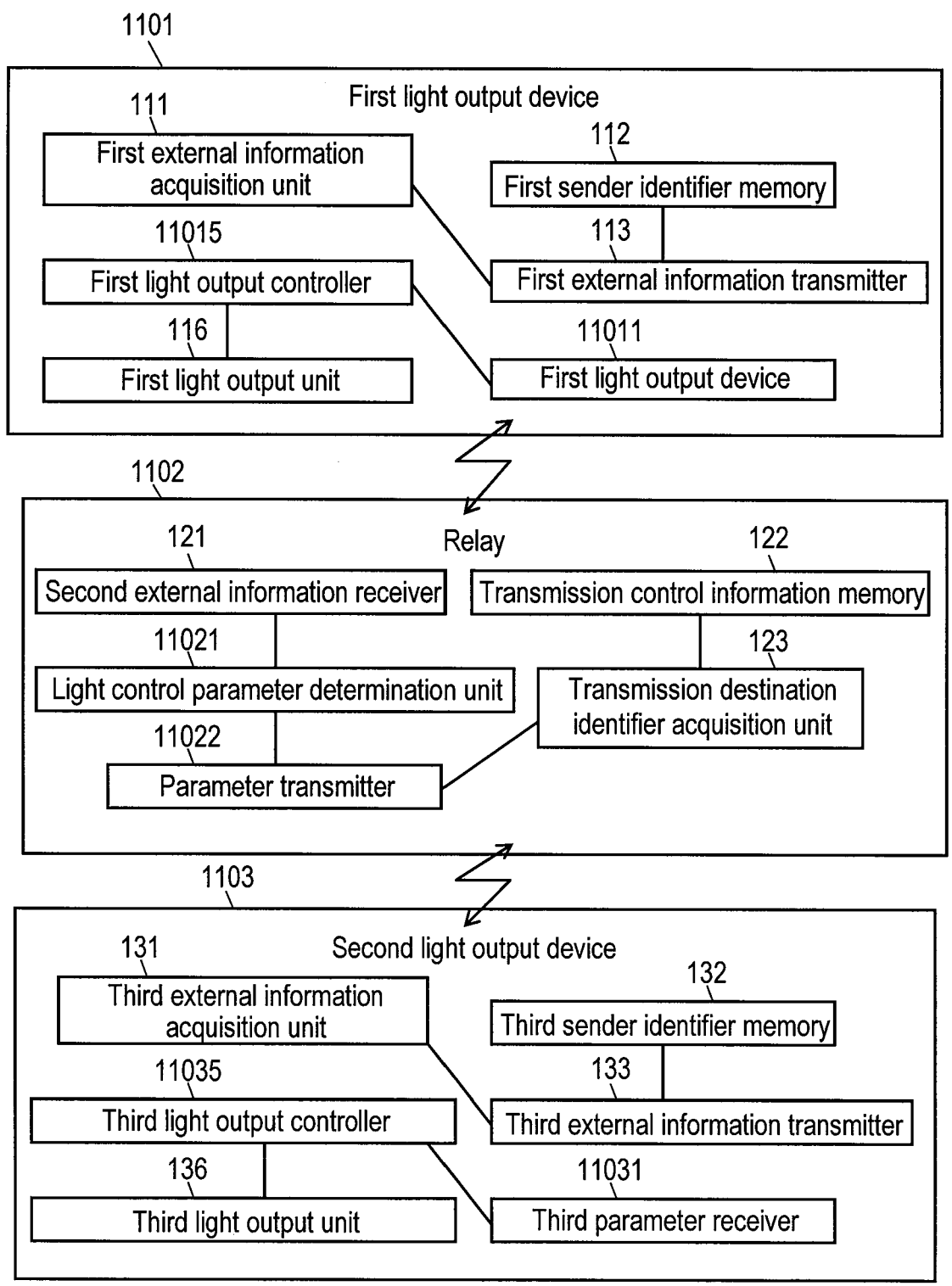
FIG. 11 is a block diagram of an information processing system in accordance with a second exemplary embodiment of the present invention.

FIG. 11 is a block diagram of an information processing system in accordance with a second exemplary embodiment.

The present information processing system has first light output device 1101, relay 1102 and second light output device 1103.

First light output device 1101 includes first external information acquisition unit 111, first sender identifier memory 112, first external information transmitter 113, first light output unit 116, first parameter receiver 11011 and first light output controller 11015.

First parameter receiver 11011 receives a light control parameter from relay 1102. First parameter receiver 11011 is implemented normally with a wireless communication apparatus, but it can be a wired communication apparatus. Or, first parameter receiver 11011 may be implemented with an apparatus for receiving broadcasting; for example, a tuner and the driver software.

First light output controller 11015 instructs light output unit 116 to output the light based on a light control parameter received at first parameter receiver 11011. First light output controller 11015 is implemented normally with software, but a dedicated circuit (hardware) may be used instead.

Relay 1102 includes second external information receiver 121, transmission control information memory 122, transmission destination identification information acquisition unit 123, light control parameter determination unit 11021 and parameter transmitter 11022.

Light control parameter determination unit 11021 determines a light output control parameter based on the first external information and the second external information received at second external information receiver 121. Light control parameter is implemented normally with software, but a dedicated circuit (hardware) may be used instead. Light control parameter determination unit 11021 may use different ALGORITHMs in determining a light output control parameter. An exemplary ALGORITHM is detailed in the following:

Parameter transmitter 11022 transmits a light control parameter determined by light control parameter determination unit 11021 to respective light output devices. Parameter transmitter 11022 is implemented normally with a wireless, or wired, communication apparatus, but a broadcasting apparatus may be used instead.

Second light output device 1103 includes third external information acquisition unit 131, third sender identifier memory 132, third external information transmitter 133, third light output unit 136, third parameter receiver 11031 and third light output controller 11035.

Third parameter receiver 11031 receives a light control parameter from relay 1102. Third parameter receiver 11031 is implemented normally with a wireless communication apparatus, but a wired communication apparatus may be used instead. Or, third parameter receiver 11031 may be implemented with an apparatus of receiving broadcasting (a tuner and the driver software, etc.).

Third light output controller 11035 instructs third light output unit 136 to output the light based on a light control parameter received at third parameter receiver 11031. Third light output controller 11035 is implemented normally with software, but a dedicated circuit (hardware) may be used instead.

Now, operation of the present information processing system is described. In the first place, operation of first light output device 1101 is described referring to FIG. 12, a flow chart.

(Step S1201) First external information acquisition unit 111 judges if an instruction to start acquiring an external information is received, or not. If the instruction is received, then it proceeds to S1202; if not received, then it repeats S1201. The starting instruction can be interpreted as an instruction to start acquiring external information; at the same time, it can be understood as an instruction to start the entire processing of FIG. 12.

(Step S1202) First external information acquisition unit 111 acquires external information of its own side (first external information).

(Step S1203) First external information transmitter 113 acquires a sender identifier from first sender identifier memory 112.

(Step S1204) First external information transmitter 113 acquires a relay identifier, which is an information for identifying a relay. The relay identifier is stored in advance in a memory not shown in the drawing. The relay identifier is the information needed for communicating with a relay; it is an IP address of relay, for example.

(Step S1205) First external information transmitter 113 transmits the external information of its own side and the sender identifier to a relay identified by the relay identifier.

(Step S1206) First parameter receiver 11011 judges if it received a light control parameter, or not. If a light control parameter is received, it proceeds to S1207; if not received, it returns to S1206.

(Step S1207) First light output controller 11015 instructs first light output unit 116 to output the light in accordance with a light control parameter received at first parameter receiver 11011.

(Step S1208) First light output unit 116 outputs the light in accordance with the light control parameter.

(Step S1209) First light output device 11 judges if a signal indicating the finish is received, or not. If the signal is received, the procedure is finished; if not received, it returns to S201.

Figure 12:
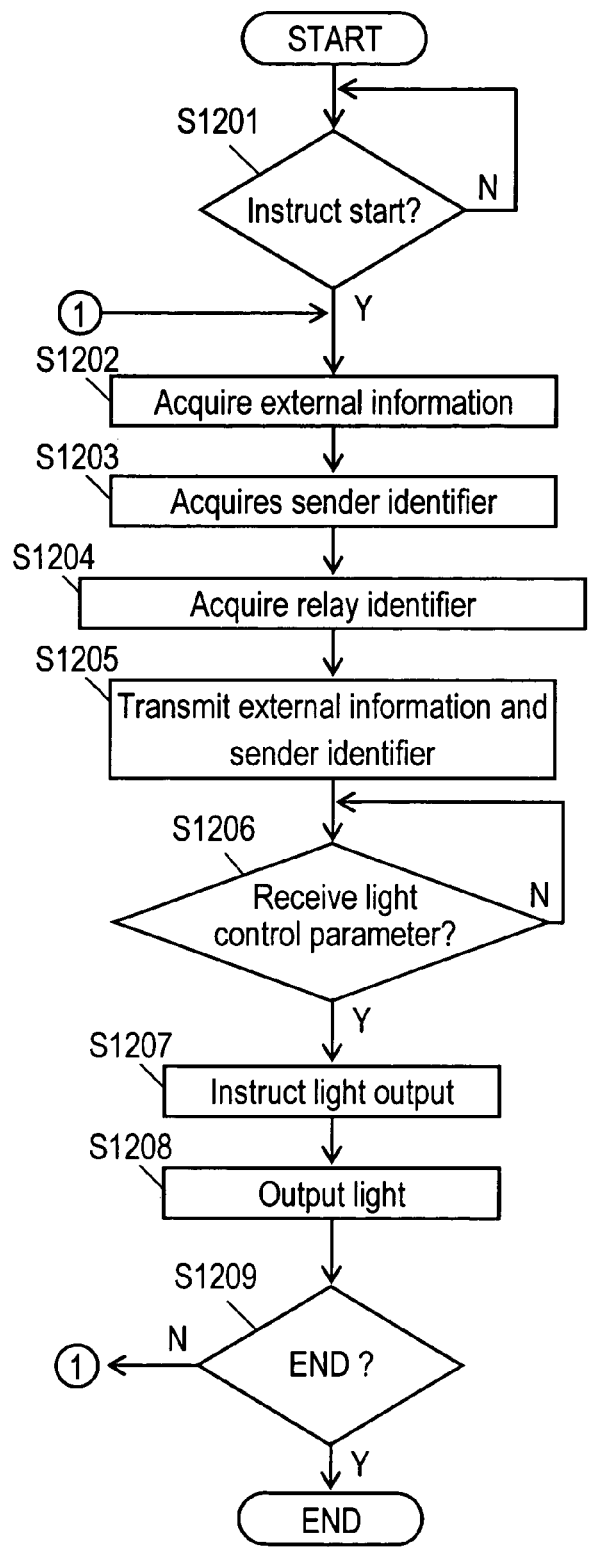
FIG. 12 is a flow chart used to describe the operation of a light output device in the second embodiment.

In the flow chart, FIG. 12, the acquisition of external information is triggered by the reception of a starting instruction. In actual practice, the starting instruction is generated by a user pressing a start button. The starting instruction can be transmitted also from second light output device 1103, relay 1102 or other devices. Or, the operation shown in the flow chart, FIG. 12, may be started without having any triggering.

Figure 13:
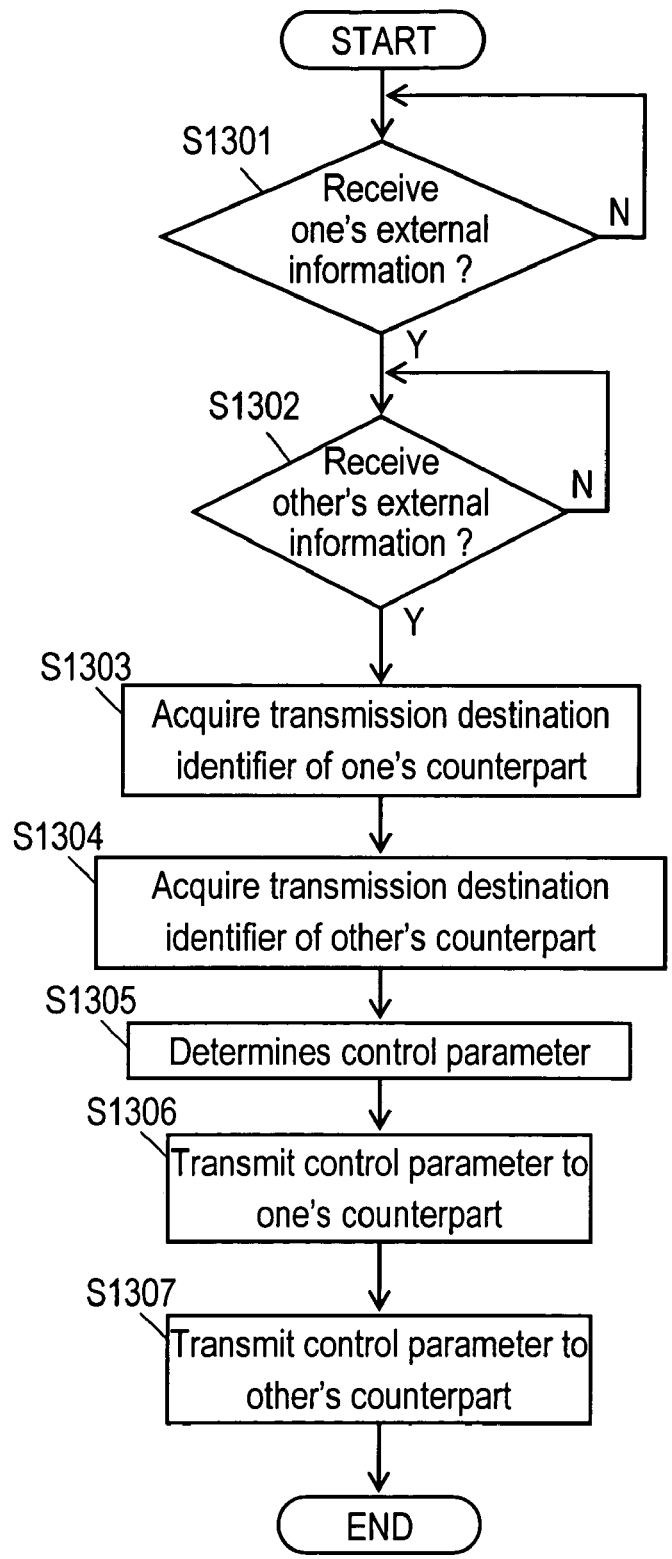
FIG. 13 is a flow chart used to describe the operation of a relay in the second embodiment.

Next, operation of relay 1102 is described referring to a flow chart shown in FIG. 13.

(Step S1301) Second external information receiver 121 judges if external information and a sender identifier are received from first light output device 1101, or not. If these are received, it proceeds to S1302; if not received, it repeats S1301.

(Step S1302) Second external information receiver 121 judges if external information and a sender identifier are received from second light output device 1103, or not. If these are received, it proceeds to S1303; if not received, it returns to S1302.

(Step S1303) Transmission destination identifier acquisition unit 123 acquires from transmission control information memory 122 a transmission destination identifier, which is the counterpart to the sender identifier received at S1301.

(Step S1304) Transmission destination identifier acquisition unit 123 acquires from the transmission control information memory a transmission destination identifier, which is the counterpart to the sender identifier received at S1302.

(Step S1305) Light control parameter determination unit 11021 determines a light control parameter based on the two peaces of external information acquired at S1301 and S1302.

(Step S1306) Parameter transmitter 11022 transmits the light control parameter determined at S1305 to the other (the destination indicated by the transmission destination identifier acquired at S1303).

(Step S1307) Parameter transmitter 11022 transmits the light control parameter determined at S1305 to the other (the destination indicated by the transmission destination identifier acquired at S1304).

In the flow chart, FIG. 13, the relay transmits a light control parameter triggered by the reception of external information. However, a light control parameter may be transmitted upon an access demand raised from second light output device 1103 or first light output device 1101.

In the flow chart, FIG. 13, second external information receiver 121 first judged if external information was received from first light output device 1101, and then judged if it is received from second light output device 1103. However, the sequence of judgments does not have a substantial meaning.

Operation of second light output device 1103 is the same as that of first light output device 1101; therefore, description on the operation of second light output device 1103 is eliminated here.

Now in the following, the operation of an information processing system in the present embodiment, as well as the shape of light output devices, etc. constituting the processing system, is described.

Suppose first light output device 1101 and second light output device 1103 have exactly the same structure, and are shaped in, for example, a cubic form as illustrated in FIG. 4.

Relay 1102's light control parameter determination unit 11021 stores a table as shown in FIG. 5. First light output device 1101 and second light output device 1103 transmit external information (pressure information) to relay 1102, and light control parameter determination unit 11021 determines a voltage based on the table, FIG. 5. For example, the item "Own pressure information" the pressure information (external information) transmitted from first light output device 1101, while "Pressure information of the other"

represents the pressure information (external information) transmitted from second light output device 1103.

In this exemplary case, if pressure information "2" is transmitted from first light output device 1101 and pressure information "25" is transmitted from second light output device 1103, the "min (n,m)" is applied thereto; the voltage is determined to be "2". Then, a control parameter "2" is transmitted to first light output device 1101 and second light output device 1103. First light output device 1101 and second light output device 1103 emit the light at the intensity of voltage "2".

It is understood from the above that when both of the holders of respective light output devices earnestly grasp the devices with strong forces, respective devices generate intense lights; if any one person among the parties is not grasping the device, there will be no light output at all. The control parameter is determined at relay 1102.

Thus in the present embodiment, external information indicating condition of respective users of light output devices are transmitted to a relay. The relay determines a parameter for controlling the light output, and transmits the parameter to respective light output devices. Respective light output devices output the information in the form of light output, implicating users' conditions in an obscure and soft mood.

Suppose, lovers each having the present light output device with them, for example, firmly grasp their own device with a strong desire for meeting together; then, each of the devices will be brilliantly lit. The lovers would feel happy when each of the couple is convinced that his, or her, partner is keeping a strong love affection to the other.

The light output device in the present embodiment has the constituent elements for acquiring external information to be sent to a relay (external information acquisition unit, sender identifier memory, external information transmitter) and the constituent elements for outputting the light (light output unit, first parameter receiver, light output controller) are contained physically within a single device. However, those constituent elements for acquiring external information to be transmitted to a relay and those constituent elements for outputting the light may be disposed physically separated. This statement applies likewise also in other light output devices described in other embodiments.

An information processing system in the present embodiment is formed of two light output devices, and a relay determines a light control parameter based on two pieces of external information. However, the light control parameter may be determined based on external information transmitted from three or more number of light output devices. This statement applies likewise also in other embodiments, including embodiment 1.

Embodiment 3

Figure 14:
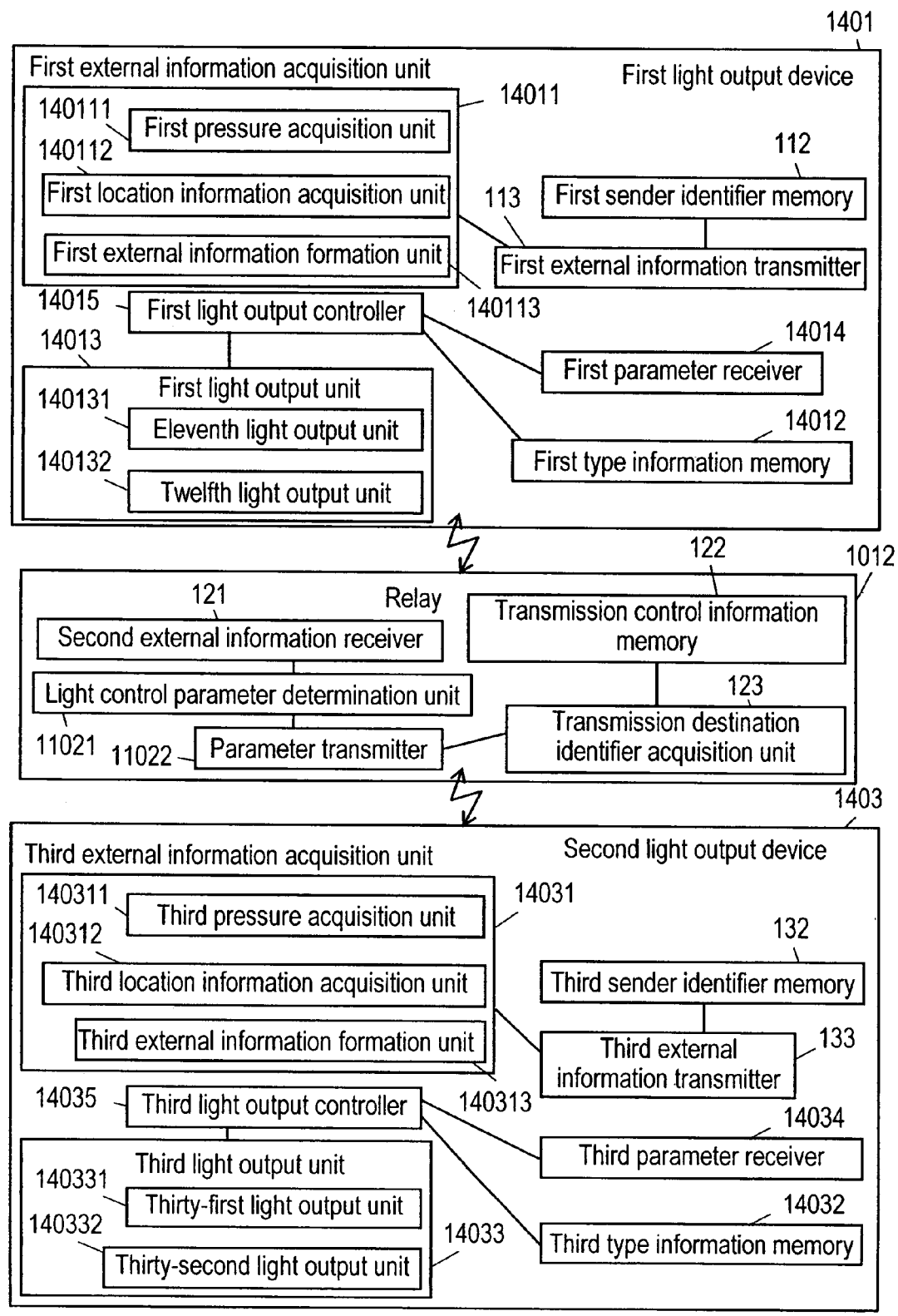
FIG. 14 is a block diagram of an information processing system in accordance with a third exemplary embodiment of the present invention.

FIG. 14 is a block diagram of an information processing system in the present exemplary embodiment.

The present information processing system is formed of first light output device 1401, relay 1102 and second light output device 1403.

First light output device 1401 includes first external information acquisition unit 14011, first type information memory 14012, first light output unit 14013, first parameter receiver 14014, first light output controller 14015, first sender identifier memory 112 and first external information transmitter 113.

First external information acquisition unit 14011 acquires external information. First external information acquisition unit 14011 includes first pressure acquisition unit 140111, first location information acquisition unit 140112 and first external information formation unit 140113.

First pressure acquisition unit 140111 acquires pressure information which is the information about a pressure. First pressure acquisition unit 140111 can be implemented with one or more number of pressure sensors. First pressure acquisition unit 140111 acquires, for example, values from six pressure sensors, as described in embodiment 1.

First location information acquisition unit 140112 acquires location information which is the information about a location where first light output device 1401 locates. First location information acquisition unit 140112 can be implemented with a receiver of GPS system, for example. In this case, the location information is GPS coordinate values. Or, a location specifying apparatus, that specifies a certain location by recognizing the intensity of electromagnetic waves transmitted from three different portable telephone stations, may be used for first location information acquisition unit 140112.

First external information formation unit 140113 forms external information based on the pressure information acquired at first pressure acquisition unit 140111 and/or the location information acquired at first location information acquisition unit 140112. The external information contains a set, or more number of sets, of type information which indicates type of the information and the information value which is a value indicated in the type information.

First type information memory 14012 stores type information, which is the object of processing by first light output device 1401. The processing here means a processing of the light outputting. Namely, the information that activates first light output device 1401 can be identified by the type information stored in first type information memory 14012. A hard disk or other non-volatile memory media may be used for first type information memory 14012; but a volatile memory media can also serve the purpose.

First light output unit 14013 outputs the light. First light output unit 14013 can be implemented with light emitting media such as an LED, a miniature lamp, etc., as described in embodiment 1 or embodiment 2. First light output unit 14013 includes two light output units, eleventh light output unit 140131 and twelfth light output unit 140132.

First parameter receiver 14014 receives a light control parameter transmitted from relay 1102. First parameter receiver 14014 can be implemented with a wireless or wired communication apparatus. An apparatus for receiving broadcasting (a tuner and the driver software) may be used instead.

First light output controller 14015 instructs light output unit 14013 to output the light based on a light control parameter received at first parameter receiver 14014. Light control parameter on pressure information controls eleventh light output unit 140131, while light control parameter on location information controls twelfth light output unit 140132. First light output controller 14015 is implemented normally with software, but a dedicated circuit (hardware) may be used instead.

Second light output device 1403 includes third external information acquisition unit 14031, third type information memory 14032, third light output unit 14033, third parameter receiver 14034, third light output controller 14035, third sender identifier memory 132 and third external information transmitter 133.

Respective functions remain the same in third external information acquisition unit 14031 and first external information acquisition unit 14011, third type information memory 14032 and first type information memory 14012, third light output unit 14033 and first light output unit 14013, third parameter receiver 14034 and first parameter receiver 14014, third light output controller 14035 and first light output controller 14015, third sender identifier memory 132 and first sender identifier memory 112, and third external information transmitter 133 and first external information transmitter 113. Therefore, no description is made here.

Third external information acquisition unit 14031 includes third pressure acquisition unit 140311, third location information acquisition unit 140312 and third external information formation unit 140313. Third light output unit 14033 includes thirty second light output unit 140331 and thirty first light output unit 140332.

Relay 1102 has the same structure as that in embodiment 2, shown in FIG. 11.

Now, the operation of present information processing system is described. In the first place, operation of first light output device 1401 is described referring to FIG. 15, a flow chart.

(Step S1501) First location information acquisition unit 140112 acquires location information.

(Step S1502) First pressure acquisition unit 140111 judges if pressure information is received, or not. If the pressure information is received, it proceeds to S1503; if not received, it skips to S1504.

(Step S1503) First pressure acquisition unit 140111 forms pressure information. The formation of pressure information means to provide the pressure information based on results of measurements made by one or more number of pressure sensors.

"Forming pressure information" means the averaging of six measured values delivered from six sensors, in an exemplary case where there are six pressure sensors.

"Forming pressure information" means, in an exemplary case where there are six pressure sensors disposed in an information terminal, to count the number of activated sensors in order to infer a state of the information terminal how a user is touching it, and to form the information based on the result of inference. Describing practically, when five sensors are activated and detected a value higher than 0, then an inference is that a user is grabbing the terminal; when four sensors are activated, then an inference is that a user is holding the terminal in a normal manner. When only one sensor is activated, an inference is that a user is simply making a touch (pushing) to the terminal with the finger.

Thus, first pressure acquisition unit 140111 generates two pieces of information, i.e. the mode of making contact and the intensity of pressure, as the pressure information.

As to the "mode of contact", number of the sensors exhibiting a value higher than "0", for example, is treated to represent a contact mode.

As to the intensity of pressure, the "gross of values detected by sensors exhibiting a value higher than 0"/"number of sensors exhibiting a value higher than 0", for example, is taken as the value to represent a pressure intensity. These two pieces of information are generated as the pressure information.

(Step S1504) First external information formation unit 140113 forms external information out of location information and/or pressure information. The external information contains a set, or more number of sets, of type information which indicates type of information and information value which is a value indicated in the type information.

(Step S1505) First external information transmitter 113 acquires a sender identifier for identifying first light output device 1401 from sender identifier memory 112.

(Step S1506) First external information transmitter 113 acquires a relay identifier stored in advance in a memory not shown in the drawing.

(Step S1507) First external information transmitter 113 transmits the external information formed at S1504 and the sender identifier acquired at S1505 to a relay identified by the relay identifier.

(Step S1508) Whether first parameter receiver 14014 received a light control parameter, or not, is judged. If the parameter is received, it proceeds to S1508; if not received, it repeats S1508.

(Step S1509) First light output controller 14015 judges whether there is a pressure parameter, which is a parameter on output of pressure information, contained in the control parameter received at S1508, or not. If yes, it proceeds to S1510; if not, it skips to S1512. Pressure parameter is acquired at this stage.

(Step S1510) First light output controller 14015 instructs eleventh light output device 140131 to output the light based on the acquired pressure parameter.

(Step S1511) Eleventh light output device 140131 outputs the light in accordance with the pressure parameter.

(Step S1512) First light output controller 14015 judges whether there is a location parameter, which is a parameter on output of location information, contained in the control parameter received at S1508, or not. If yes, it proceeds to S1513; if not, it skips to S1515. Location parameter is acquired at this stage.

(Step S1513) First light output controller 14015 instructs twelfth light output device 140132 to output the light based on the acquired location parameter.

(Step S1514) Twelfth light output device 140132 outputs the light based on the location parameter.

(Step S1515) First light output device 1401 judges whether an end signal is inputted, or not. If yes, the light output is finished; if not, it returns to S1510.

Figure 15:
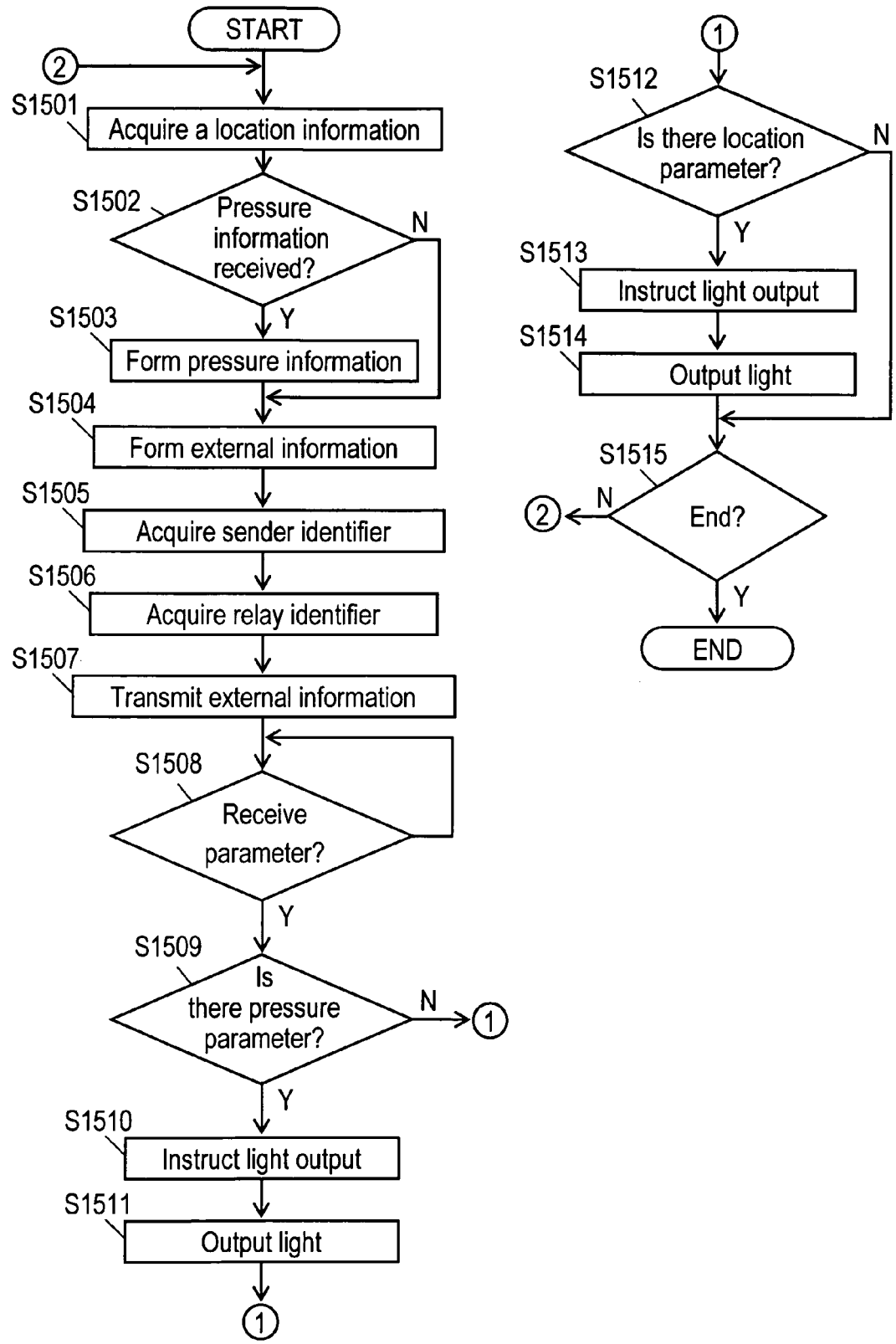
FIG. 15 is a flow chart used to describe the operation of a light output device in the third embodiment.

In the flow chart, FIG. 15, external information is acquired without having any triggering. However, the operation may be started after having a triggering by, for example, a user of first light output device 1401 pressing a start button. Or, the acquisition of external information at S1501 may be started upon receiving a triggering signal from second light output device 1403, relay 1102 or other devices.

Operation of second light output device 1403 is identical to that of first light output device 1401. Therefore, description of the operation of second light output device 1403 is eliminated here.

Now, the operation of an information processing system in the present embodiment is described practically.

Figures 16, 17, 18, 19:
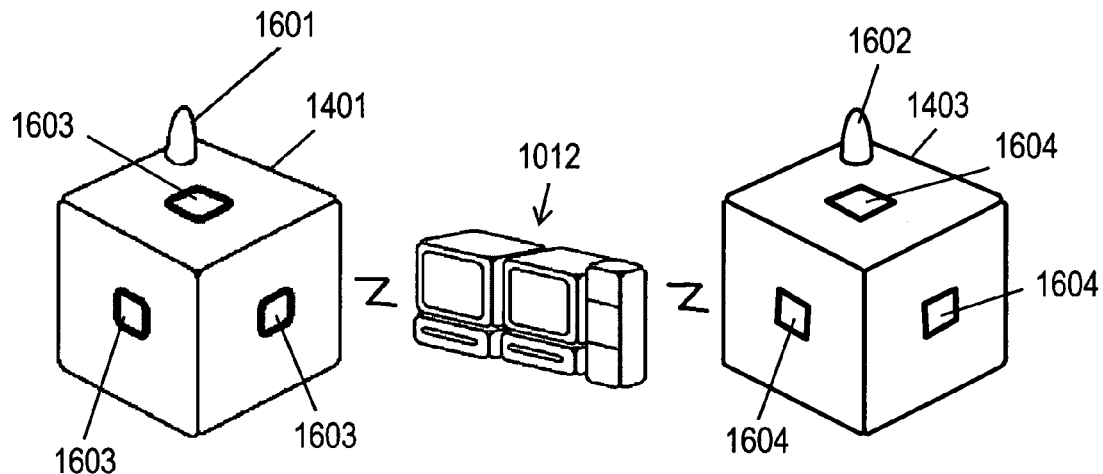
FIG. 16 illustrates the concept of an information processing system in the third exemplary embodiment.
FIG. 17 shows an exemplary structure of pressure information in the third embodiment.
FIG. 18 is an example of pressure information in the third embodiment.
FIG. 19 shows an example of location information in the third embodiment.

Suppose first light output device 1401 and second light output device 1403 are cubic shaped, as shown in FIG. 16. Each of first light output device 1401 and second light output device 1403 is provided with six pressure sensors, 1603, 1604, in the respective faces; and one GPS receiver. The above-configured two devices acquire such information as shown in FIG. 17, through the pressure information acquisition unit. Respective GPS receivers are provided with GPS receiving antenna, 1601, 1602.

An actual example of pressure information is shown in FIG. 18. Respective devices acquire location information in terms of GPS coordinate values (X, Y, Z) through location information acquisition apparatus. An actual example of location information is shown in FIG. 19.

First external information formation unit 140113 and third external information formation unit 140313 acquire pressure information, which is based on the six pieces of pressure information. In practice, the "gross value of information other than 0"/"number of pieces of information other than 0" is calculated for the information value. In the present exemplary case; (0+0+20+5+5+20)/4 makes a value 12.5. Thus, the pressure information yielded is: "Information type; Pressure information, ID; 1, Value information; 12.5".

In this way, first external information formation unit 140113 and third external information formation unit 140313 form external information, respectively. For example, first external information formation unit 140113 provides two sets of records having two types of information, information value and IDs, as shown in FIG. 20. Third external information formation unit 140313 provides two sets of records having two type information, information value and IDs, as shown in FIG. 21. Namely, external information of respective devices have one or more sets, of records containing "type information", "information value" and "ID". The "ID" is information for identifying type information; so, "ID" can be "type information".

First external information transmitter 113 and third external information transmitter 133 transmit the above external information to relay 1102.

Relay 1102's light control parameter determination unit 11021 determines respective light control parameters based on the pressure information and location information of respective devices.

In practice, light control parameter determination unit 11021 determines light control parameter based on the external information shown in FIG. 20 and the external information shown in FIG. 21. When, the pressure parameter is determined in accordance with the table shown in FIG. 5. Namely, light control parameter determination unit 11021 stores the table of FIG. 5. If relay 1102 receives two pieces of pressure information, "12.5" and "5", then the "min (n, m)" of FIG. 5 is applied; the "min (12.5, 5)" leads to a pressure parameter "5". Light control parameter determination unit 11021 stores the table of FIG. 22. Light control parameter determination unit 11021 calculates, from the location information contained in the two pieces of received external information, a distance between first light output device 1401 and second light output device 1403. The distance is calculated based on two GPS coordinates (location information contained in the two pieces of external information). Based on the distance thus calculated, a "voltage" is determined in accordance with the table shown in FIG. 22. The "voltage" represents location parameter. Namely, the closer the distance between first light output device 1401 and second light output device 1403 is, the higher is the voltage to be applied on first light output device 1401 and second light output device 1403 for outputting the light.

Suppose first type information memory 14012 and third type information memory 14032 keep "location information" and "pressure information", as the type information. In this case, the two records of information shown in FIG. 20 and FIG. 21 are object of the light control. In the present embodiment, first light output controller 14015 and third light output controller 14035 control eleventh light output unit 140131 and thirty first light output unit 140331 in accordance with the value of "location parameter" contained in the light control parameter sent from relay 1012; and control, respectively, twelfth light output unit 140132 and thirty second light output unit 140332 in accordance with the value of "pressure parameter" contained in the light control parameter. Eleventh light output unit 140131 and thirty first light output unit 140331 are formed of blue LED, for example, and intensity of the light emission goes higher along with the higher voltage applied thereon. Twelfth light output unit 140132 and thirty second light output unit 140332 are formed of red LED, for example, and intensity of the light emission goes higher along with the higher voltage applied thereon.

Figure 23:
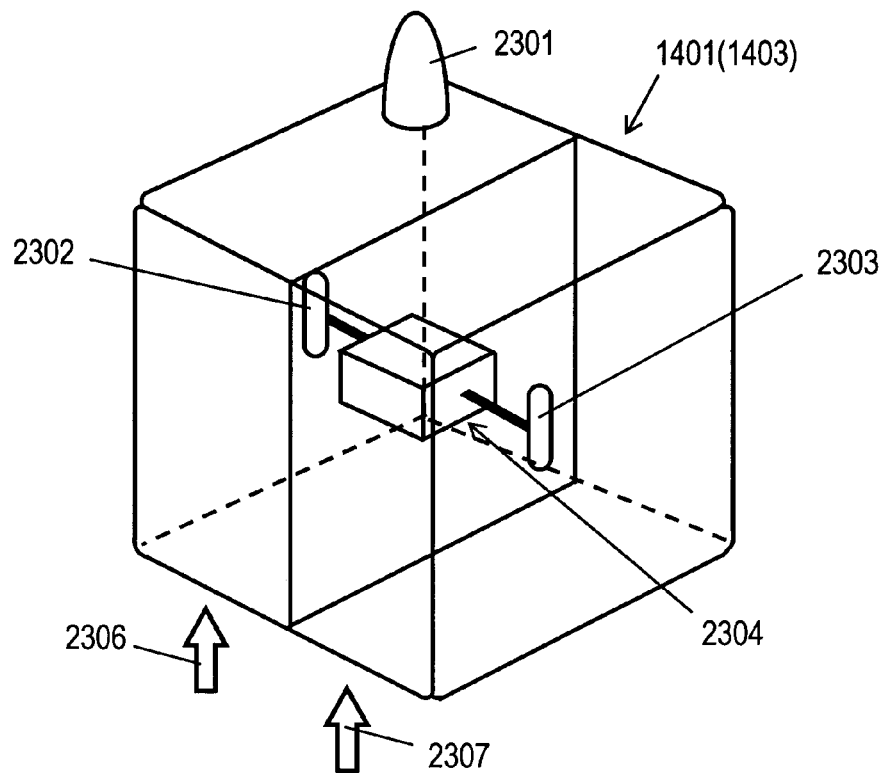
FIG. 23 shows the appearance of a light output device in the third embodiment.

FIG. 23 shows a simplified appearance of first light output device 1401 and second light output device 1403. Light output device 1401, or 1403, includes GPS antenna 2301, blue LED 2302, red LED 2303 and light output controller 2304. Arrow mark 2306 indicates inputting location information, while arrow mark 2307 indicates inputting pressure information.

Figure 24:
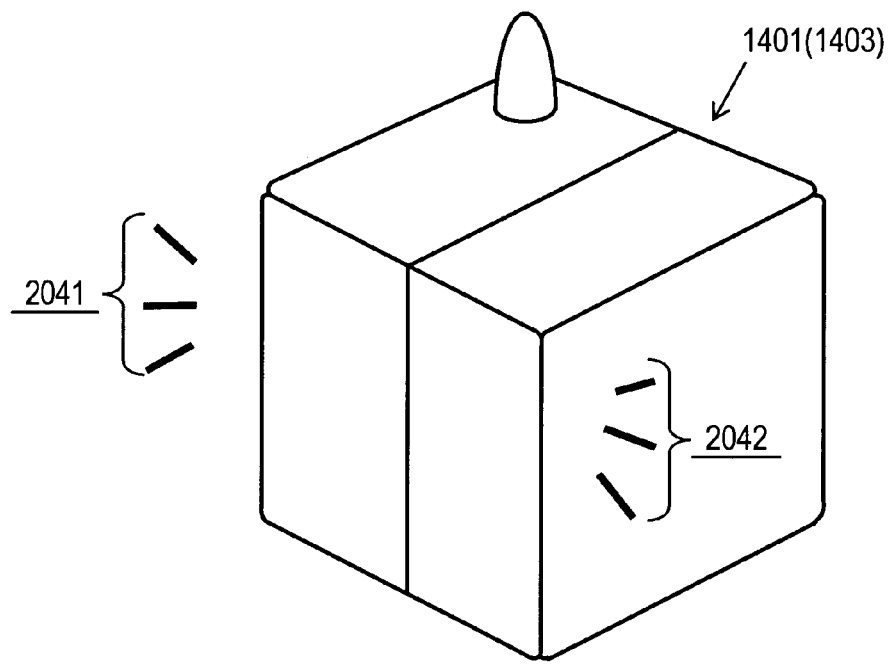
FIG. 24 shows a light output device in the third embodiment emitting the light.

FIG. 24 shows how first light output device 1401 and second light output device 1403 emit light 2401 and light 2402. If the received external information contains a control parameter other than that on "location information" and that on "pressure information", the other control parameter is ignored.

Through the above-described light control, distance between a holder of first light output device and a holder of second light output device can be communicated in a soft mood. Therefore, information other than external information may be used, instead of "controlling the light output based on external information" as described in the above.

Furthermore, based on a plurality of pieces of location information and the time when the each location information were acquired, moving direction of the first light output device and the second light output device can be acquired. Through the moving directions, one can judge whether the first light output device and the second light output device are approaching, or parting away. A relay may determine a control parameter based on a judgment made after the directional information. Namely, a relay may determine a control parameter so that the location parameter (voltage) is greater when it is approaching closer, even if there is a long distance; whereas, the location parameter (voltage) is smaller when it is parting away, even if the distance is short.

As for the technology to acquire the direction of moving, a known technology making use of the geomagnetic sensor, etc. may be used.

Respective grasping strengths holding the first light output device and the second light output device are outputted to first light output unit's twelfth light output unit and third light output unit's thirty second light output unit. As described earlier, when respective holders firmly grasp the first light output device or the second light output device, intensity of the grasping strength can be outputted in terms of the light intensity.

For example, suppose lovers are getting closer for meeting personally and each of them is firmly grasping their respective first light output device and second light output device, intensity of the blue output (output of location information) and the red output (pressure information) from the cubic shaped light output devices is strengthened gradually by the above-described light output operation. Thus the love affection towards personal rendezvous is communicated in a soft mood.

As described in the above, respective light output devices in the present embodiment are lightened by a plurality of types of information generated by respective device bearers. Thereby, a plurality of states about the respective individuals can be conveyed to the other. Thus, a communication system is offered, with which a number of pieces of information can be communicated from one person to other person in a soft and obscure mood.

In the present exemplary embodiment, location information and pressure information are selected for the external information. However, any other information may be used, in so far as it represents state of things of respective device bearers. This statement applies likewise in other embodiments, too.

Although the method of light output control has been described in terms of controlling the intensity of light output, the light may be controlled by such other methods as described in embodiment 1 (any one of the five light control methods may be used). This statement applies likewise also in all of the other embodiments.

Although the first light output unit and the third light output unit have been provided, respectively, with two light output elements, three or more number of light output elements may be provided; or only one light output element would do. This statement applies likewise in other embodiments, too.

Although location information has been acquired in the present embodiment through a GPS method, other technologies, such as a technology in which the location information is acquired by taking advantage of electromagnetic wave generated from portable telephone stations, may be used instead for the purpose. Since such other technologies have already been made known, detailed description on this is eliminated. This statement also applies likewise in other embodiments.

Although the first light output unit has been controlled based on a location information, while and the second light output unit has been controlled based on pressure information, and such a procedure has been fixed in the present embodiment, the way of controlling which light output unit on which information can be customized.

Furthermore, the external information is handled as the object of light control, in a case where type information contained in external information received at the first light output device and the second light output device is stored in respective type information memories (namely, in a case where the type information contained in the external information and the type information stored in the first or the third type information memory coincide). However, if the type information contained in the external information and the type information stored in respective type information memories are in a certain specific relationship, then the external information may be treated as the object of light control. This statement also applies likewise in other embodiments.

Embodiment 4

Figure 25:
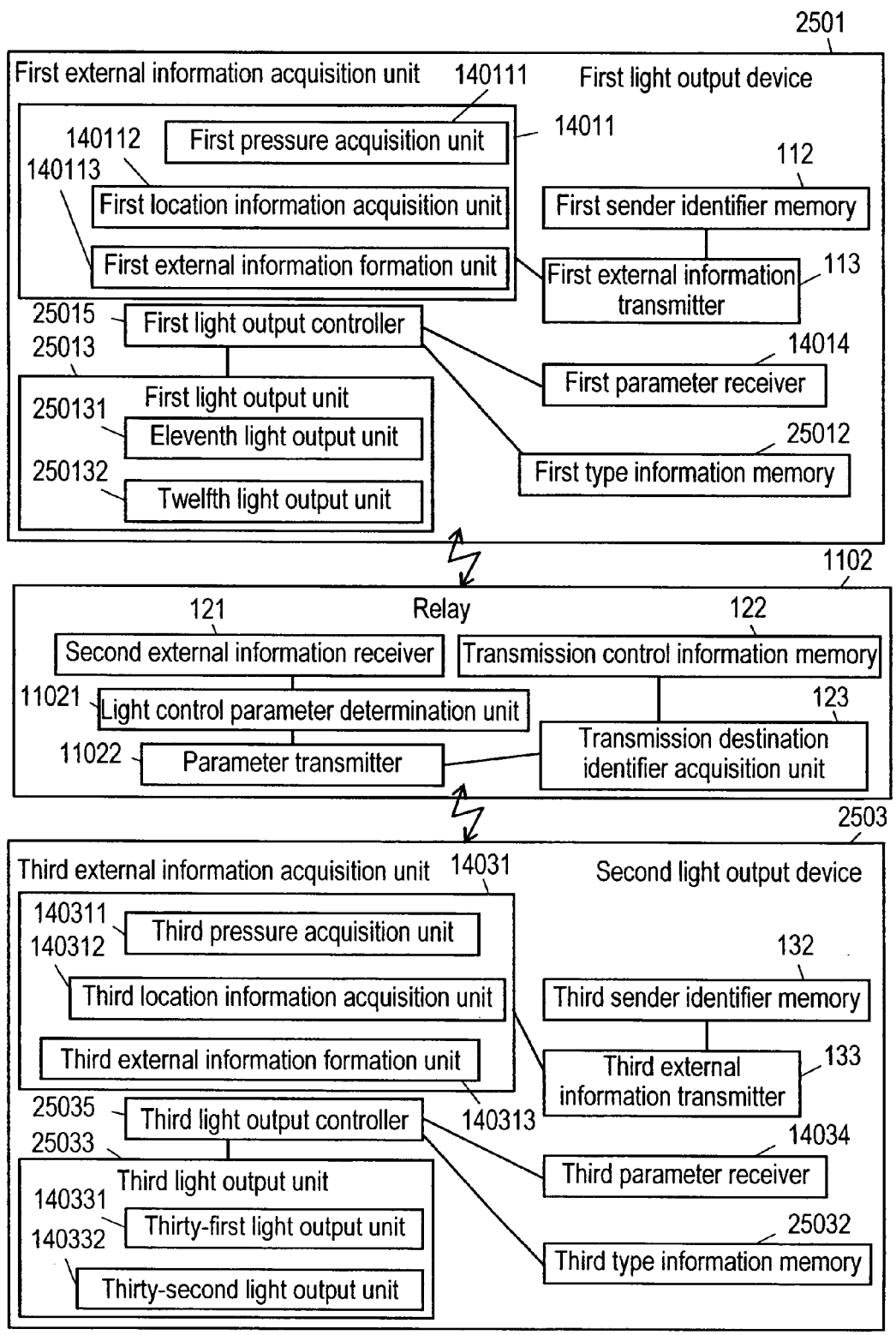
FIG. 25 is a block diagram of an information processing system in accordance with a fourth exemplary embodiment of the present invention.

FIG. 25 is a block diagram of an information processing system in accordance with a fourth exemplary embodiment.

The present information processing system is formed of first light output device 2501, relay 1102 and second light output device 2503.

First light output device 2501 includes first external information acquisition unit 14011, first type information memory 25012, first light output unit 25013, first parameter receiver 14014, first light output controller 25015, first sender identifier memory 112 and first external information transmitter 113.

First external information acquisition unit 14011 acquires an external information. First external information acquisition unit 14011 includes first pressure acquisition unit 140111, first location information acquisition unit 140112 and first external information formation unit 140113.

First type information memory 25012 stores a light output control table.

The light output control table stores light output control record for one or more devices. The light output control record contains a type information which is the object of processing by first light output device 2501 (information corresponding to light control parameter), a light output unit identifier which identifies a light output unit that responds to the type information and a light output method identifier which identifies a light outputting method.

First type information memory 25012 may be formed with a hard disk or other non-volatile memory media; but, it may be formed with a volatile memory instead.

First light output unit 25013 outputs the light. First light output unit 25013 includes two light output units, eleventh light output unit 250131 and twelfth light output unit 250132. Respective light output units can be implemented with an LED, a miniature lamp or other light output media, as described earlier in embodiment 1 through embodiment 3.

First light output controller 25015 instructs eleventh light output unit 250131 and twelfth light output unit 250132 in light output unit 25013 to output the light based on a light control parameter received at first parameter receiver 14014.

First light output controller 25015 instructs a light output unit identified by a light output method identifier included in a light output control record corresponding to the information type contained in a light control parameter received at first parameter receiver 14014 to output the light in accordance with a light output method identified by a light method identifier included in the light output control record.

First light output controller 25015 can be implemented normally with software; but a dedicated circuit (hardware) may be used instead for the purpose.

Second light output device 2503 includes third external information acquisition unit 14031, third type information memory 25032, third light output unit 25033, third parameter receiver 14034, third light output controller 25035, third sender identifier memory 132 and third external information transmitter 133.

Third external information acquisition unit 14031, third type information memory 25032, third light output unit 25033, third parameter receiver 14034, third light output controller 25035, third sender identifier memory 132 and third external information transmitter 133 performs identical functions, respectively, to those of first external information acquisition unit 14011, first type information memory 25012, first light output unit 25013, first parameter receiver 14014, first light output controller 25015, first sender identifier memory 112 and first external information transmitter 113. Therefore, the description is eliminated here.

Third external information acquisition unit 14031 includes third pressure acquisition unit 140311, third location information acquisition unit 140312 and third external information formation unit 140313. Third light output unit 14033 includes thirty first light output unit 140331 and thirty second light output unit 140332.

Relay 1102 has the same structure as that shown in FIG. 11, embodiment 2.

Now the operation of first light output device 2501 is described with reference to FIG. 26, a flow chart.

(Step S2601) First location information acquisition unit 140112 acquires location information.

(Step S2602) First pressure acquisition unit 140111 judges if pressure information is received, or not. If received, it proceeds to S2603; if not received, it skips to S2604.

(Step S2603) First pressure acquisition unit 140111 forms pressure information.

The formation of pressure information means to provide the pressure information to be transmitted based on results of measurements made by one or more number of pressure sensors. "Forming pressure information" means the averaging of six measured values delivered from six sensors, in an exemplary case where there are six pressure sensors. "Forming pressure information" means the following processing, for example.

Suppose there are six pressure sensors disposed in an information terminal, counting the number of activated sensors in order to infer a state of the information terminal how a user is touching it, and to form the information based on the result of inference.

Describing practically, when five sensors detect a value higher than 0, then an inference is that a user is grabbing the terminal; when four sensors are activated, then an inference is that a user is holding the terminal in a normal manner.

When only one sensor is activated, an inference is that a user is simply making a touch (pushing) to the terminal with the finger.

Thus, first pressure acquisition unit 140111 generates two pieces of information for the pressure information; the information about the mode of making contact (e.g. taking the number of sensors exhibiting a value higher than 0 as an indication of the mode of contact) and the information about the intensity of pressure (e.g. taking the "gross of values detected by sensors exhibiting a value higher than 0"/"number of sensors exhibiting a value higher than 0" as an indication of the intensity value of pressure).

(Step S2604) First external information formation unit 140113 forms external information out of a location information and/or a pressure information. The external information contains one or more sets of type information, which shows a type of the information, and information value, which represents the value exhibited by the type information.

(Step S2605) First external information transmitter 113 acquires a sender identifier for identifying first light output device 1401, from sender identifier memory 112.

(Step S2606) First external information transmitter 113 acquires a relay identifier, which is stored in advance in a memory not shown in the drawing.

(Step S2607) First external information transmitter 113 transmits the external information formed at S2604 and a sender identifier acquired at S2605 to a relay identified by the relay identifier.

(Step S2608) First light output controller 25015 judges whether first parameter receiver 14014 received a light control parameter, or not. If the parameter is received, it proceeds to S2609; if not received, it repeats S2608.

(Step S2609) First light output controller 25015 replaces the counter i with 1.

(Step S2610) First light output controller 25015 judges whether there is an i-th type information control parameter contained in the light control parameter received at S2608, or not. If yes, it proceeds to S2611; if not, it skips to S2613.

(Step S2611) First light output controller 25015 refers to a light output control table stored in first type information memory 25012, and uses a light output unit identifier and a light output method identifier that correspond to the type information having a certain specific relationship with the i-th type information control parameter, from a memory not shown in the drawing. And, first light output controller 25015 instructs a light output unit identified by the light output device identifier to output the light in accordance with a light output method identified by the light output method identifier at a value contained in the received light control parameter.

(Step S2612) The light output unit of light output unit 25013 outputs the light in accordance with the instruction given at S2611.

(Step S2613) First light output controller 25015 increases the counter i by 1.

Figure 26:
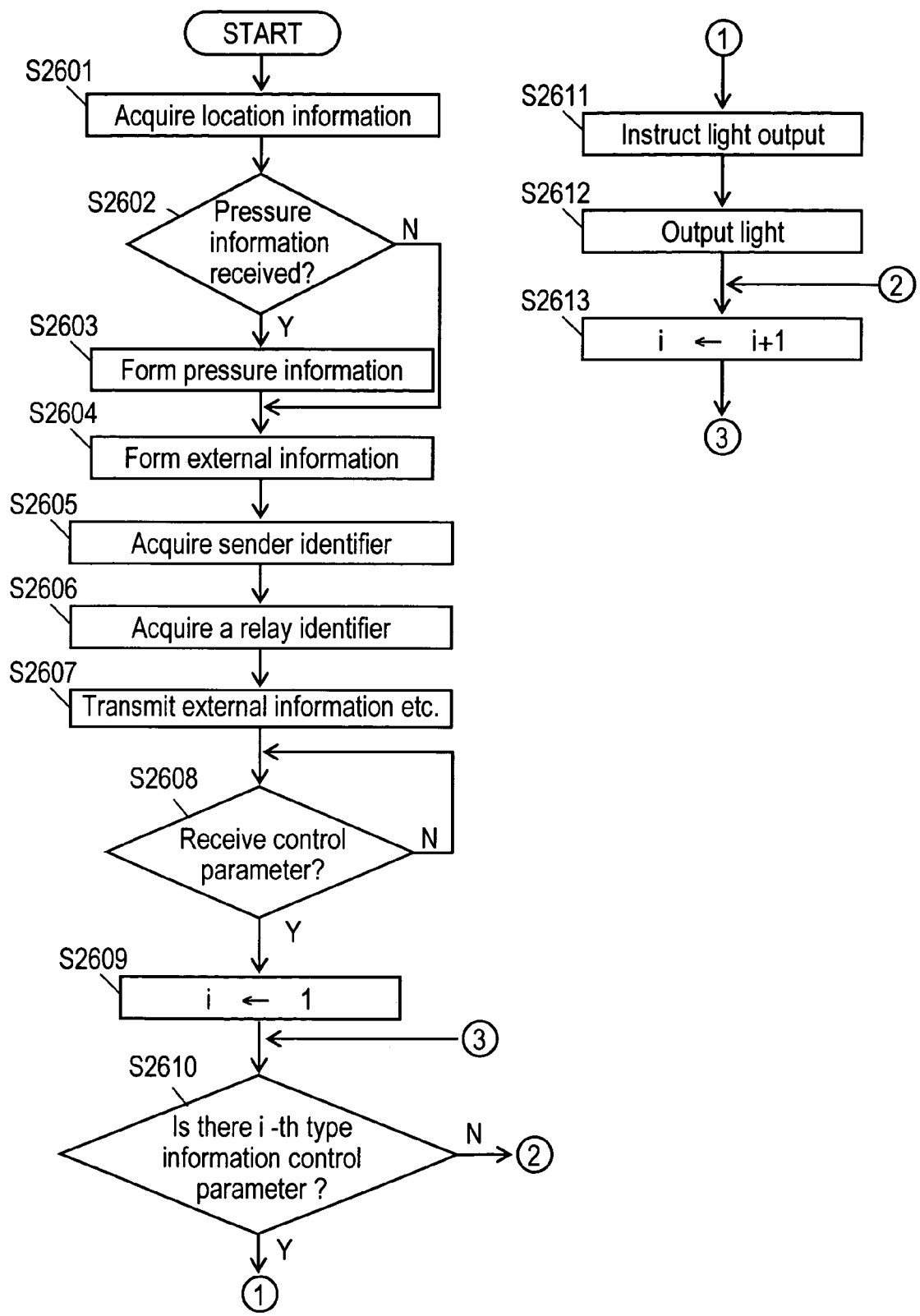
FIG. 26 is a flow chart used to describe the operation of a light output device in the fourth embodiment.

Although first light output device 2501 in FIG. 26 simply waited for a delivery of light control parameter, first light output device 2501 may ask, directly or indirectly, relay 1102 for delivering a light control parameter.

In the flow chart, FIG. 26, the counter i is incremented after the entire control parameters are taken out, without any specific purpose, and the light outputting is continued. However, there is no need for incrementing the counter i when all of the control parameters are taken away.

Although no description was made regarding the flow chart, FIG. 26, the processing of FIG. 26 is terminated at such occasions when the power supply is turned OFF, or interrupted by a finish signal.

Now, the operation of an information processing system in the present embodiment is described practically.

Suppose, a light output control table as shown in FIG. 27 is stored in first type information memory 25012. The light output control table containing, for example, a plurality of light output control records, in which "light output unit identifier", "type information" and "light output method identifier", for example, are included, as described earlier. Suppose further, that eleventh light output unit and twelfth light output unit are compatible with the light control methods identified by light output control method identifier as shown in FIG. 28; and that the data of FIG. 28 are stored in advance in, for example, first type information memory.

The "Light output method identifier" of FIG. 27 can be selected from among the five light output control method identifiers shown in FIG. 28. That is, the "Light output unit", "Type information" and "Light output method identifier" shown in FIG. 27 can be customized using such a panel, "Type Information Light Output Method Identifier Setting Panel", as shown in FIG. 29.

FIG. 29 is an exemplary panel, showing a menu for customizing the light output method identifiers for the twelfth light output unit.

Thus, the light output is controlled based on "type information" and "light output method identifier", set for one or more respective light output units and a parameter received at the first parameter receiver.

Describing practically, suppose external information shown in FIG. 20 and FIG. 21, for example, are transmitted from first light output device 2501 and second light output device 2503, respectively, to relay 1102. At relay 1102, a light control parameter for the pressure information and a light control parameter for the location information are determined based on the tables shown in FIG. 5 and FIG. 22. Relay 1102's light control parameter determination unit 11021 decides e.g. "pressure information's light control parameter 5, location information's light control parameter 10". Relay 1102's parameter transmitter 11022 transmits the light control parameter decided at light control parameter determination unit 11021 to first light output device 2501 and second light output device 2503.

Figure 30:
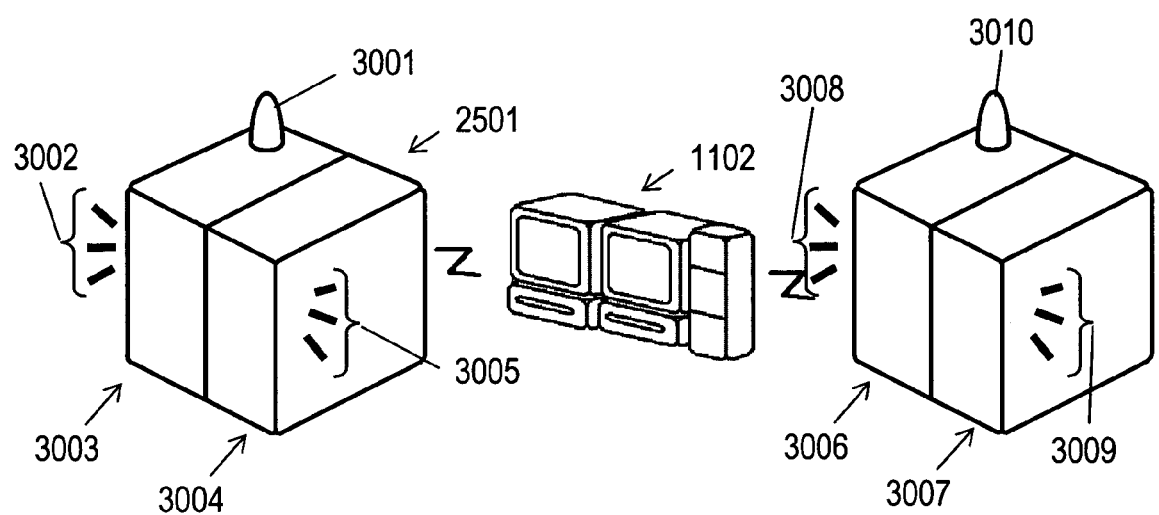
FIG. 30 illustrates the concept of an information processing system in the fourth embodiment.

As shown in FIG. 30, first light output device 2501 and second light output device 2503 output the light. In this case, first light output device 2501 emits light 3002 at the half portion 3003 in accordance with the parameter of pressure information; and emits light 3005 at the other half portion 3004 in accordance with the parameter of location information. Likewise, second light output device 2503 emits, at the half portion 3006 and the other half portion 3007, light 3008 and light 3009, respectively. First light output device 2501 and second light output device 2503 are provided, respectively, with GPS antenna 3001 and GPS antenna 3010.

When respective light output devices receive pressure information's control parameter "5", respective light output units output "blinking" light in accordance with the control parameter "5". Practically described, it is controlled in the following manner. The greater the pressure information's control parameter is, the shorter is the blinking interval. If the pressure information value is "X", the light output is switched ON/OFF at an interval of 10/X.

When respective light output devices receive location information's control parameter "10", respective light output units output "revolving" light in accordance with the control parameter "10". Practically described, it is controlled in the following manner. The greater is the location information's control parameter, the faster is the revolving speed. An example, a reflector on a revolving disk disposed besides the light source revolves faster if the location information's control parameter has a greater value.

As described in the above, respective light output devices in the present embodiment are lightened by a plurality of types of information generated by respective device bearers. Thereby, a plurality of states the respective individuals can be conveyed to the other. Thus, a communication system is offered, with which a number of information can be communicated from one person to other person in a soft and obscure mood.

The type information (control parameter), the light output method and the light output unit, to which respective light output devices respond, can be customized. Therefore, users of respective light output devices can change the type information (control parameter), the light output method and the light output unit depending on his, or her, spiritual mood of the day, for example. A light output device in the present embodiment can be adapted to satisfy the needs of users, take the following for example.

"Today, I would like to see the distance (location) between the partner and myself", "Tomorrow, I would like to see the partner's strength of grasping the cube, and that of myself", "In the day after tomorrow, I would like to see the difference between the partner and myself in the level of business profession (the processing particulars will be described in other embodiment)".

The light control in the present embodiment is performed when a type information contained in a light control parameter received at respective light output devices and a type information stored in various type information memory coincide. However, if the two pieces of information are in a certain specific relationship, these may be treated as the object of light output control. The terminology, certain specific relationship, refers to a situation where, for example, pieces of type information are classified into groups, and the type information contained in light control parameter and the type information stored in various type information memory are in the same group. There can be many other certain specific relationships. This statement likewise applies also in other embodiments.

Although the light output control table in the present embodiment is controlled in the light output device, it may be controlled instead at the relay. In the latter case, as to which information (type information) respective light output devices' one or more number of light output units react, or as to what light output control (e.g. revolving light, blinking light, etc.) is to be enforced are decided based on the light output control table kept at the relay. Or, the specific light control method may be transmitted from the relay to the light output device, and the light output device outputs the light in accordance with the received light control method. In this configuration, the structure of a light output device can be simplified.

Embodiment 5

Figure 31:
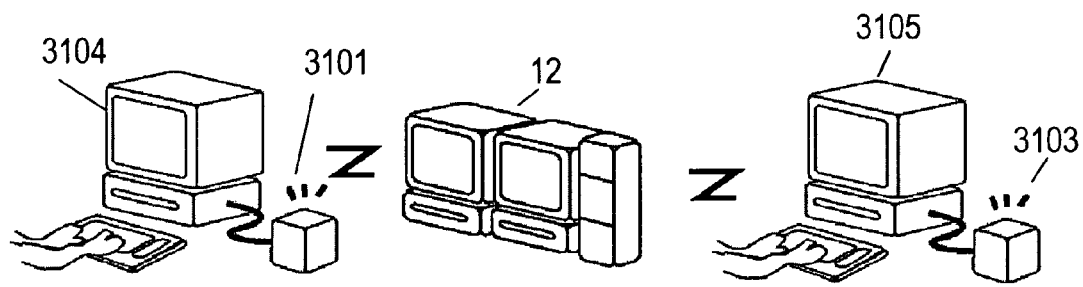
FIG. 31 illustrates the concept of an information processing system in a fifth exemplary embodiment.

FIG. 31 illustrates the concept of an information processing system in accordance with the present embodiment. The present information processing system includes first light output device 3101, relay 12, second light output device 3103, first information processing terminal 3104 and second information processing terminal 3105.

First information processing terminal 3104 and second information processing terminal 3105 are formed with computers.

First information processing terminal 3104 and second information processing terminal 3105 detect a data input signal delivered from a keyboard or the like inputting apparatus, and send the signal to first light output device 3101 and second light output device 3103. First light output device 3101 and second light output device 3103 count, respectively, the number of data inputted in a certain specific time from the data input signal, to obtain an input speed information which represents the data input speed. First light output device 3101 and second light output device 3103 transmit the external information containing the input speed information to relay 12.

Figure 32:
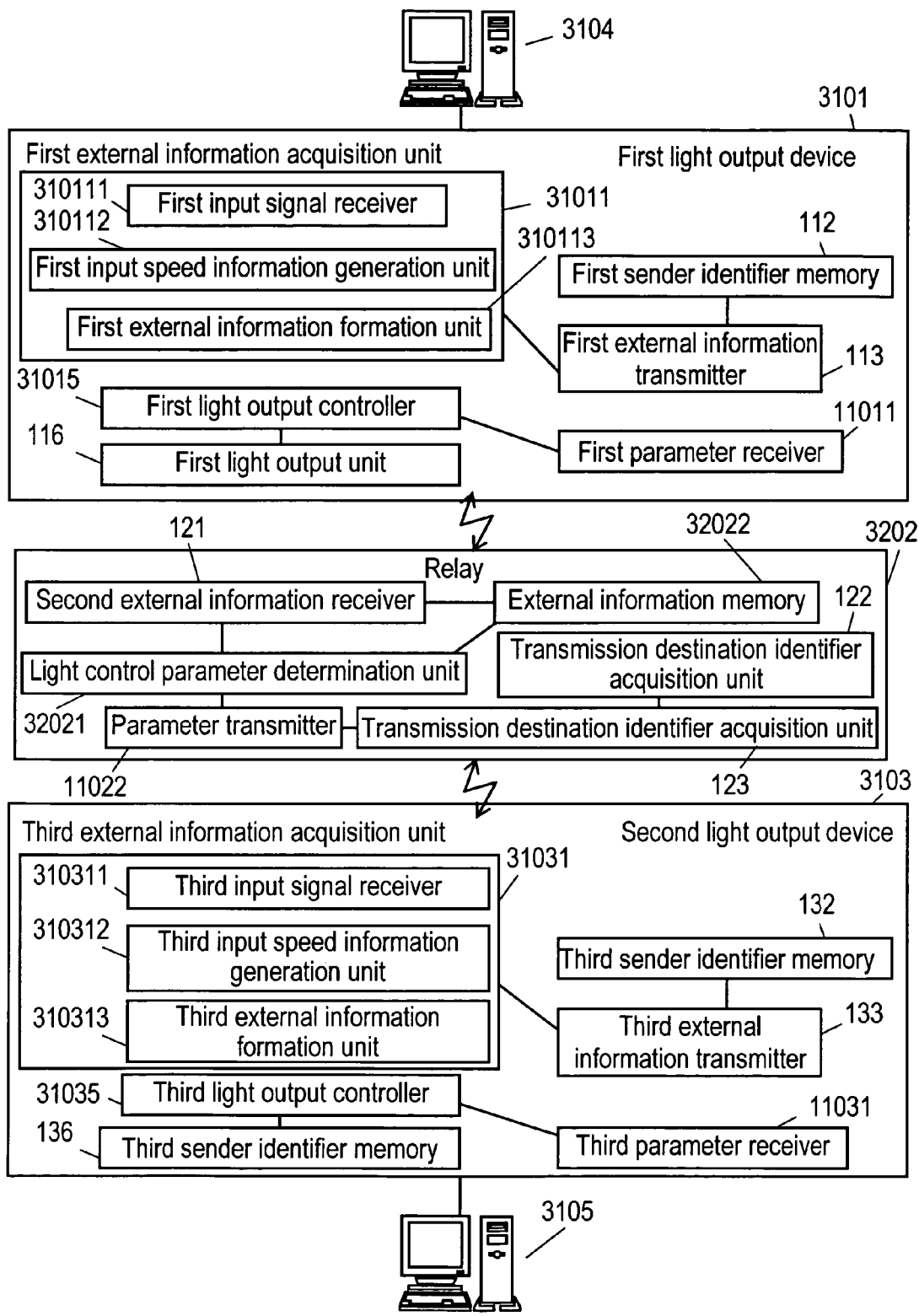
FIG. 32 is a block diagram of an information processing system in the fifth embodiment.

FIG. 32 is a block diagram of an information processing system, which includes first light output device 3101, relay 12 and second light output device 3103, etc.

First light output device 3101 includes first external information acquisition unit 31011, first sender identifier memory 112, first external information transmitter 113, first parameter receiver 11011, first light output controller 31015 and first light output unit 116.

First external information acquisition unit 31011 includes first input signal receiver 310111, first input speed information generation unit 310112 and first external information formation unit 310113.

First input signal receiver 310111 receives input signal.

The input signal in the present embodiment is a signal which is generated at first information processing terminal 3104 as the result of data input operation through a keyboard or the like data input apparatus.

In a case where first information processing terminal 3104 is a portable telephone unit, the input signal is a signal which is generated by a pressed input key.

First input signal receiver 310111 is formed, for example, with an electronic circuit having a bus electrically connected with first information processing terminal 3104 and software, or a dedicated circuit, which acquires an input signal transmitted via the bus.

First input speed information generation unit 310112 generates an input speed information from an input signal received at first input signal receiver 310111. First input speed information generation unit 310112 is implemented normally with software, but a dedicated circuit (hardware) may be used instead for the purpose.

First external information formation unit 310113 forms an external information which contains the input speed information generated at first input speed information generation unit 310112. In some cases, the external information and the input speed information can be the same data. In such a case, first external information formation unit 310113 does not do anything, i.e. the unit 310113 is in the "No Operation (NOP)" state.

First light output controller 31015 instructs first light output unit 116 to output the light in accordance with a group of light control parameters received at first parameter receiver 11011. The group of light control parameters means one or more number of light control parameters to be described below.

The group of light control parameters is an information generated from one or more number of sets of external information acquired at first light output device 3101 and transmitted from second light output device 3103; and represents the history in the relationship of external information with first light output device 3101 and second light output device 3103.

Relay 3202 includes second external information receiver 121, transmission control information memory 122, transmission destination identifier acquisition unit 123, light control parameter determination unit 32021, parameter transmitter 11022 and external information memory 32022.

External information memory 32022 stores a group of external information received at second external information receiver 121.

The group of external information in the present embodiment refers to the information formed of a set of the external information at first light output device 3101 and the external information at second light output device 3103. In the present embodiment, the external information group's history information is stored. The history information means a hoard of external information groups received time-sequentially. The group of external information is stored in a recording medium not shown in the drawing. The recording medium is in, for example, external information memory 32022. The recording medium may either be a non-volatile memory such as a hard disk, a semiconductor memory, or a volatile memory device. External information memory 32022 is implemented normally with software for storing information, but a dedicated circuit (hardware) may be used instead for the purpose.

Light control parameter determination unit 32021 determines a light control parameter group based on one or more number of sets of external information group (set of external information sent from respective first light output device 3101 and second light output device 3103) stored in external information memory 32022 or/and a set of external information group received at second external information receiver 121. Therefore, light control parameter determination unit 32021 determines a light control parameter group, which is a control parameter for visualizing one or more number of sets of received external information with respect to the history.

Second light output device 3103 includes third external information acquisition unit 31031, third sender identifier memory 132, third external information transmitter 133, third parameter receiver 11031, third light output controller 31035 and third light output unit 136. Third external information acquisition unit 31031, third sender identifier memory 132, third external information transmitter 133, third parameter receiver 11031, third light output controller 31035, third light output unit 136 performs identical functions, respectively, to those of first external information acquisition unit 31011, first sender identifier memory 112, first external information transmitter 113, first parameter receiver 11011, first light output controller 11015, first light output unit 116. Therefore, the description on these is eliminated here.

Third external information acquisition unit 31031 includes third input signal receiver 310311, third input speed information generation unit 310312 and third external information formation unit 310313.

Now in the following, the operation of an information processing system in the present embodiment is described with reference to a flow chart. In the first place, the operation of first light output device 3101 is described referring to FIG. 33, a flow chart.

(Step S3301) Timer (not shown) is set to 0. The timer counts up irrespective of the processing conducted at first light output device 3101.

(Step S3302) First input signal receiver 310111 judges if an input signal is received, or not. If there is an input signal, it is accumulated in a queue not shown in the drawing. First input signal receiver 310111 regularly visits the queue to see if there is such data in the queue. If there is an input signal received, it proceeds to S3303; if not received, it skips to S3304.

(Step S3303) First input signal receiver 310111 acquires all the input signals received during a certain specific period. Describing practically, first input signal receiver 310111 acquires the entire data in the queue, making the queue empty. First input signal receiver 310111 may only count the number of data in the queue.

(Step S3305) First input speed information generation unit 310112 generates the input speed information based on the data, or the data counts, acquired at S3303.

(Step S3306) First external information transmitter 113 acquires a sender identifier from first sender identifier memory 112.

(Step S3307) First external information transmitter 113 acquires a relay identifier for identifying relay 3202. The relay identifier is supposed to have been stored in a memory not shown in the drawing. The relay identifier is the information for communicating with a relay; it is, for example, an IP address.

(Step S3308) First external information transmitter 113 transmits external information and sender identifier to relay 3202 identified by the relay identifier.

(Step S3309) First light output device waits until a separately-counting timer reaches a certain predetermined value (n).

(Step S3310) First light output device judges whether a finish signal is received, or not. If yes, it is finished; if not received, it proceeds to S3311.

(Step S3311) First light output device judges whether first parameter receiver 11011 received a light control parameter group, or not. If received, it proceeds to S3312; if not received, it repeats S3311.

(Step S3312) First light output controller 31015 instructs first light output unit 116 to output the light based on the control parameter group received at S3311.

(Step S3313) First light output unit 116 outputs the light in accordance with instruction of first light output controller 31015.

Figure 33:
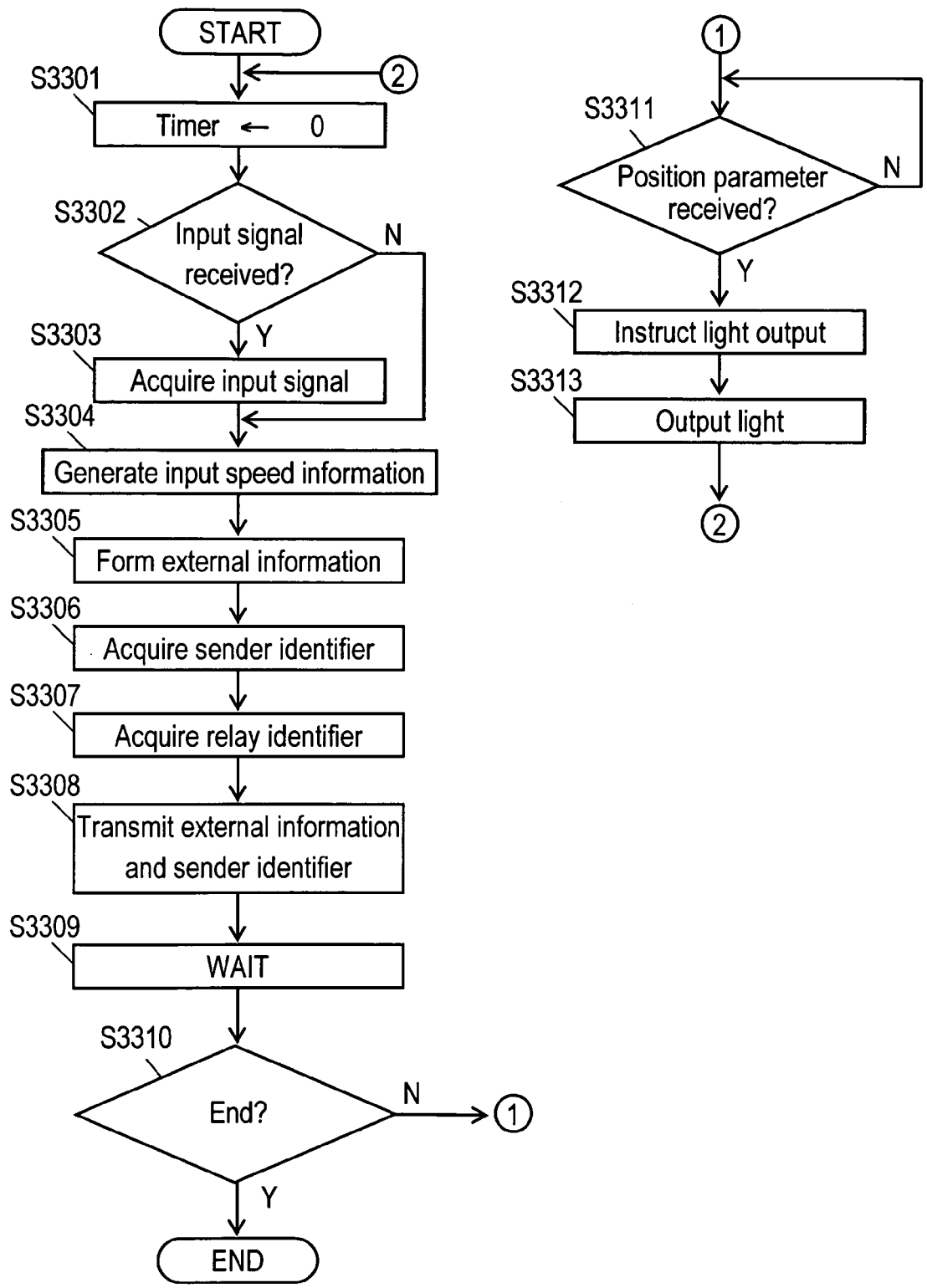
FIG. 33 is a flow chart used to describe the operation of a light output device in the fifth embodiment.

In the flow chart, FIG. 33, the acquisition of external information (processing at S3301 and afterwards) is performed without having any triggering. However, the operation may be started after having a trigger from a user of first light output device 3101 pressing a start button, for example. Or, the external information acquisition at S3301 and afterwards may be started upon receiving a triggering signal from light output device 2803, relay 12 or other devices.

Figure 34:
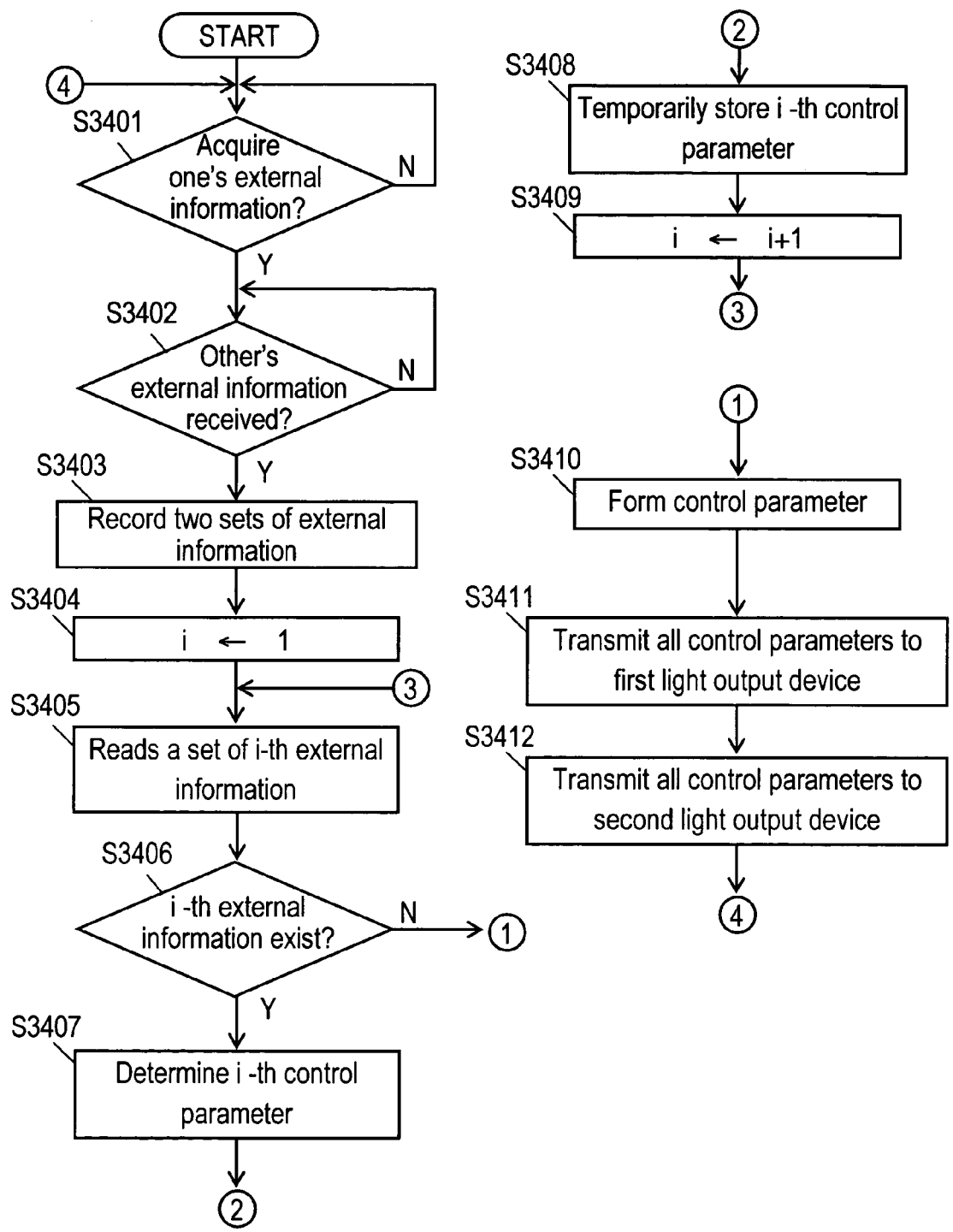
FIG. 34 is a flow chart used to describe the operation of a relay in the fifth embodiment.

Next, the operation of relay 3202 is described referring a flow chart, FIG. 34.

(Step S3401) Second external information receiver 121 judges whether external information and a sender identifier are received from first light output device 3101. If received, it proceeds to S3402; if not received, it repeats S3401.

(Step S3402) Second external information receiver 121 judges whether external information and a sender identifier are received from second light output device 3103. If received, it proceeds to S3403; if not received, it repeats S3402.

(Step S3403) External information memory 32022 records two pieces of external information (external information group) received at second external information receiver 121.

(Step S3404) Counter "i" is replaced with 1.

(Step S3405) Light control parameter determination unit 32021 reads a set of i-th order external information out of a memory medium stored in external information memory 32022.

(Step S3406) Light control parameter determination unit 32021 judges whether there is a set of external information at the i-th order, or not. If yes, it proceeds to S3407; if no such external information set exists, it skips to S3410.

(Step S3407) Light control parameter determination unit 32021 determines the i-th light control parameter based on the i-th external information set.

(Step S3408) Light control parameter determination unit 32021 temporarily stores (shunts) the i-th light control parameter determined at S3407.

(Step S3409) Counter "i" is incremented by 1.

(Step S3410) Light control parameter determination unit 32021 forms a transmitting control parameter group out of the temporarily stored entire control parameters.

(Step S3411) Parameter transmitter 11022 transmits the control parameter group formed at S3410 to first light output device 3101.

(Step S3412) Parameter transmitter 11022 transmits the control parameter group formed at S3410 to second light output device 3103. It returns to S3401.

Although relay 3202 in the flow chart, FIG. 31, simply awaits a reception of external information, relay 3202 may ask directly, or indirectly, first light output device 3101 and second light output device 3103 for transmission of external information.

Although light control parameter determination unit 32021 in the flow chart, FIG. 31, determines a light control parameter group based on one or more sets of external information recorded in external information memory, the light control parameter group may be determined based on one or more sets of external information recorded in the external information memory and the external information received at the second external information receiver. That is, the timing of recording the external information in the external information memory may be either before or after a light control parameter group is transmitted.

Next, the operation of an information processing system in the present embodiment and other items are described practically.

Suppose, the history (history information) of external information set as shown in FIG. 35 is stored in an external information memory. The history information is formed of a record containing the time when external information is received from the two light output devices, and the external information from the first light output device and the external information from the second light output device. The external information from the first light output device and the external information from the second light output device are represented by the number of letters acquired by the respective light output devices, inputted through the keyboards of the respective information processing terminals within 5 min.

Light control parameter determination unit determines a light control parameter based on the table shown in FIG. 36. That is, when there is a difference of more than 200 between the first light output device and the second light output device in their external information, then the light control parameter is "0". Likewise, when the difference is "0-9", then the light control parameter is "20". The value of light control parameter here indicates a voltage to be applied on the light output devices at their respective light output units.

Reference is made to FIG. 35 and FIG. 36; since a difference in the external information at "9:00 o'clock" is "1", the control parameter is "20". The difference at "9:05" is "10", so the control parameter is "15"; the difference at "9:10" is "410", so the control parameter is "0".

Accordingly, a light control parameter group transmitted to respective light output deices from relay is "20, 15, 0 . . . ".

Figure 37:
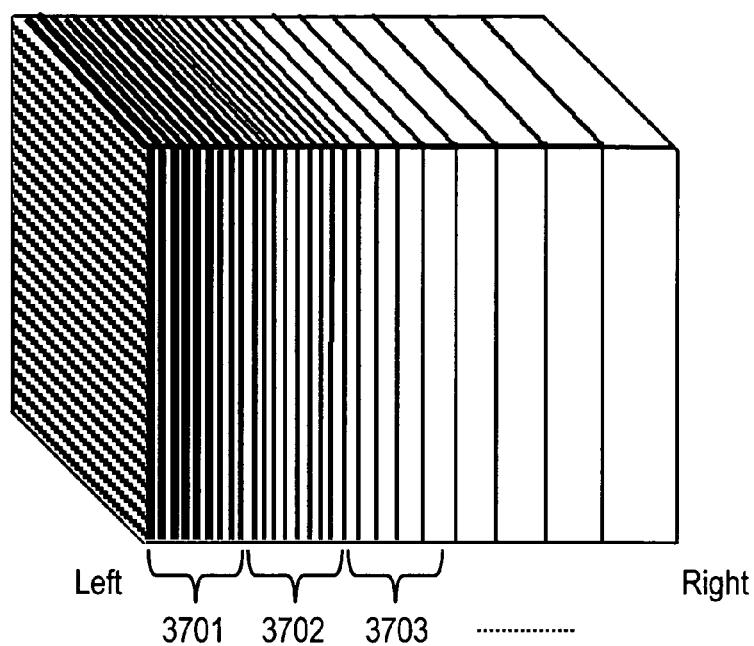
FIG. 37 illustrates how a light output device in the fifth embodiment outputs the light.

Upon receiving the light control parameter, a light output device outputs the light in a style as shown in FIG. 37, for example. That is, reaction to the "9:00" control parameter is exhibited in the leftmost region 3701, and reactions to the "9:05" and the subsequent control parameters are exhibited consecutively in the regions in the right, 3702, 3703 . . . .

Figure 38:
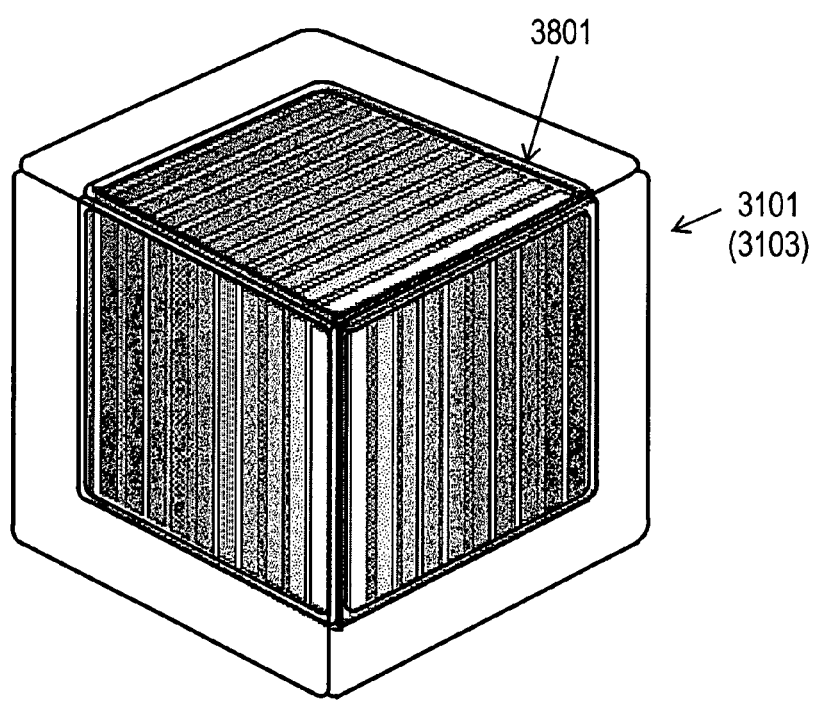
FIG. 38 shows an exemplary structure of a light output device in the fifth embodiment.

The above-described light outputting based on the history information can be implemented on, for example, liquid crystal display 3801 disposed on the six faces of cubic shaped light output device 3101, 3103, as shown in FIG. 38. That is, the six light output units of a light output device are formed with displays (e.g. liquid crystal display), as shown in FIG. 38. In this way, the intensity of the light output can be exhibited with an obscure graduation as shown in FIG. 37.

Figure 39:
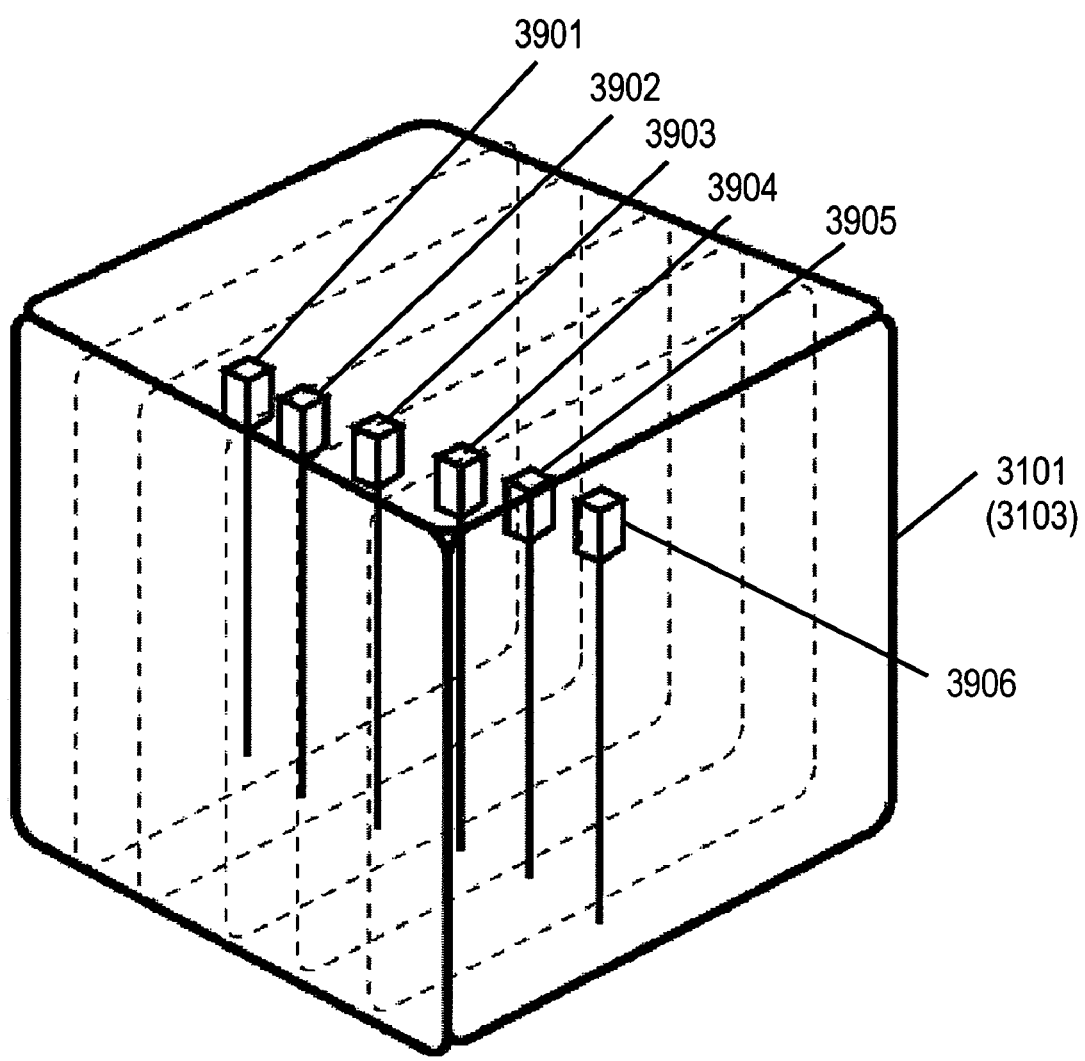
FIG. 39 shows an exemplary structure of a light output device in the fifth embodiment.

The light output unit of light output device may be structured in a configuration as shown in FIG. 39.

Referring to FIG. 39, cube 3101, 3103 is separated by partitions at a certain interval; in each of the partitioned spaces, an LED is disposed, from 3901 to 3906 respectively. Each of the LEDs is controlled in the light intensity by a light output controller based on history information. Describing practically, light intensity of the leftmost LED 3901 is determined based on the latest external information. LEDs 3902 through 3906 output, respectively, the light based on the second latest information through the sixth latest information. If a number of pieces of the external information to be handled is "n" (an integer), then the LED may be provided for n pieces. The light in a space is shielded by the partitions so that it does not leak to the neighboring spaces.

As described in the above, information on the data input speed from an input apparatus of information processing terminal is continuously sent to a relay from respective light output devices, in the present embodiment. The relay determines a light control parameter based on the data input speed transmitted from two or more light output devices. Respective light output devices emit an obscure light based on the relevant light control parameter. In this way, the state of things about business is communicated in a soft mood among the users of respective light output devices.

For example, in a case where people using respective information processing terminals are engaged in a cooperative assignment, the light output devices output the light vigorously when performing data input. Thereby, it can encourage them to perform the cooperative assignments.

The above described is just an exemplary usage of a light output device in the present embodiment. The people engaged in a cooperative assignment are not the only users of the present information processing system.

Although the information on input speed is continuously conveyed in the present embodiment for outputting the light, the light may be outputted instead based on a single input speed value. In the latter case, external information memory 32022 in relay 3203 is eliminated.

In the present embodiment, the light output device converted the information on data input into an input speed information. However, the conversion may be performed at the relay. That is, a light output device acquires a data input signal, and transmits the signal to a relay. The relay receives a plurality of data input signal, and calculates a number of signals per unit time, for converting it into the input speed information. In this configuration, a light output device may simply transmit an input signal as it is to the relay. Accordingly, structure of the light output device can be simplified.

Although the external information memory in the present embodiment has been structured as a part of the relay, the memory may be provided in the light output device. In the latter case, the light output device outputs the light in accordance with the history information stored in the external information memory.

Embodiment 6

Figure 40:
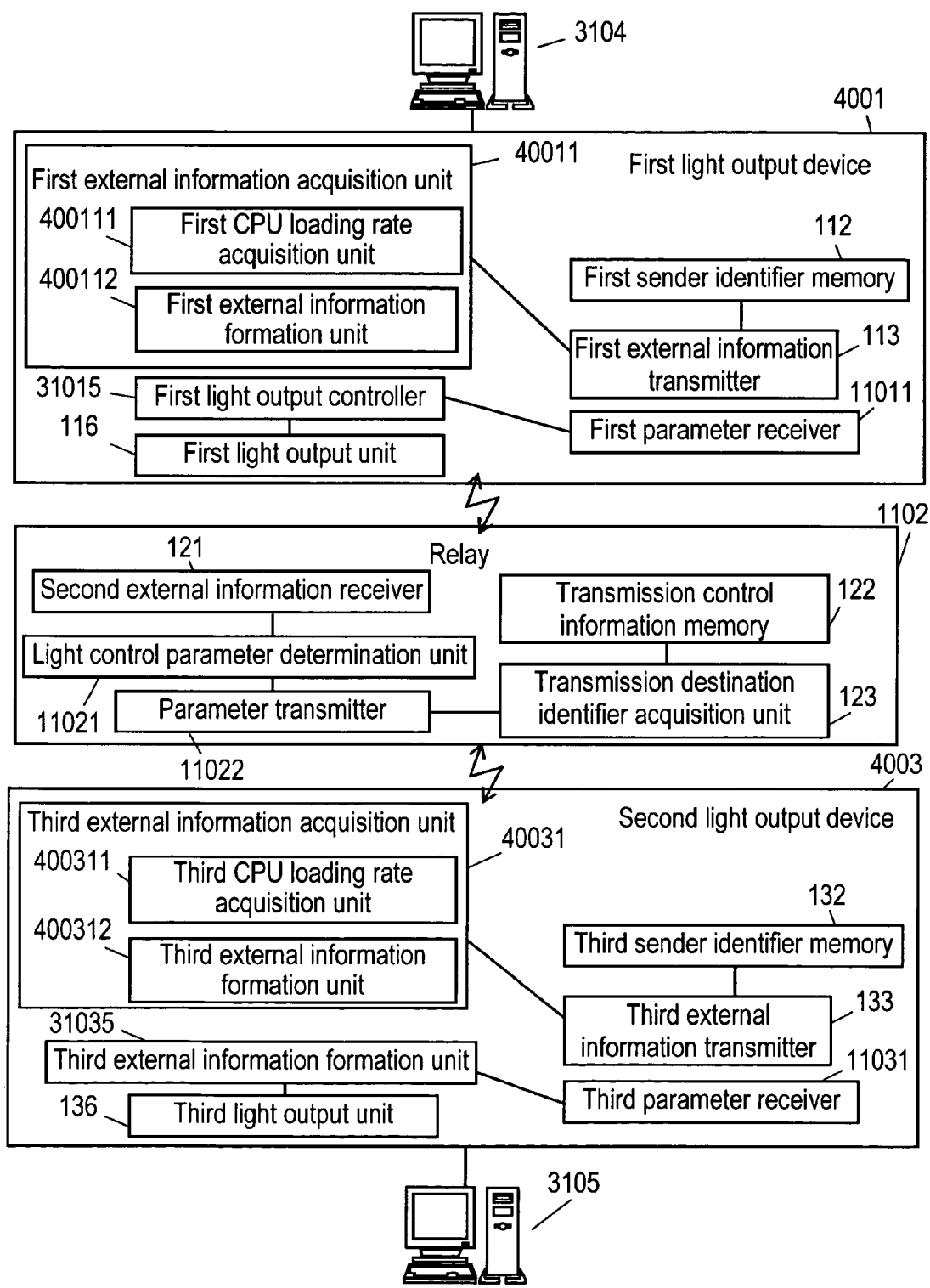
FIG. 40 is a block diagram of an information processing system in a sixth exemplary embodiment.

FIG. 40 is a block diagram showing an information processing system in the present embodiment.

The present information processing system includes first light output device 4001, relay 1102, second light output device 4003, first information processing terminal 3104 and second information processing terminal 3105.

First light output device 4001 includes first external information acquisition unit 40011, first sender identifier memory 112, first external information transmitter 113, first parameter receiver 11011, first light output controller 31015 and first light output unit 116.

First external information acquisition unit 40011 includes first CPU loading rate acquisition unit 400111, and first external information formation unit 400112.

First CPU loading rate acquisition unit 400111 acquires a loading rate of first information processing terminal 3104's CPU. The CPU loading rate is exhibited normally in terms of numerals, from 0 (%) to 100 (%). Since the technology for acquiring CPU loading rate is a known technology contained in a readily available OS, detailed description on which is eliminated here.

First CPU loading rate acquisition unit 400111 is implemented normally with software, but hardware may be used instead for the purpose. What is in mind for information processing terminal 3104 is an electric apparatus containing a CPU. The typical information processing terminal 3104 is a computer. However, it can be a microwave oven, a TV receiver, a portable telephone unit, a game machine or the like electric appliances.

First external information formation unit 400112 forms external information from the CPU loading rate acquired at first CPU loading rate acquisition unit 400111. First external information formation unit 400112 is formed normally with software, but hardware may be used instead for the purpose.

Figure 41:
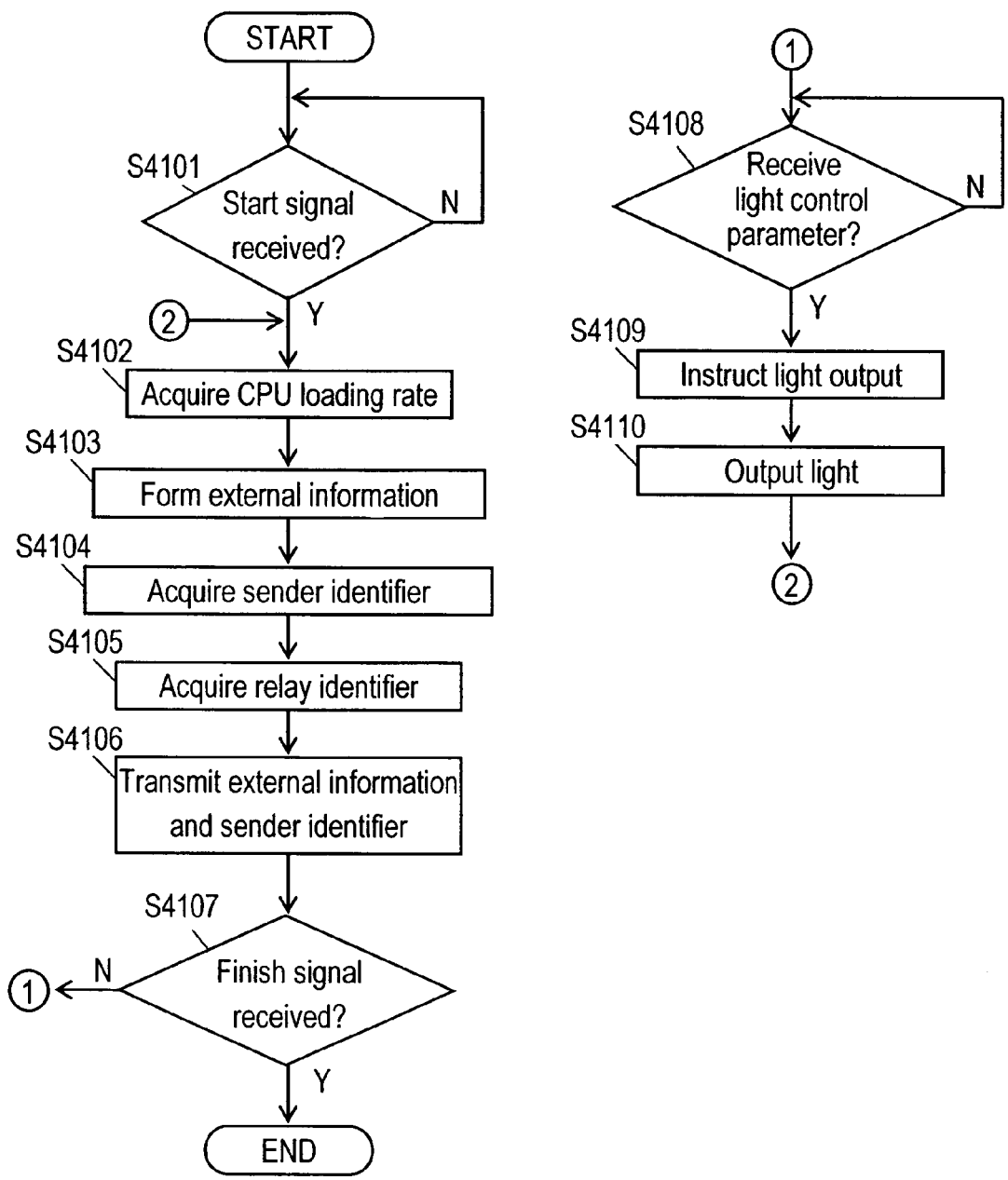
FIG. 41 is a flow chart used to describe the operation of a light output device in the sixth embodiment.

Now, the operation of first light output device 4001, which is a constituent item of the present information processing system, is described with reference to FIG. 41, a flow chart.

(Step S4101) First external information acquisition unit 40011 judges if a start signal for starting a process of forming and transmitting an external information is received, or not. If the start signal is received, it proceeds to S4102; if not received, it repeats S4101. A start signal may be generated by a user pressing a start button, or the signal may be transmitted from an external source (e.g. relay 1102, or the like unit).

(Step S4102) First CPU loading rate acquisition unit 400111 acquires first information processing terminal 3104's CPU loading rate.

(Step S4103) First external information formation unit 400112 forms external information from the CPU loading rate acquired at S4102.

(Step S4104) First external information transmitter 113 acquires a sender identifier from first sender identifier memory 112.

(Step S4105) First external information transmitter 113 acquires a relay identifier which is an information for identifying a relay. The relay identifier is supposed to have been stored in a memory not shown in the drawing.

(Step S4106) First external information transmitter 113 transmits external information and a sender identifier to a relay identified by the relay identifier.

(Step S4107) Whether a finish signal is received, or not, is judged. If yes, it ends; if not received, it proceeds to S4108.

(Step S4108) Whether first parameter receiver 11011 received a light control parameter, or not, is judged. If yes, it proceeds to S4109; if not received, it repeats S4108.

(Step S4109) First light output controller 11015 instructs first light output unit 116 to output the light based on the control parameter received at S4108.

(Step S4110) First light output unit 116 outputs the light in accordance with instruction of first light output controller 11015.

Since relay 1102 has the same structure as that in embodiment 4 and operates in the same manner as in embodiment 4, description on these points are eliminated here.

Since second light output device 4003 operates in the same manner as first light output device 4001, the description on it is eliminated here.

As described in the above, respective light output devices in the present embodiment output the light in accordance with a light control parameter generated based on the first light output device's CPU loading rate and the second light output device's CPU loading rate. In this way, a simulated relationship (variance, aggregate, or whatever) of the state of things in business between the first information processing terminal's user and the second information processing terminal's user is communicated in a soft mood among respective holders of the light output devices. Thus, the system would make a contribution in raising the work efficiency, or motivate the people engaged in a cooperative work higher.

An interface to acquire a CPU loading rate has been made public by normal information processing devices (computer, OS). Therefore, it can be implemented with a simpler structure as compared with that in embodiment 5, where the data input speed was acquired through a keyboard or other input apparatus. That is, since the CPU loading rate is the information which represents a simulated state of things of business, it can communicate a simulated relationship (variance, aggregate, or whatever) of the state of things between the first information processing terminal's user and the second information processing terminal's user in a soft mood, with a simpler structure.

In the present embodiment, light output device changes in the light output level at each time when the light output device receives one piece of information on the CPU loading rate. Instead, the information on CPU loading rate is communicated continuously, and the light output level may be changed based on the plurality of pieces of information on CPU loading rate (history information). That is, the input speed used in embodiment 5 may be used in place of the CPU loading rate. The particulars about the structure and the processing in this case have already been described in embodiment 5. That is, the relay in this case needs to be provided with an external information memory.

In the present embodiment, a light control parameter is determined by the relay. As described earlier in embodiment 2, a relay may simply transmit the external information of each of light output devices to the other light output device, leaving determination of the light control parameter to each light output device. This statement applies likewise also in other embodiments.

Embodiment 7

Figure 42:
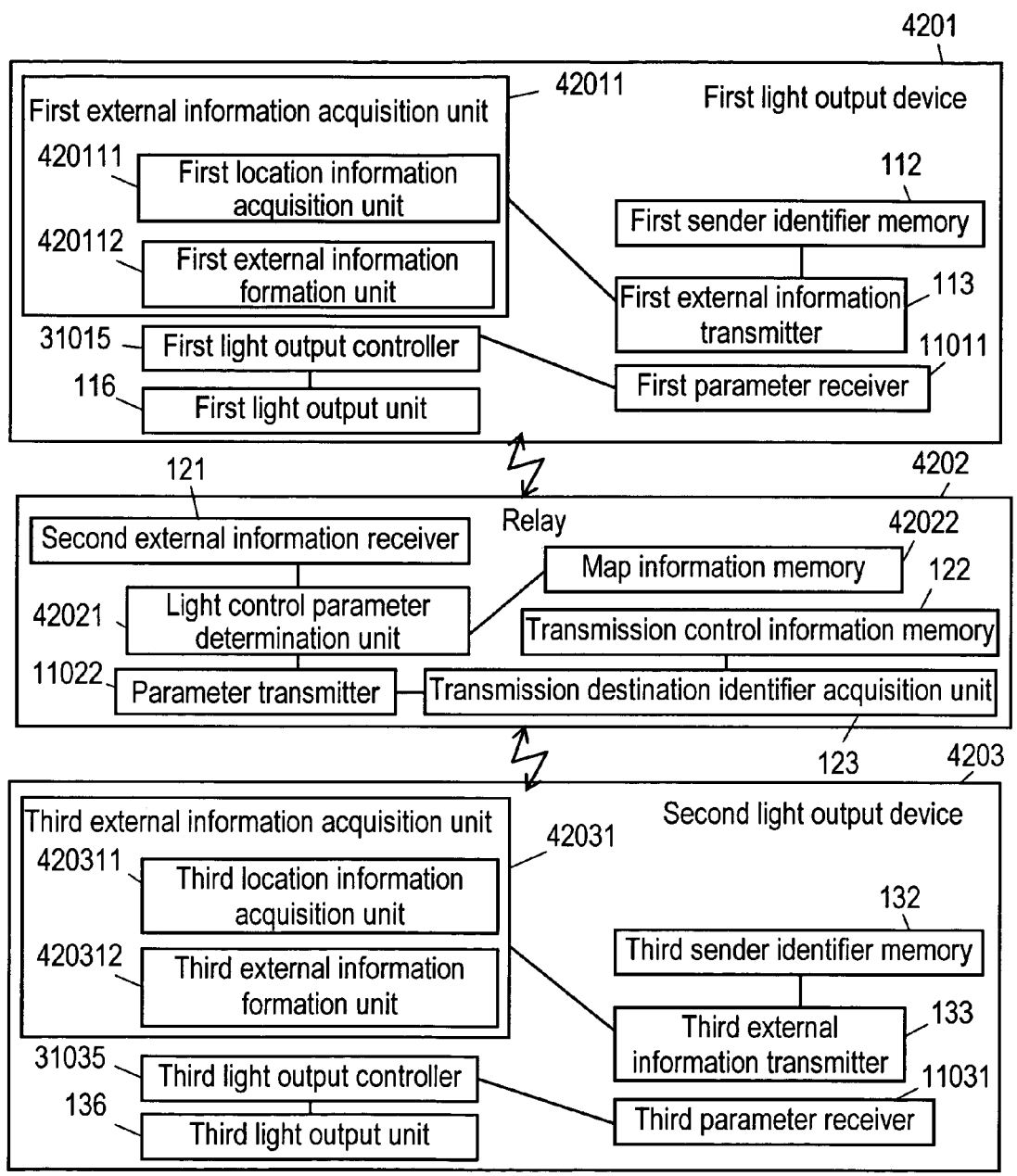
FIG. 42 is a block diagram of an information processing system in a seventh exemplary embodiment.

FIG. 42 is a block diagram showing an information processing system in accordance with the present embodiment.

The information processing system is formed of first light output device 4201, relay 4202 and second light output device 4203.

First light output device 4201 includes first external information acquisition unit 42011, first sender identifier memory 112, first external information transmitter 113, first parameter receiver 11011, first light output controller 31015 and first light output unit 116.

First external information acquisition unit 42011 includes first location information acquisition unit 420111 and first external information formation unit 420112.

First location information acquisition unit 420111 acquires a location information which is an information about a place of first light output device 4201. First location information acquisition unit 420111 is implemented with, for example, a wireless apparatus for receiving a signal from RFID tag in which location information is stored. First location information acquisition unit 420111 may be formed instead with any other apparatus in so far as it is capable of acquiring location information. A possible apparatus for the purpose is, for example, a Bluetooth wireless communication apparatus that can acquire location information.

First external information formation unit 420112 forms the external information from the location information acquired at first location information acquisition unit 420111. First external information formation unit 420112 is implemented normally with software; but hardware may be used instead for the purpose.

Relay 4202 includes second external information receiver 121, transmission control information memory 122, transmission destination identifier acquisition unit 123, light control parameter determination unit 42021, parameter transmitter 11022 and map information memory 42022.

Map information memory 42022 stores map information which is information about a map. Map information memory 42022 can be implemented normally with a nonvolatile memory such as a hard disk, an optical disk, etc. However, a volatile memory may be used instead for the purpose.

Light control parameter determination unit 42021 determines a light control parameter based on two pieces of external information (location information) received at second external information receiver 121 and the map information stored in map information memory 42022.

The determination of light control parameter is made in accordance with the algolism described below.

Light control parameter determination unit 42021 calculates a distance between first light output device 4201 and second light output device 4203 by referring the location information of first light output device 4201 and the location information second light output device 4203 to the map information stored in map information memory 42022. The inverse number of the distance multiplied by n ("n/distance") is used for the light control parameter. Light control parameter determination unit 42021 is implemented normally with software, but hardware may be used instead for the purpose.

Since second light output device 4203 has the same structure as first light output device 4201, description on each of the constituent elements is eliminated here.

Figure 43:
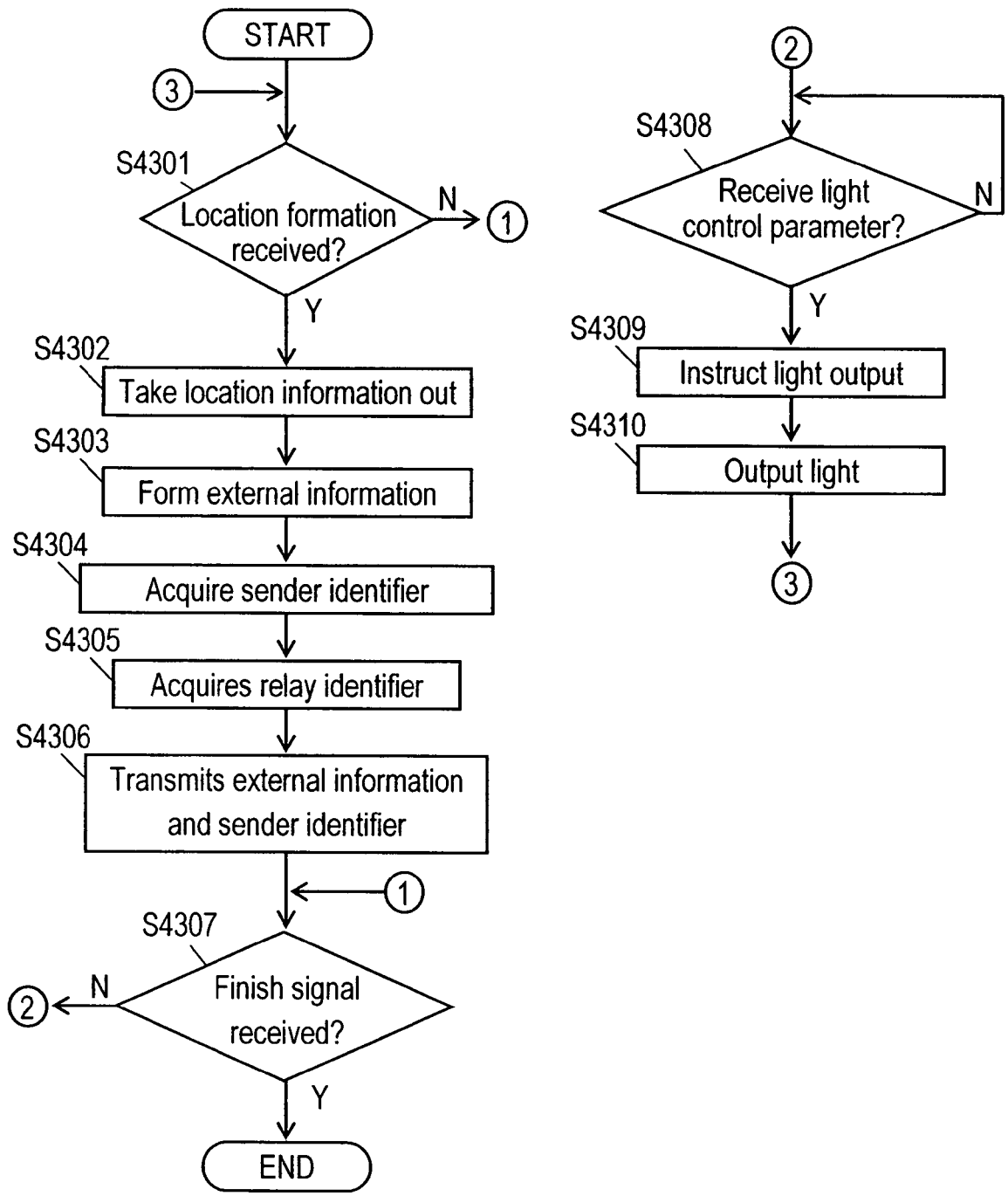
FIG. 43 is a flow chart used to describe the operation of a light output device in the seventh embodiment.

Now, the operation of the present information processing system is described. In the first place, the operation of light output device 4201 is described with reference to FIG. 43, a flow chart.

(Step S4301) First location information acquisition unit 420111 judges if a signal containing location formation is received, or not. If yes, it proceeds to S4302; if not received, it skips to S4307.

(Step S4302) First location information acquisition unit 420111 takes the location information out of the signal received at S4301.

(Step S4303) First external information formation unit 420112 forms external information from the location information acquired at S4302.

(Step S4304) First external information transmitter 113 acquires a sender identifier from first sender identifier memory 112.

(Step S4305) First external information transmitter 113 acquires a relay identifier, which is the information for identifying a relay. The relay identifier is supposed to have been stored in a memory not shown in the drawing.

(Step S4306) First external information transmitter 113 transmits external information and sender identifier to a relay identified by the relay identifier.

(Step S4307) First light output device 4201 judges whether a finish signal is received, or not. If yes, it is finished; if not received, it proceeds to S4308.

(Step S4308) First light output device 4201 judges whether first parameter receiver 11011 received a light control parameter, or not. If yes, it proceeds to S4309; if not received, it repeats S4308.

(Step S4309) First light output controller 31015 instructs first light output unit 116 to output the light based on the control parameter received at S4308.

(Step S4310) First light output unit 116 outputs the light in accordance with instruction of first light output controller 31015.

Figure 44:
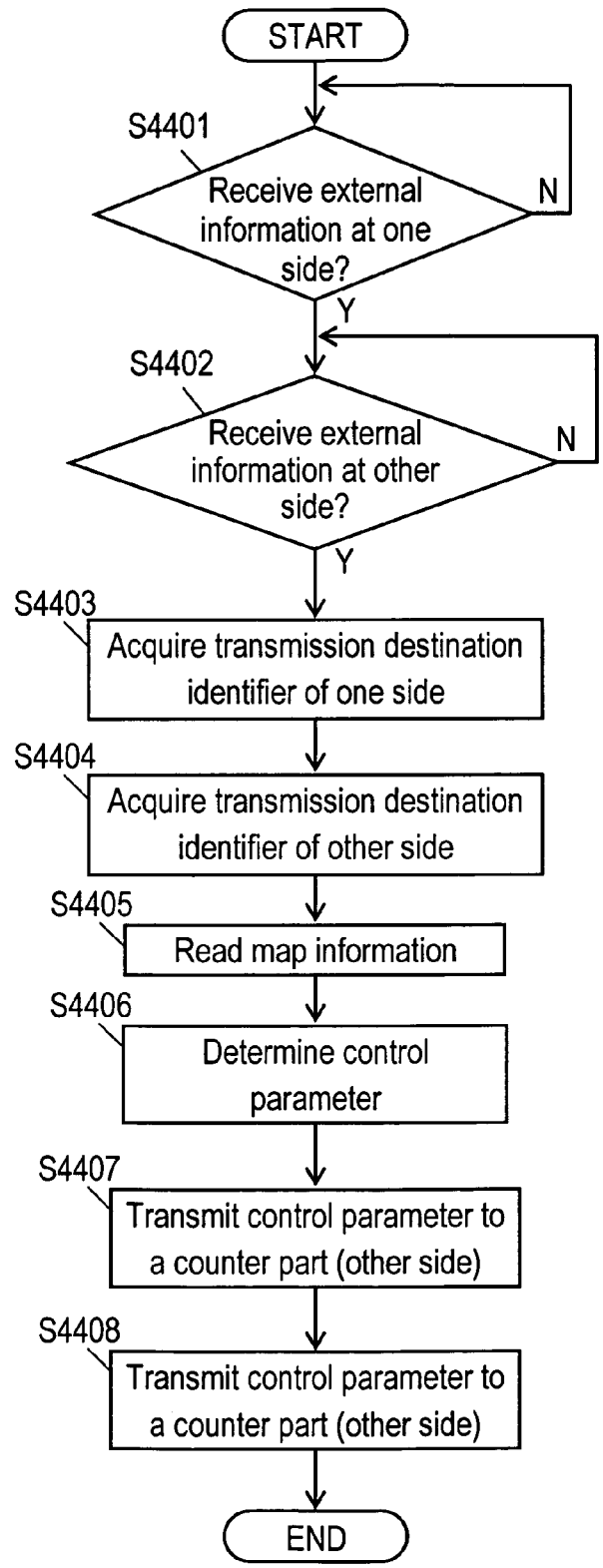
FIG. 44 is a flow chart used to describe the operation of a relay in the seventh embodiment.

Next, the operation of relay 1102 is described referring to FIG. 44, a flow chart.

(Step S4401) Second external information receiver 121 judges whether external information and a sender identifier are received from first light output device 4201. If yes, it proceeds to S4402; if not received, it repeats S4401.

(Step S4402) Second external information receiver 121 judges whether external information and a sender identifier are received from second light output device 4203. If yes, it proceeds to S4403; if not received, it repeats S4402.

(Step S4403) Transmission destination identifier acquisition unit 123 acquires from transmission control information memory a transmission destination identifier, which is a counterpart of the sender identifier received at S4401.

(Step S4404) Transmission destination identifier acquisition unit 123 acquires from transmission control information memory a transmission destination identifier, which is a counterpart of the sender identifier received at S4402.

(Step S4405) Light control parameter determination unit 11021 reads map information out of map information memory 32022.

(Step S4406) Light control parameter determination unit 11021 determines a light control parameter based on the map information read at S4405 and external information acquired at S4401, S4402.

(Step S4407) The light control parameter determined at S4406 is transmitted to one party (the transmission destination indicated by the transmission destination identifier acquired at S4403).

(Step S4408) The light control parameter determined at S4406 is transmitted to the other party (the transmission destination indicated by the transmission destination identifier acquired at S4404).

In the flow chart, FIG. 44, the relay transmits a light control parameter when it is triggered by the reception of the external information; however, it may transmit the light control parameter upon receiving an access demand from second light output device 4203 or first light output device 4201. Or, the relay may transmit the light control parameter without having any triggering.

Next, the operation of an information processing system in the present embodiment is described practically.

Suppose the light output device is a portable telephone unit compatible with the RFID tag information.

When a train running on route X 4505 of ABC Railways Company makes a brief stop at a station, an information processor (not shown) installed on the platform transmits a station identifier, which is the information for identifying the station, to RFID tag within the train. Furthermore, the portable telephone unit is supposed to read the information out of the RFID tag located within the train.

The station identifier here is information, e.g. "station A". As shown in FIG. 45, a first person bearing a first light output device is on board train 4502, which train has left station A and running for station B. On the other hand, a second person bearing a second light output device is on board train 4503, which train has left station E and running for station D. Suppose respective persons arrived at station B and station D. Relay 4202 stores "ABC Railways' Table of Distance, Route X" 4601, as shown in FIG. 46, in map information memory 42022. The Table of Distance contains a plurality of pieces of information about "station identifier" and "distance from the starting station identifier".

In the above occasion, the location information "station B" contained in the external information is transmitted from first light output device 4201 to relay 4202; and, "station D" is transmitted from second light output device 4203 to the relay. Relay 4202's light control parameter determination unit 42021 calculates a distance between the first light output device and the second light output device, based on the table in FIG. 46 and the station identifiers, "station B" and "station D".

According to table 4601, FIG. 46, a distance between the stations is "5.1 km". The light control parameter determination unit determines a light control parameter using the distance "5.1 km". Suppose the light control parameter determination unit determines a light control parameter using a formula "100/distance (max. 30 and it is also 30 when the distance is 0)". Then, the light control parameter is "100/5.1=approximately 19.6". The relay transmits the light control parameter "19.6" to the first light output device and the second light output device.

The first light output device and the second light output device emit the light in accordance with the received light control parameter "19.6". The light control parameter here represents a voltage. Accordingly, the greater is the light control parameter, the brighter are the lights from the first light output device and the second light output device. That is, the closer are the persons bearing first light output device and second light output device, the brighter are the light output devices.

The light may of course be controlled in different ways. In a case where first light output device 4201 and second light output device 4203 are provided with the function of, for example, portable telephone, as shown in FIG. 47, and each of the telephone units is provided with liquid crystal display, 4204, 4205. In this exemplary case, the wall paper color of liquid crystal display turns to be warmer along with an increasing value of light control parameter, while the color goes colder when the value of light control parameter goes smaller. That is, when the first light output device and the second light output device are getting closer to each other, the light shifts from deep blue color towards bright red color.

In the present embodiment, a light control parameter changes based on the first light output device's location information and the second light output's location information, and a relative relationship between the first light output device's location information and the second light output device's location information is exhibited at respective devices by means of light in a soft mood.

Although a first light output device and a second light output device in the present embodiment are provided, respectively, with single light output means, respective light output devices may have two or more number of light output means. Method of controlling the two or more number of light output means has already been described in detail in the earlier embodiment.

Although a processing for acquiring the distance information from the location information, in the present embodiment, is performed at a relay, the processing may be conducted at respective light output devices.

Furthermore, if a relay receives a plurality of pieces of information from two or more number of light output devices, one can observe whether the two light output devices are approaching closer to each other, or getting away from each other. By identifying whether the two light output devices are "getting closer to each other", or "getting away from each other", outputting of the light may be controlled based on the identification results. For example, the state of getting closer can be exhibited with a "warm color", while a "cold color" may be used for representing the state of moving away.

Furthermore, the light output may be controlled based on two pieces of information, viz. the distance and the change in the state ("approaching closer?/parting away?"). The light output may be controlled in the following manner, for example.

When two or more number of light output devices approach to be very close to each other, it emits a "pure red" color, while it emits a "pale red" color when they are approaching but the distance is not that short; when the light output devices are parting away from each other and the distance becomes long enough, a "deep blue" color is emitted, while a "pale blue" color is outputted when the light output devices are parting away but still close to each other.

Embodiment 8

Figure 48:
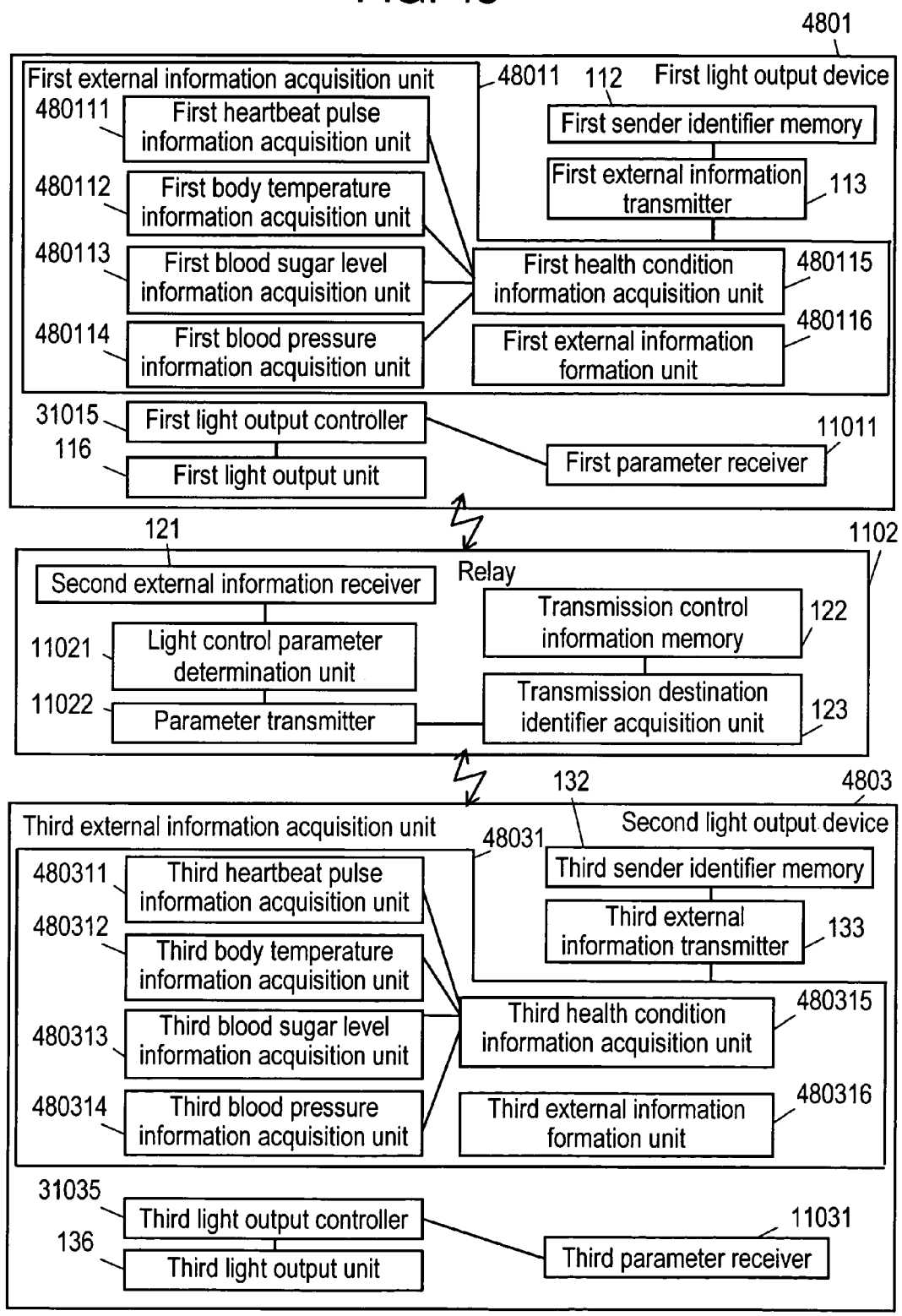
FIG. 48 is a block diagram of an information processing system in an eighth exemplary embodiment.

FIG. 48 is a block diagram showing an information processing system in the present embodiment.

The present information processing system is formed of first light output device 4801, relay 1102 and second light output device 4803.

First light output device 4801 includes first external information acquisition unit 48011, first sender identifier memory 112, first external information transmitter 113, first parameter receiver 11011, first light output controller 31015 and first light output unit 116.

First external information acquisition unit 48011 includes first heartbeat pulse information acquisition unit 480111, first body temperature information acquisition unit 480112, first blood sugar level information acquisition unit 480113, first blood pressure information acquisition unit 480114, first health condition information acquisition unit 480115 and first external information formation unit 480116.

First heartbeat pulse information acquisition unit 480111 acquires heartbeat pulse information which is the information on heartbeat pulse counts, first body temperature information acquisition unit 480112 acquires body temperature information which is the information on body temperature, first blood sugar level information acquisition unit 480113 acquires blood sugar level information which is the information on blood sugar level.

First blood pressure information acquisition unit 480114 acquires blood pressure information which is the information on blood pressure. These units for acquiring the heartbeat pulse information, body temperature information, blood sugar level information and blood pressure information can be implemented with an electronic health check apparatus, for example, readily available in the market. Technologies needed for obtaining the above information have been made known. Therefore, the description on the technologies for obtaining the information is eliminated here.

First health condition information acquisition unit 480115 generates health condition information, which represents overall health conditions based on the whole or a part of the information acquired at first heartbeat pulse information acquisition unit 480111, first body temperature information acquisition unit 480112, first blood sugar level information acquisition unit 480113, first blood pressure information acquisition unit 480114, etc.

First health condition information acquisition unit 480115 is implemented normally with software, but a dedicated circuit (hardware) may be used instead for the purpose.

First external information formation unit 480116 forms an external information to be transmitted to relay 1102, which external information is formed based on the whole or a part of the information acquired at first heartbeat pulse information acquisition unit 480111, first body temperature information acquisition unit 480112, first blood sugar level information acquisition unit 480113, first blood pressure information acquisition unit 480114 and first health condition information acquisition unit 480115.

First external information formation unit 480116 is implemented normally with software, but a dedicated circuit (hardware) may be used instead for the purpose.

Now, the operation of first light output device 4801 is described with reference to FIG. 49, a flow chart.

(Step S4901) First external information acquisition unit 48011 judges if an instruction for acquiring an external information is received, or not. If the instruction is inputted, it proceeds to S4902; if not received, it repeats S4901.

(Step S4902) First heartbeat pulse information acquisition unit 480111 acquires heartbeat pulse information.

(Step S4903) First body temperature information acquisition unit 480112 acquires body temperature information.

(Step S4904) First blood sugar level information acquisition unit 480113 acquires blood sugar level information.

(Step S4905) First blood pressure information acquisition unit 480114 acquires a blood pressure information.

(Step S4906) First health condition information acquisition unit 480115 generates health condition information based on the information acquired at the steps from S4902 through S4905.

(Step S4907) First external information formation unit 480116 forms external information based on information acquired at the steps from S4902 through S4906.

(Step S4908) First external information transmitter 113 acquires a sender identifier from first sender identifier memory 112.

(Step S4909) First external information transmitter 113 acquires a relay identifier which is the information for identifying a relay. The relay identifier is supposed to have been stored in a memory not shown in the drawing.

(Step S4910) First external information transmitter 113 transmits the external information and sender identifier to a relay identified by the relay identifier.

(Step S4911) First light output device 4801 judges if a finish signal is received, or not. If yes, it is finished; if not received, it proceeds to S4912.

(Step S4912) First parameter receiver 11011 judges whether a light control parameter is received, or not. If yes, it proceeds to S4913; if not, it repeats S4912.

(Step S4913) First light output controller 31015 instructs first light output unit 116 to output the light based on the control parameter received at S4912.

(Step S4914) First light output unit 116 outputs the light in accordance with the instruction from first light output controller 31015.

Figure 49:
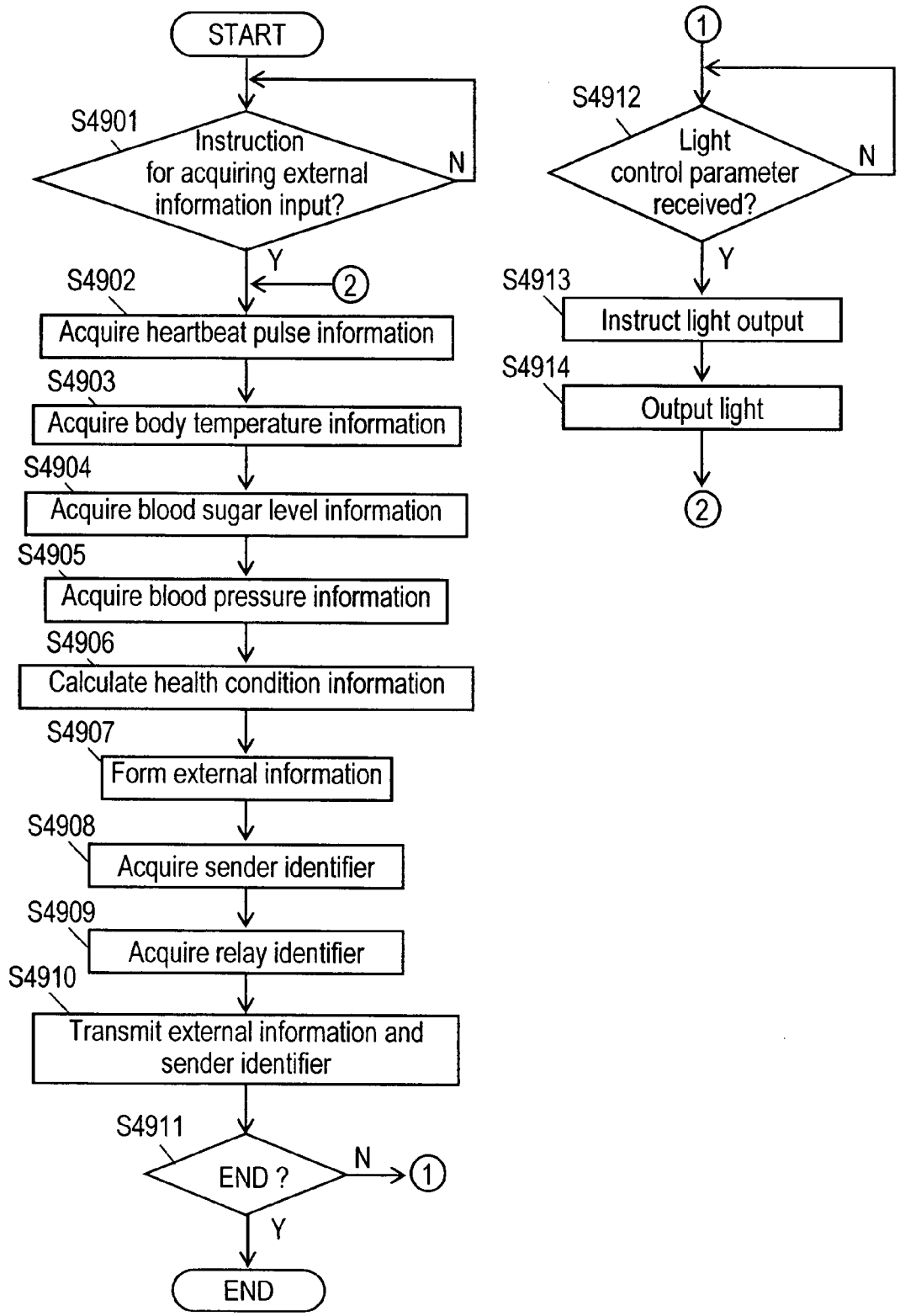
FIG. 49 is a flow chart used to describe the operation of a light output device in the eighth embodiment.

In the flow chart, FIG. 49, the external information is acquired based upon inputting by a user of an instruction for acquiring the external information. However, it may be acquired without having any triggering; or, it may be performed when triggered by an order delivered from an external apparatus (relay 1102 or other apparatus).

Although in the flowchart, FIG. 49, all the heartbeat pulse information, body temperature information, blood sugar level information, blood pressure information and health condition information were transmitted, these may be transmitted only in part, as the external information.

Since relay 1102 has the same structure as that in embodiment 4, and operates in the same manner as in embodiment 4, the description on which is eliminated here. Relay 1102 determines a light control parameter based on the external information sent from first light output device 4801 and that from second light output device 4803. The external information here indicates one or more pieces of information among the heartbeat pulse information, body temperature information, blood sugar level information, blood pressure information and health condition information.

Second light output device 4803 has the same structure and performs the same function as that of first light output device 4801. That is, constituent elements designated as Third--unit perform the same functions as those of First--unit. This statement likewise applies also in other embodiments. Therefore, description on which part is eliminated here.

Now, the operation of present information processing system is described practically in the following.

Figures 50, 51:
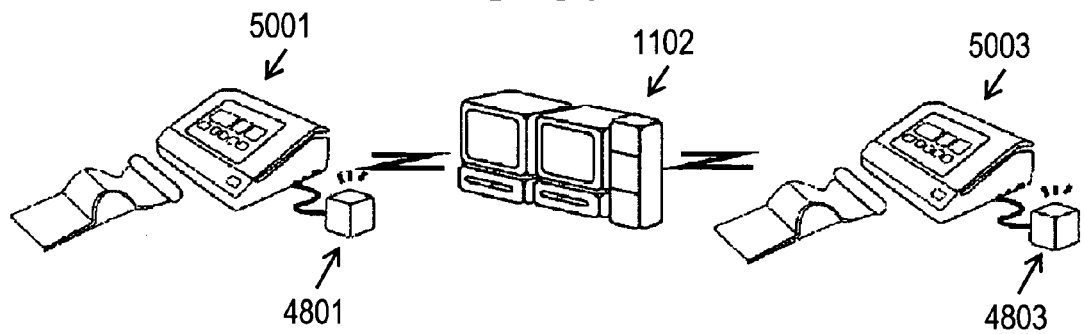
FIG. 50 illustrates the concept of an information processing system in the eighth embodiment.
FIG. 51 shows a table stored in a health condition information acquisition unit in the eighth embodiment.

As shown in FIG. 50, the present information processing system includes electronic health checker 5001 and first light output device 4801 connected with the health checker, relay 1102, and electronic health checker 5003 and second light output device 4803 connected with the health checker. These can transmit/receive information among each other through a communication apparatus, or a broadcasting apparatus. Each of the first and second light output devices can acquire blood pressure information, etc. from the electronic health checker connected therewith.

As described in the above, the electronic health checker can acquire heartbeat pulse information, body temperature information, blood sugar level information and blood pressure information. Suppose, health condition information acquisition unit keeps heartbeat pulse information and other information items having such merit point ranges as shown in FIG. 51. The health condition information acquisition unit treats a sum total of the merit points, which merit points corresponding to respective values of the heartbeat pulse information, body temperature information, blood sugar level information and blood pressure information acquired at the previous step, as the health condition information.

In an exemplary case where the heartbeat pulse information indicates "78", the body temperature information "36.5", the blood sugar level information "80" and the blood pressure information "high: 133, low: 70"; then the merit point for heartbeat pulse information is "10", for the body temperature information is "25", for the blood sugar level information is "25" and for the blood pressure information is "25", making a sum total "85", or the health condition information is "85". This value represents the general health condition level of an entire human body, to a full mark of 100.

Suppose, for example, first external information 5201 as shown in FIG. 52 is transmitted from first light output device 4801 to the relay, while second external information 5202 is transmitted from second light output device 4803 to relay 1102.

Then, the relay determines a light control parameter in the following manner:

In the first place, the relay is supposed to respond only to the heartbeat pulse information, among other external information received. When the values of the heartbeat pulse information contained in the first external information and the second external information are closer to each other, then a greater value is assigned to the light control parameter. That is, if the heartbeat pulse information transmitted from respective light output devices bear similar values, then it can be generally interpreted that the two users of the devices are in almost the same excitement level. When, respective light output devices emit a great and bright light. A practical example; if both of a couple of lovers bearing the light output devices have the heart-throbs of similar excitement level, then the light output devices exhibit a bright light.

In the second place, suppose the relay reacts to the blood sugar level information and blood pressure information, among other external information. The relay's light control parameter determination unit stores the table shown in FIG. 51, and refers the two pieces of received information, blood sugar level information and blood pressure information, to the table. The lower of the merit points representing two pieces of blood sugar level information is adopted as the control parameter. And, the lower of the merit points representing two pieces of blood pressure information is adopted as the control parameter. The two parameters are transmitted to respective light output devices, as the light control parameter. Each of the light output devices is provided with two light output units (which represents the other example of the earlier described embodiment), and the light output units respond to the blood sugar level parameter and the blood pressure parameter, respectively, and emits the light accordingly.

The above-described example can be used in the following practical application:

Suppose both of two persons are suffering from geriatric diseases, and they are friends who are trying to overcome the diseases. The light output devices provide a brilliant light only when both of the friends are in the course towards improvement.

A third example; suppose the relay responds only to the health condition information, among the received external information. And, the lower of the health condition information's values contained in the first external information and the second external information makes the light control parameter. That is, a high-value light control parameter is provided only when both of the two persons using the light output devices are in good health; or, the light control parameter is provided with a high value only when both of the two pieces of health condition information exhibit high values. The light output devices are lit brilliantly when a high-value light control parameter is used, with the proviso that a voltage to be applied on a light output device is proportional to the light control parameter. Hence, suppose a relay determines a light control parameter collecting health condition information of the two or more people forming a group. Then, the worst of the health condition information is adopted as the light control parameter. Respective light output devices emit the light in accordance with the light control parameter. In a case where an assignment is performed by a group, a good result can be attained only when the entire group member is in good health. The above-described configuration offers a system, with which the condition of an entire group people is exhibited in an indirect manner by means of a light output.

In FIG. 52, the external information is shown in the form of information with tag. However, there is no limitation in the data form and data structure.

The mode of light output has been described with focus on a light intensity variation mode. However, it is not the intention to limit the light output to the intensity variation mode; the earlier-described 5 kinds of light output modes may be considered to be practical modes. Still other light output modes may of course be introduced, in so far as it can represent a state of certain things in a soft manner.

In the present embodiment, as described in the above, the information on health condition from two or more light output devices are communicated to a relay, and respective light output devices output the light based on a light control parameter determined at the relay.

An exemplary application of the present embodiment is described below. Respective light output devices are held by each of a couple of lovers. One person grasps first light output device, and the body temperature is conveyed to the relay. The other person grasps the second light output device, and the body temperature is conveyed to the relay. When both of them grasp respective devices firmly and passionately, it is reflected to the light control parameter as a high value, by a calculation conducted at the relay. The light is outputted in accordance with the parameter, and each of the lovers can feel heated passions for each other.

Although the information processing terminal in the present embodiment is shown in FIG. 50 in the shape of a readily available electronic health checker, the information processing terminal can take a cubic form, or whatever. If the terminal is cubic-shaped, it can be grasped by hand. Further, if it can detect the "heartbeat pulse", "body temperature", etc. through the grasping hand, it will provide an additional advantage in the usage. That is, when the cubic-shaped light output device is grasped firmly, a highly motivated sentiment of the holding person (heartbeat pulse information) and warmth of the holding person (body temperature information) are conveyed to the relay. And, respective light output devices generates the light in accordance with a light control parameter determined by the relay.

Although all of the heartbeat pulse information, body temperature information, blood sugar level information, blood pressure information and health condition information have been transmitted/received in the present embodiment, it is not essential to exchange the whole items of the information always. Exchange of one or more items of such information would serve the purpose. Other information items physically measurable with the human body or animal body, such as adiposity rate, may of course be the subject of transmission/reception.

Embodiment 9

Figure 53:
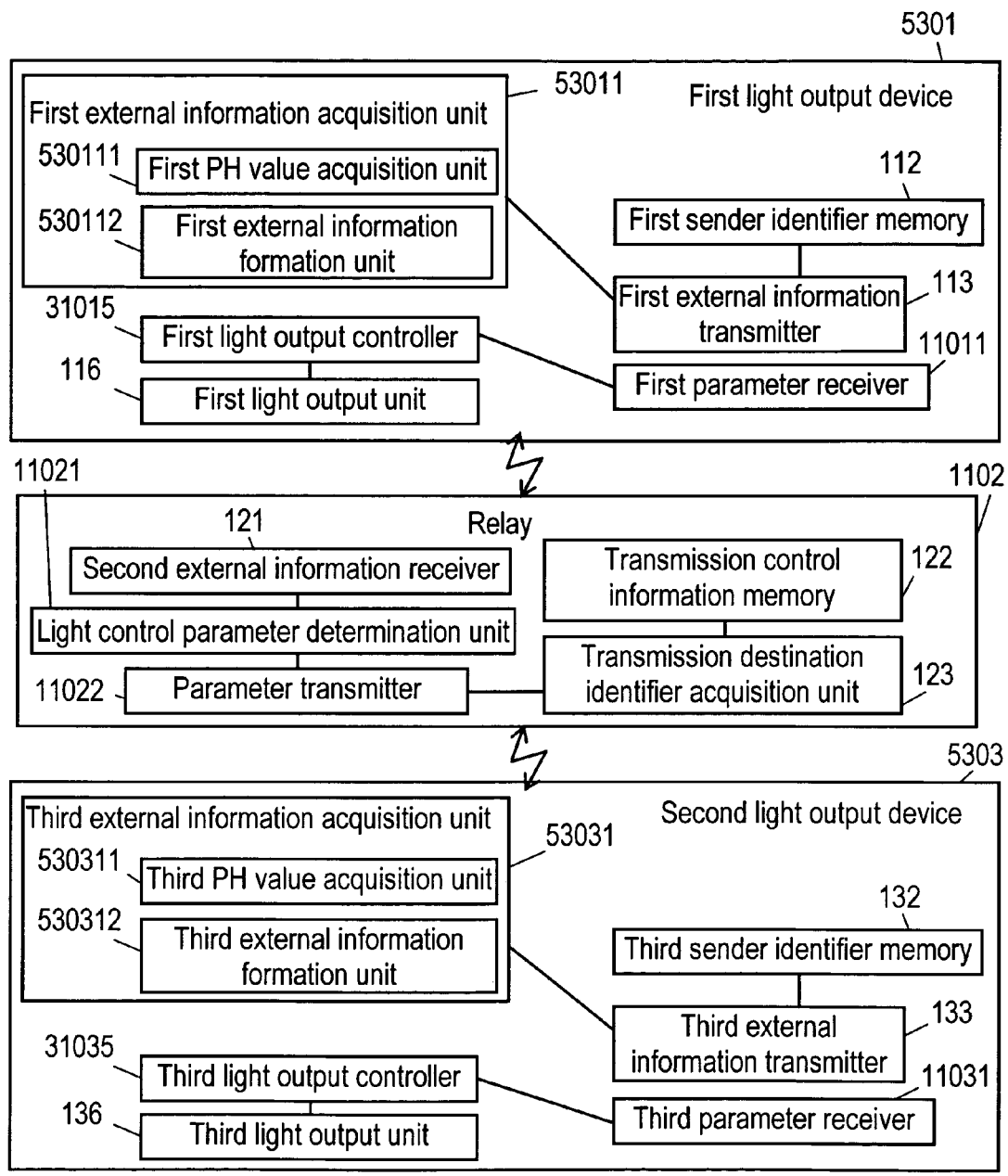
FIG. 53 is a block diagram of an information processing system in a ninth exemplary embodiment.

FIG. 53 is a block diagram showing an information processing system in accordance with the present exemplary embodiment.

The present information processing system is formed of first light output device 5301, relay 1102 and second light output device 5303.

First light output device 5301 includes first external information acquisition unit 53011, first sender identifier memory 112, first external information transmitter 113, first parameter receiver 11011, first light output controller 31015 and first light output unit 116.

First external information acquisition unit 53011 includes first PH value acquisition unit 530111 and first external information formation unit 530112.

First PH value acquisition unit 530111 measures PH value of first light output device 5301. Since first PH value acquisition unit 530111 can be implemented with a known technology, no detailed description on which is made here.

External information formation unit 530112 forms the external information based on a PH value measured at PH value acquisition unit 530111.

Now, the operation of first light output device 5301 is described with reference to FIG. 54, a flow chart.

(Step S5401) First PH value acquisition unit 530111 acquires PH value of the first light output device.

(Step S5402) First PH value acquisition unit 530111 reads out a PH value which was stored in advance in first external information formation unit 530112 (for a convenience, the value is sometimes referred to as "normal PH value").

(Step S5403) First PH value acquisition unit 530111 judges whether there is a difference not less than a predetermined value between the PH value acquired at S5401 and the PH value read at S5402, or not. If there is such a difference, it proceeds to S5404; if not, it returns to S5401.

(Step S5404) First external information formation unit 530112 forms external information based on the PH value acquired at S5401.

(Step S5405) First external information transmitter 113 acquires a sender identifier from first sender identifier memory 112.

(Step S5406) First external information transmitter 113 acquires relay identifier which is an information for identifying a relay. The relay identifier is stored in a memory not shown in the drawing.

(Step S5407) First external information transmitter 113 transmits external information and a sender identifier to a relay identified by the relay identifier.

(Step S5408) First light output device 5301 judges whether a finish signal is received, or not. If yes, it is finished; if not received, it proceeds to S5409.

(Step S5409) First light output device 5301 waits for a certain specific time. Then it proceeds to S5410.

(Step S5410) First parameter receiver 11011 judges whether a light control parameter is received, or not. If it is received, it proceeds to S5411; if not received, it repeats S5410.

(Step S5411) First light output controller 31015 instructs first light output unit 116 to output the light in accordance with a control parameter received at S5410.

(Step S5412) First light output unit 116 outputs the light in accordance with instruction of first light output controller 31015.

Figure 54:
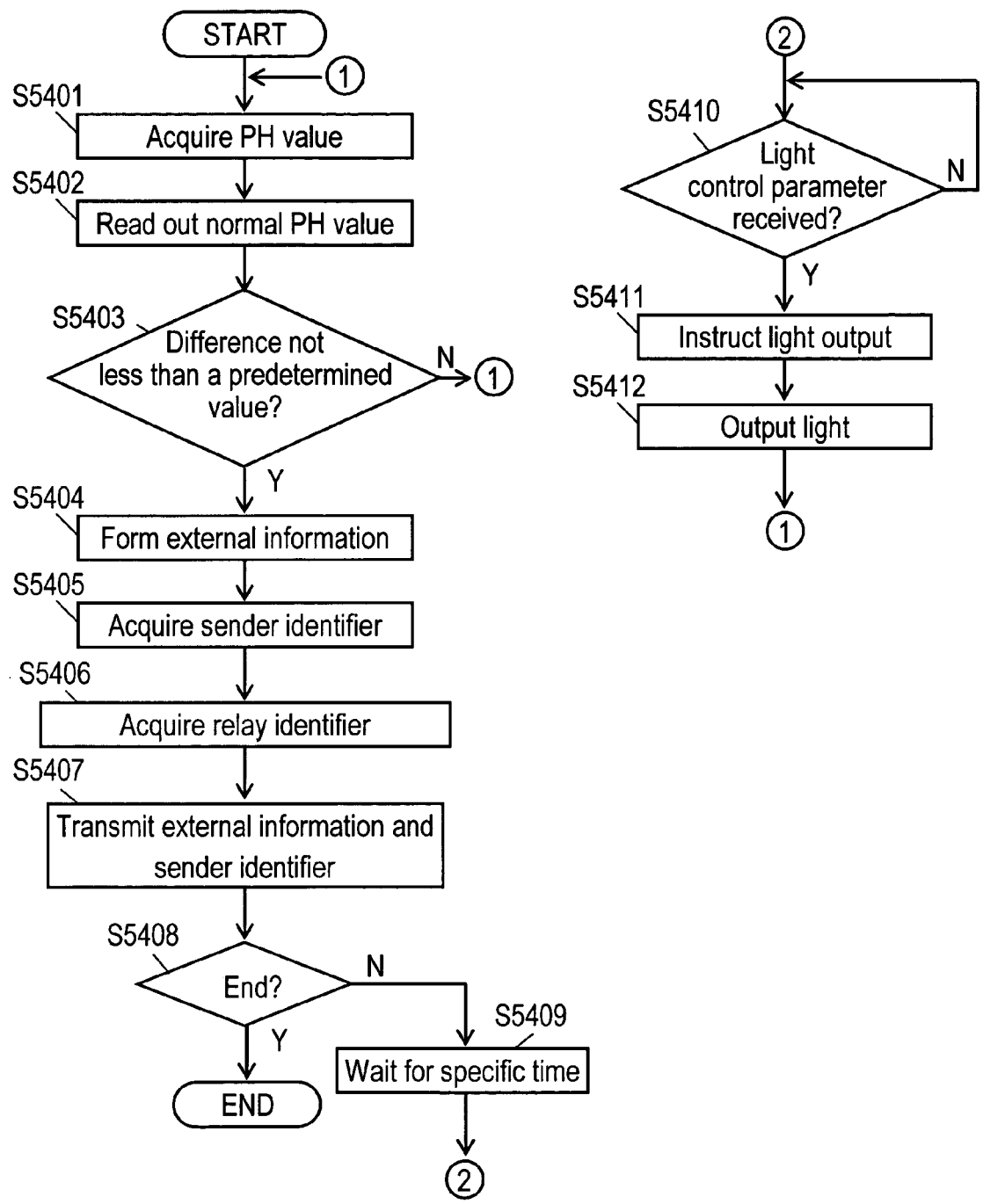
FIG. 54 is a flow chart used to describe the operation of a light output device in the ninth embodiment.

In the flow chart, FIG. 54, the PH value was acquired without having any triggering. However, the acquiring operation may be started upon triggering by first light output device 5301's user pressing a start button. Or, the PH value acquisition at S5401 may be started upon receipt of a triggering signal from second light output device 5303, relay 1102 or other devices.

An exemplary case in which second light output device 5303 triggers first light output device 5301 is as the following case.

When second light output device 5303's PH value changed, first light output device 5301 is advised to acquire PH value.

In the flow chart, FIG. 54, when an acquired PH value differs from the normal PH value for more than a certain predetermined value, the PH value is transmitted to relay. However, an acquired PH value may unconditionally transmitted to a relay.

Since relay 1102 has the same structure as that in embodiment 4 and operates in the same manner as in embodiment 4, the description of which is eliminated here.

Since the operation of second light output device 5303 remains the same as that of first light output device 5301, the description of which is eliminated here.

Now, the operation of an information processing system in the present invention is described practically.

Each of the respective light output devices of the present information processing system is capable of measuring PH value, as described in the above. When an information processing terminal is licked by a person, it is considered that the terminal normally exhibits a substantial shift in the PH value. Thus the licking action can be communicated from the light output device to a relay. If an information indicating that at least one of the two light output devices is licked (such information can be provided in terms of the PH value) is transmitted to a relay, the relay generates a light control parameter and respective light output devices output the light.

Describing specifically, the relay determines a light control parameter in accordance with the table shown in FIG. 55. If an information indicating that both of the first light output device and the second light output device are licked (a certain specific PH value may represent such a situation) is transmitted to relay (row "YES" "YES", in FIG. 55), the light control parameter is determined to be "5". This corresponds to a record in the bottom line of FIG. 55. If the information indicating that either one of the first light output device and the second light output device is licked (other certain specific PH value may represent such a situation) is transmitted to relay (rows "YES" "NO", "NO" "YES", in FIG. 55), the light control parameter is determined to be "1". This corresponds to records in the second and third lines from the bottom in FIG. 55. In the latter situation, where the licking is made to only one of the devices, the light is outputted in accordance with the light control parameter "1". If the light control parameter is a light intensity index, a dim and obscure light is outputted. When the licking is made to both of the light output devices, respective light output devices generate the light in accordance with the light control parameter "5". That is, both of the light output devices emit a considerably brilliant light.

In the present embodiment, when respective light output devices transmit an external information containing a certain PH value (an information indicating that it is licked) to a relay, a light control parameter is determined based on the situation that respective light output devices' users licked respective light output devices and two or more number of PH values representing the situation. Respective light output devices emit the light in accordance with the light control parameter. When the devices are used as such among certain specific partners, the licking action or an expression of love affection can be communicated in a soft mood in the form of a light output.

Embodiment 10

Figure 56:
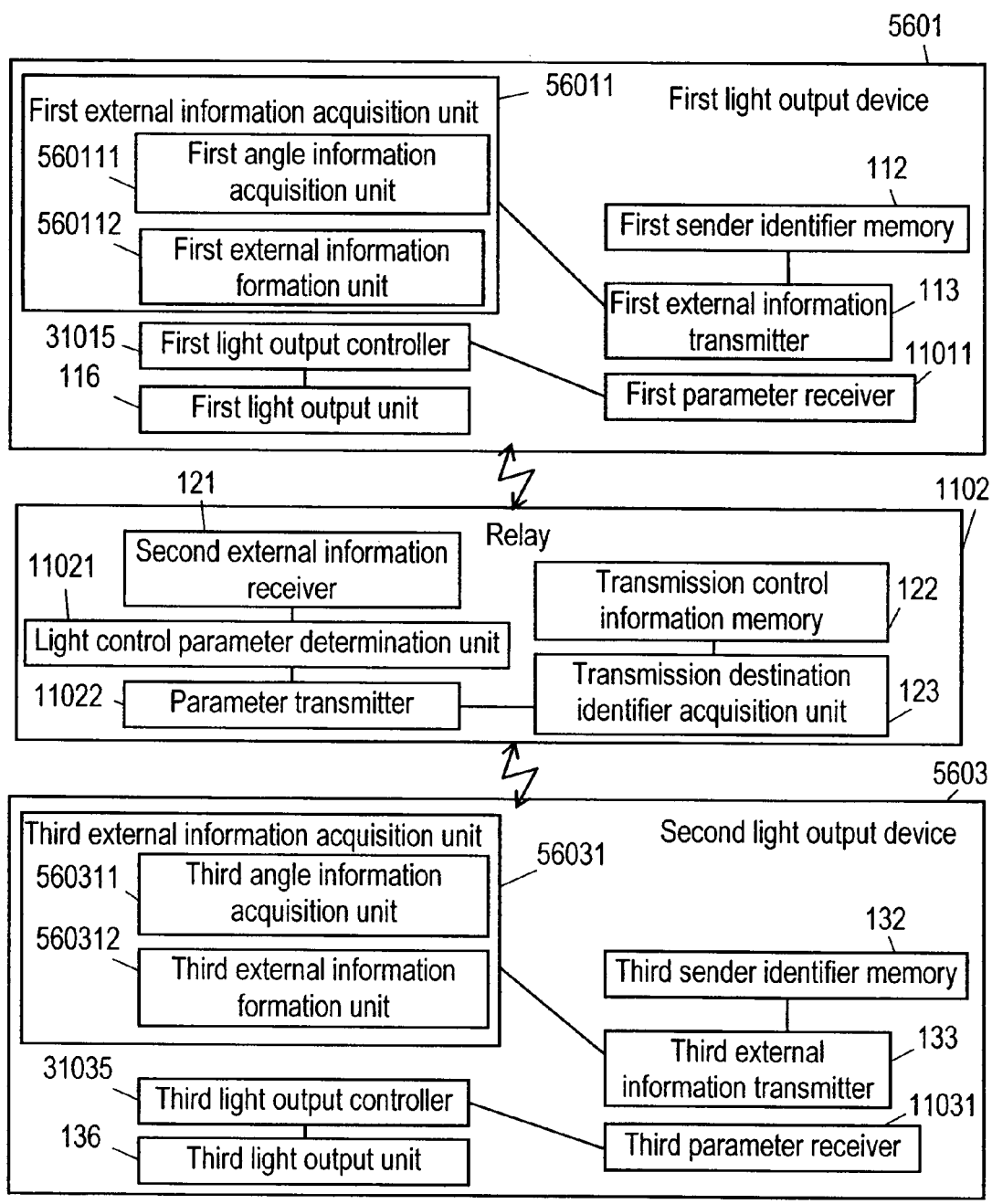
FIG. 56 is a block diagram of an information processing system in a tenth exemplary embodiment.

FIG. 56 is a block diagram showing an information processing system in the present embodiment. The present information processing system is formed of first light output device 5601, relay 1102 and second light output device 5603.

First light output device 5601 includes first external information acquisition unit 56011, first sender identifier memory 112, first external information transmitter 113, first parameter receiver 11011, first light output controller 31015 and first light output unit 116.

First external information acquisition unit 56011 includes first angle information acquisition unit 560111 and first external information formation unit 560112.

First angle information acquisition unit 560111 acquires angle information which is the information on the angle (tilt) of first light output device 5601. The angle information may mean, for example, an angle, an amount of change in the angle, or an angular velocity, etc. First angle information acquisition unit 560111 can be implemented with, for example, a gyro, a clinometer, etc. Since the gyros, clinometers, etc. belong to a known technology, description on which is eliminated here. Either a mechanical gyro or an optical fiber gyro may be used for first angle information acquisition unit 560111.

First external information formation unit 560112 forms external information based on angle information acquired at first angle information acquisition unit 560111.

Now, the operation of first light output device 5601 is described with reference to FIG. 57, a flow chart.

(Step S5701) First angle information acquisition unit 560111 judges whether an angle change is detected, or not. If there is a change in the angle, it proceeds to S5702; if not detected, it repeats S5701.

(Step S5702) First angle information acquisition unit 560111 acquires angle information.

(Step S5703) First external information formation unit 560112 forms external information based on the angle information acquired at S5702.

(Step S5704) First external information transmitter 113 acquires a sender identifier from first sender identifier memory 112.

(Step S5705) First external information transmitter 113 acquires a relay identifier which is an information for identifying a relay. The relay identifier is stored in advance in a memory not shown in the drawing.

(Step S5706) First external information transmitter 113 transmits external information and sender identifier to a relay identified by the relay identifier.

(Step S5707) First light output device 5601 judges whether a finish signal is received, or not. If yes, it is finished; if not received, it proceeds to S5708.

(Step S5708) First light output device judges whether first parameter receiver 11011 received a light control parameter, or not. If a light control parameter is received, it proceeds to S5709; if not received, it repeats S5708.

(Step S5709) First light output controller 11015 instructs first light output unit 116 to output the light based on the control parameter received at S5708.

(Step S5710) First light output unit 116 outputs the light in accordance with instruction of first light output controller 11015. It returns to S5701.

Figure 57:
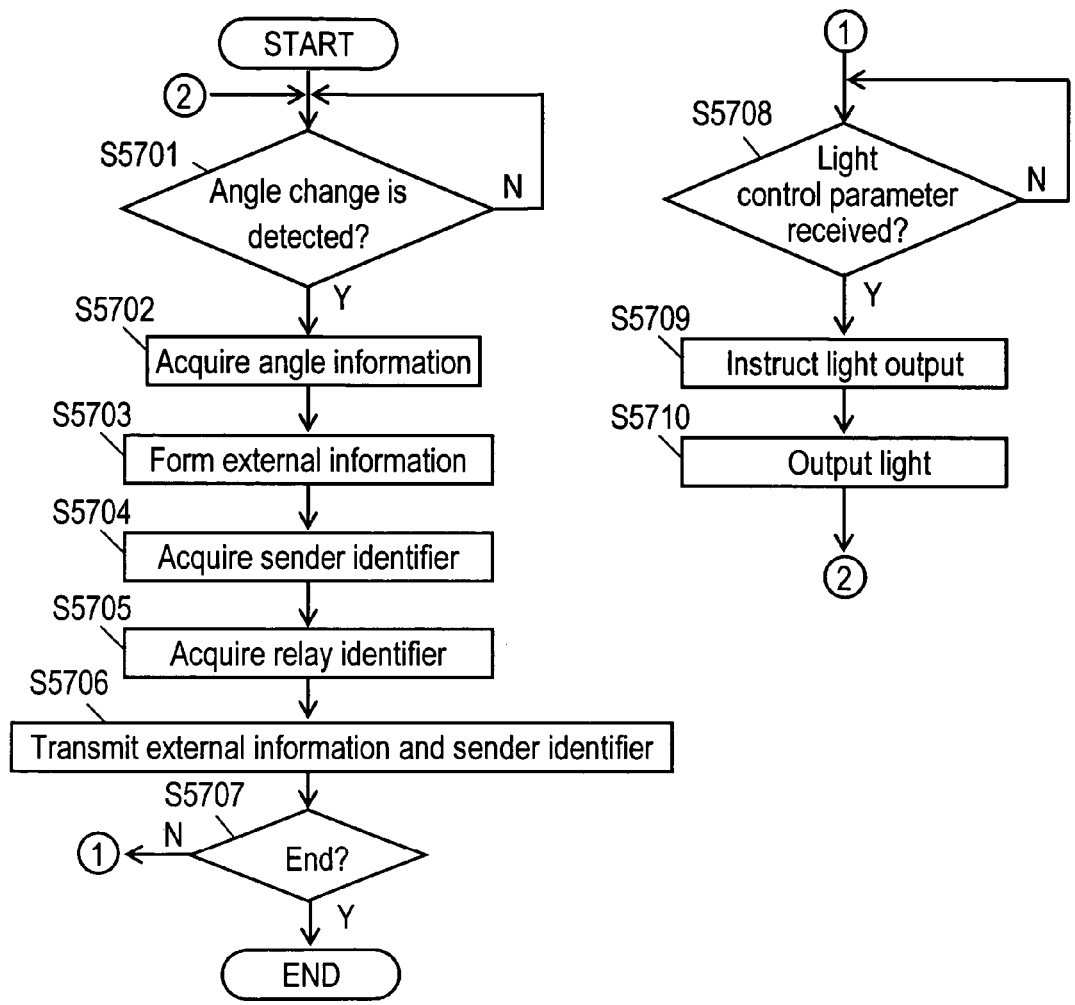
FIG. 57 is a flow chart used to describe the operation of a light output device in the tenth embodiment.

In the flow chart, FIG. 57, the angle information is acquired triggered by detection of an angle change. However, the angle information may be acquired without having any triggering, and the acquired information may be sent to the light output device. Or, the acquisition of angle information may be conducted upon receiving a triggering signal from second light output device 5603, relay 1102 or other apparatus; and the acquired angle information may be transmitted to light output device.

Since relay 1102 has the same structure as that in embodiment 4 and operates in the same manner as in embodiment 4, description on these are eliminated here.

Since second light output device 5603 operates in the same manner as first light output device 5601, the description on which is eliminated here.

Now, the operation of an information processing system in the present embodiment is described practically.

Figure 58:
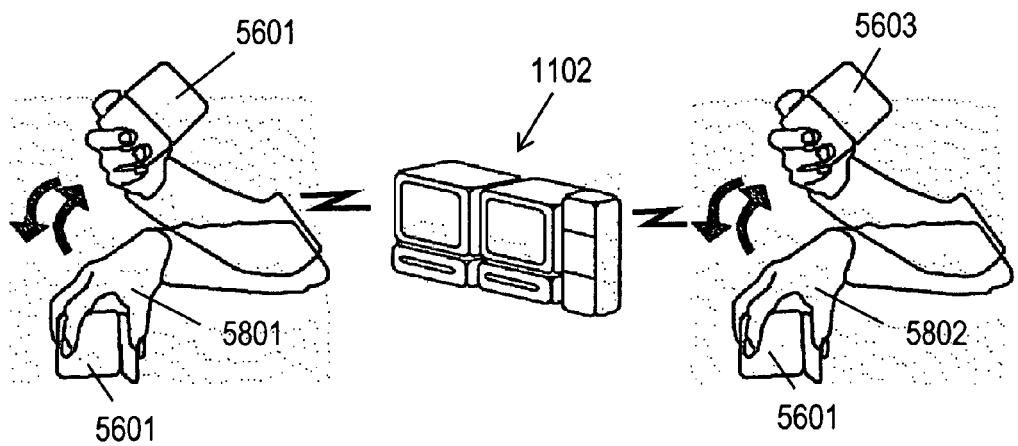
FIG. 58 illustrates the concept of an information processing system in the tenth embodiment.

The first light output device and the second light output device of the present information processing system are shaped cubic. As shown in FIG. 58, user(s) of first light output device or/and second light output device holds and shakes device 5601 or/and 5603 with hand(s) 5801 or/and 5802. Then, an amount of angle change is detected with the shaken first light output device or/and second light output device, and the amount of angle change forms external information. The external information is communicated to the relay. The relay sums the amounts of angle change at the first light output device and the second light output device, and determines the sum as the light control parameter, and transmits the parameter to the first light output device and the second light output device. First light output device and second light output device output the light in accordance with the light control parameter. Specifically, the light control parameter represents the intensity of the light; the greater the parameter value, the brighter are the light output devices. That is, when the first light output device's user and the second light output device's user shake respective devices vigorously, these light output devices are lit brilliantly in proportion to vigorousness level of the shaking.

In the present embodiment, when two or more number of light output devices are shaken, degree of the shaking action is transmitted to the relay, and the vigorousness level of the action shaking the two or more number of light output devices is exhibited in terms of light with a soft mood.

Suppose, for example, one party of a couple in love holds first light output device while the other holds second light output device, both of them can communicate an aroused love sentiment to the other by shaking respective light output devices violently. When both of the light output devices are shaken violently, the light outputs become more brilliant. Thus, the partners can softly learn each other that the other party is earnestly wishing to meet personally.

Embodiment 11

Figure 59:
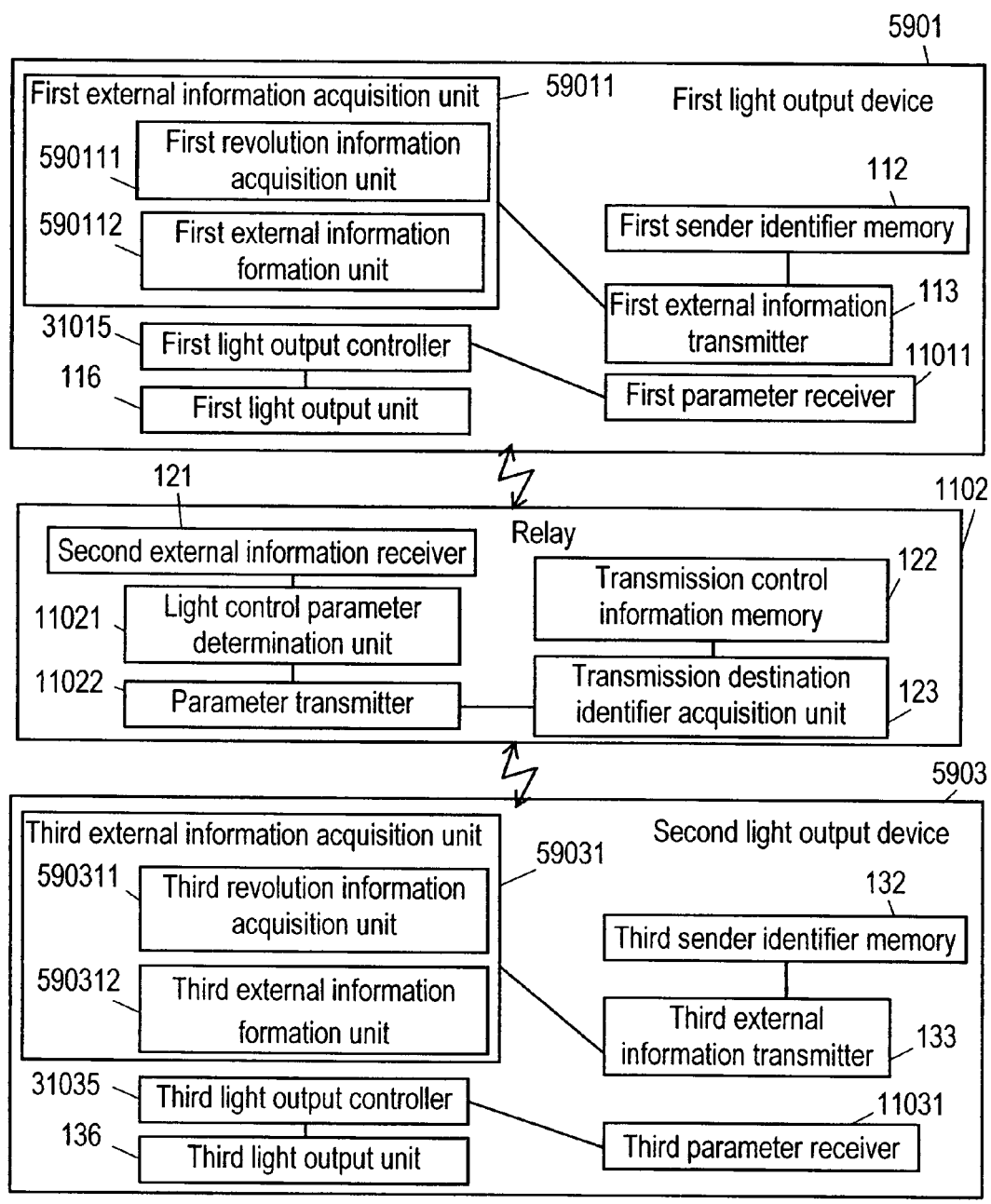
FIG. 59 is a block diagram of an information processing system in an eleventh exemplary embodiment.

FIG. 59 is a block diagram showing an information processing system in the present embodiment.

The present information processing system is formed of first light output device 5901, relay 1102 and second light output device 5903.

First light output device 5901 includes first external information acquisition unit 59011, first sender identifier memory 112, first external information transmitter 113, first parameter receiver 11011, first light output controller 31015 and first light output unit 116.

First external information acquisition unit 59011 includes first revolution information acquisition unit 590111 and first external information formation unit 590112.

First revolution information acquisition unit 590111 acquires revolution information which is information about, for example, revolution of a windmill, etc. installed on first light output device 5901. The revolution information indicates a revolution speed, a number of revolutions, etc. Since the technology for detecting the revolution speed and number of revolutions is a known technology, detailed description on which is eliminated here.

External information formation unit 530112 forms external information based on revolution information acquired at first revolution information acquisition unit 590111. External information formation unit 530112 can be implemented normally with software, but a dedicated circuit (hardware) may be used instead.

Figure 60:
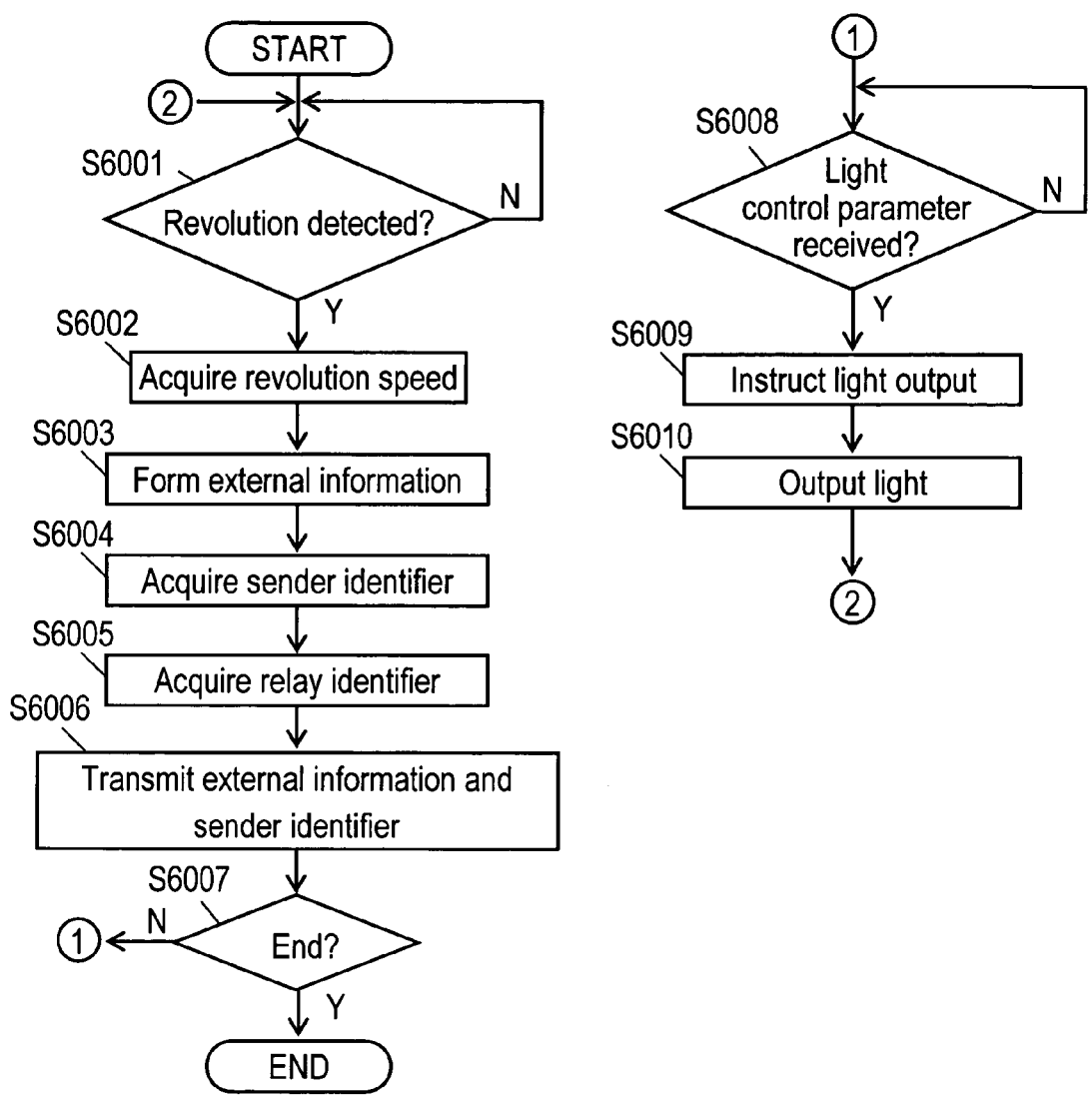
FIG. 60 is a flow chart used to describe the operation of a light output device in the eleventh embodiment.

Now, the operation of first light output device 5901 is described with reference to FIG. 60, a flow chart.

(Step S6001) First revolution information acquisition unit 590111 judges whether a revolution is detected, or not. If yes, it proceeds to S6002; if no revolution is detected, it repeats S6001.

(Step S6002) First revolution information acquisition unit 590111 acquires revolution information.

(Step S6003) First external information formation unit 590112 forms external information based on revolution information acquired at S6002.

(Step S6004) First external information transmitter 113 acquires a sender identifier from first sender identifier memory 112.

(Step S6005) First external information transmitter 113 acquires a relay identifier which is the information for identifying a relay. The relay identifier is supposed to have been stored in a memory not shown in the drawing.

(Step S6006) First external information transmitter 113 transmits external information and a sender identifier to a relay identified by the relay identifier.

(Step S6007) First light output device 5901 judges whether a finish signal is received, or not. If yes, it is finished; if not received, it returns to S6008.

(Step S6008) First light output device 5901 judges whether first parameter receiver 11011 received a light control parameter, or not. If a light control parameter is received, it proceeds to S6009; if not received, it repeats S6008.

(Step S6009) First light output controller 11015 instructs first light output unit 116 to output the light based on a control parameter received at S6008.

(Step S6010) First light output unit 116 outputs the light in accordance with instruction of first light output controller 11015.

In the flow chart, FIG. 57, the acquisition of revolution information is conducted triggered by detection of a revolution. However, the revolution information may be acquired without having any triggering (including a situation where value is 0), and the acquired information may be transmitted to the light output device. Or, the revolution information may be acquired upon receiving a triggering signal from second light output device 5903, relay 1102 or other apparatus, and the acquired revolution information may be transmitted to the light output device.

Now, the operation of an information processing system in the present embodiment is practically described.

Figure 61:
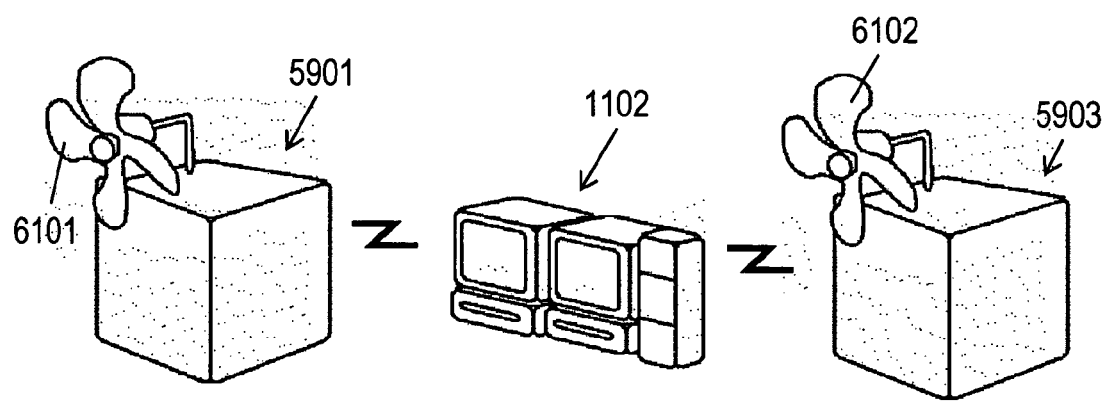
FIG. 61 illustrates the concept of an information processing system in the eleventh embodiment.

First light output device 5901 and second light output device 5903 of the present information processing system are shaped cubic, as shown in FIG. 61, and each is electrically connected, respectively, with windmill 6101 and windmill 6102. Respective light output devices are provided with revolution speed detection means, which detects the revolution speed of the blown windmill. The revolution information representing the revolution speed is transmitted from the respective light output devices to the relay. Then, the relay determines a light control parameter based on the revolution information transmitted from respective light output devices, and transmits the light control parameter to respective light output devices. Respective light output devices softly generate the light.

In the present embodiment, a windmill starts revolving when light output device is blown by wind. The revolving speed and a number of revolutions (revolution information) are communicated softly to a relay, and the relay transmits a light control parameter to the light output devices. And, the light output devices output the light. Suppose, for example, two specific persons bear, respectively, the light output device, and both of them blow the windmill of own side. That is, their strong desires for meeting together are replaced with the action of blowing windmills. The stronger the respective breaths are blown towards the windmills, the brighter the light output devices shine. Thus, by blowing the windmill at their own side strongly, their strong desires for meeting can be exchanged among each other in the form of a soft implication.

Embodiment 12

Figure 62:
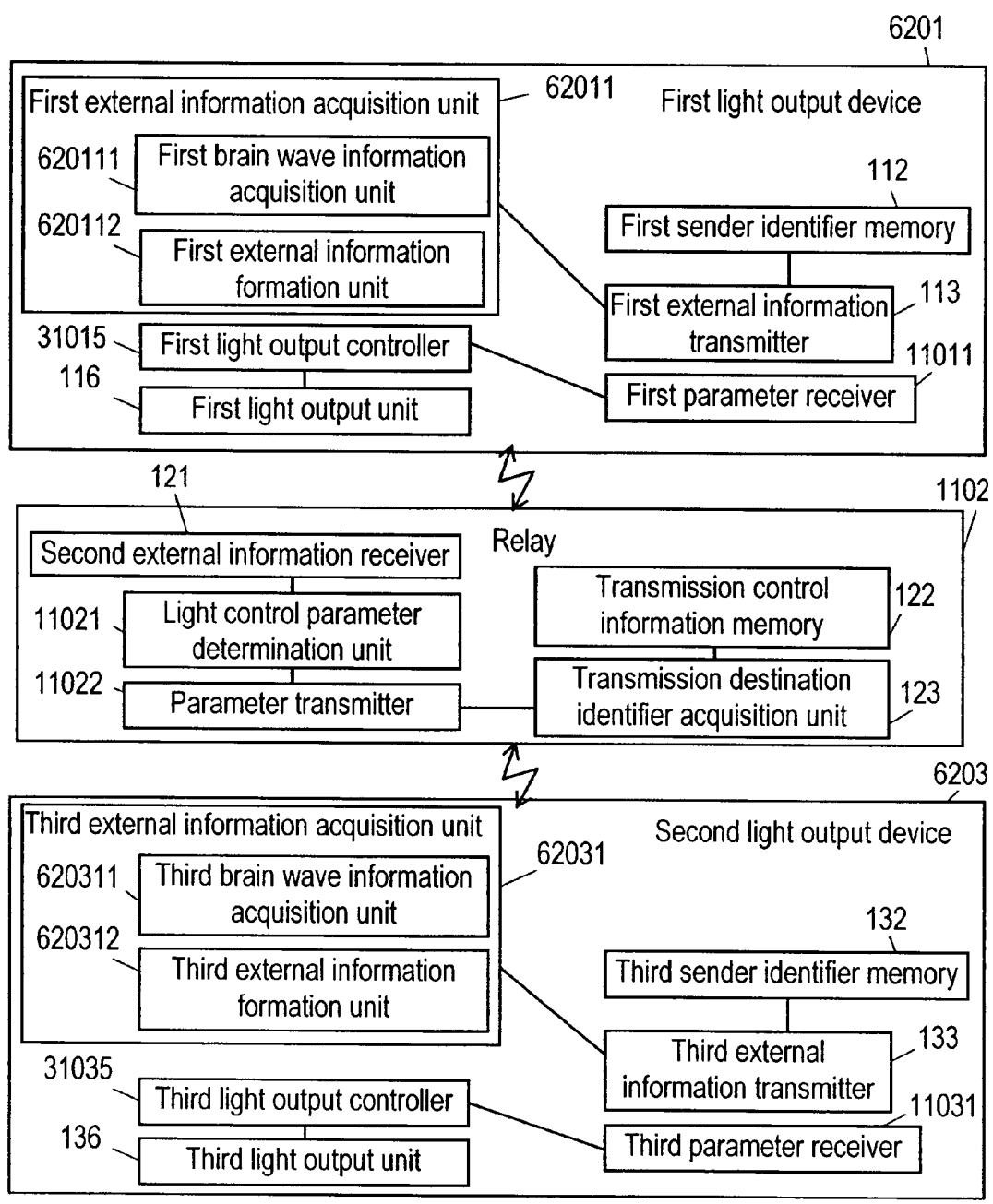
FIG. 62 is a block diagram of an information processing system in a twelfth exemplary embodiment.

FIG. 62 is a block diagram showing an information processing system in the present embodiment. The present information processing system is formed of first light output device 6201, relay 1102 and second light output device 6203.

First light output device 6201 includes first external information acquisition unit 62011, first sender identifier memory 112, first external information transmitter 113, first parameter receiver 11011, first light output controller 31015 and first light output unit 116.

First external information acquisition unit 62011 includes first brain wave information acquisition unit 620111 and first external information formation unit 620112.

First brain wave information acquisition unit 620111 measures brain wave to acquire the brain wave information. Since the technology for measuring a brain wave is a known technology, detailed description on which is eliminated here.

First external information formation unit 620112 forms external information based on the brain wave information acquired at first brain wave information acquisition unit 620111. First external information formation unit 620112 can be implemented normally with software, but a dedicated circuit (hardware) may be used instead.

Now, the operation of first light output device 6201 is described with reference to FIG. 63, a flow chart.

(Step S6301) First brain wave information acquisition unit 620111 judges whether an instruction to start measuring brain wave is received, or not. If yes, it proceeds to S6302; if no such instruction is detected, it returns to S6301.

(Step S6302) First external information formation unit 620112 acquires brain wave information.

(Step S6303) First external information formation unit 620112 forms external information based on the brain wave information acquired at S6302.

(Step S6304) First external information transmitter 113 acquires a sender identifier from first sender identifier memory 112.

(Step S6305) First external information transmitter 113 acquires a relay identifier which is the information for identifying a relay. The relay identifier is supposed to have been stored in a memory not shown in the drawing.

(Step S6306) First external information transmitter 113 transmits external information and a sender identifier to a relay identified by the relay identifier.

(Step S6307) Whether a finish signal is received, or not, is judged. If such a signal is received, it is finished; if not received, it proceeds to S6308.

(Step S6308) First light output device 6201 judges whether first parameter receiver 11011 received a light control parameter, or not. If a light control parameter is received, it proceeds to S6309; if not received, it repeats S6308.

(Step S6309) First light output controller 11015 instructs first light output unit 116 to output the light based on the control parameter received at S6308.

(Step S6310) First light output unit 116 outputs the light in accordance with instruction of first light output controller 11015. It returns to S6302.

Figure 63:
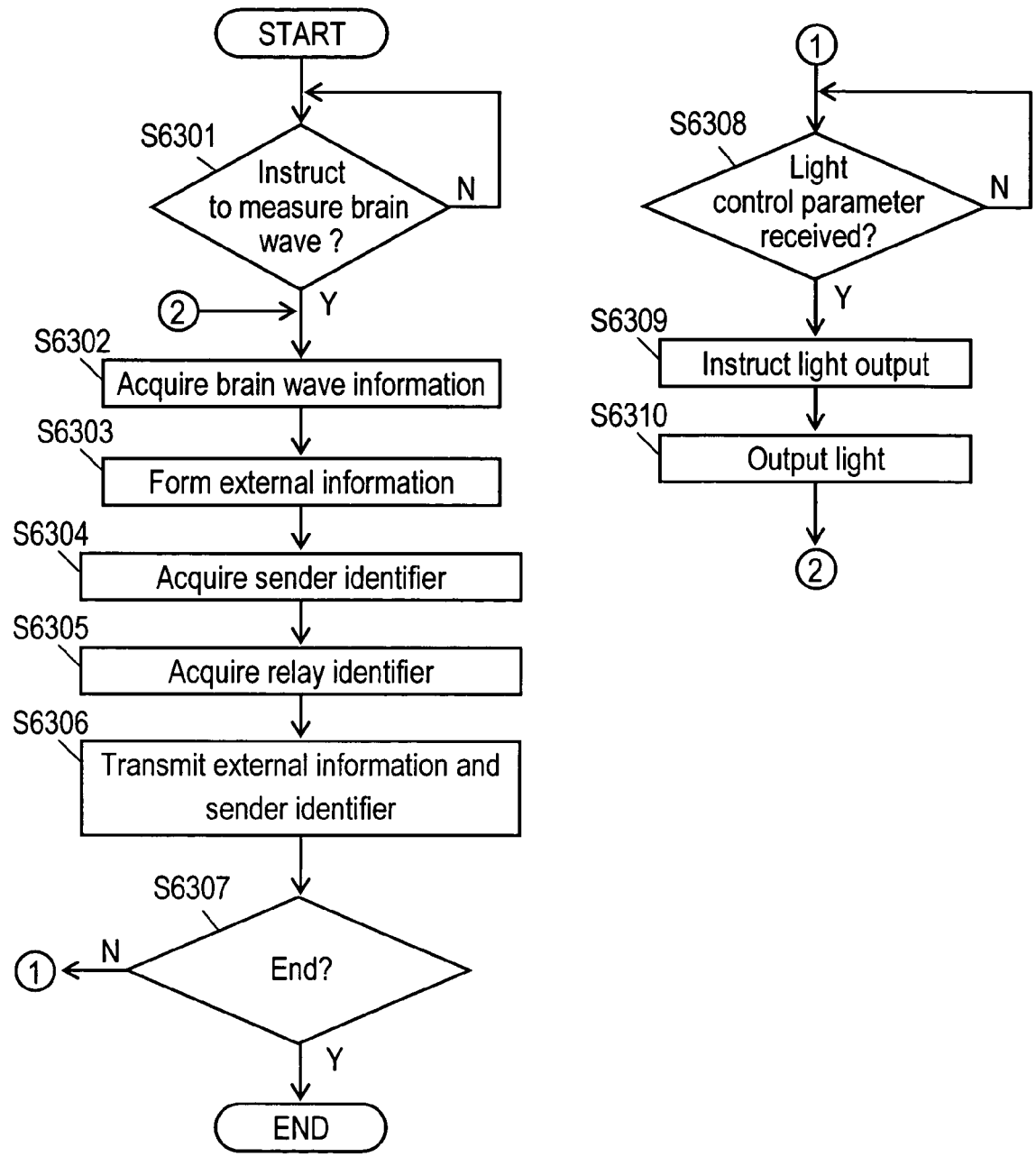
FIG. 63 is a flow chart used to describe the operation of a light output device in the twelfth embodiment.

In the flow chart, FIG. 63, the brain wave measurement is started upon receipt of an instruction to start measurement. However, the acquisition of brain wave information may be conducted without having any triggering, and the acquired information may be transmitted to the light output device. Furthermore, the brain wave information may be acquired upon receipt of a triggering signal from second light output device 6203, relay 1102 or other apparatus, and the acquired information may be transmitted to light output device.

Since relay 1102 has the same structure as that of embodiment 4, and operates in the same manner as in embodiment 4, the description on which is eliminated here.

Since second light output device 6203 operates in the same manner as first light output device 6201, the description on which is eliminated here.

In the present embodiment, brain wave values measured of a plurality of persons are communicated to a relay, and the relay determines a light control parameter based on the brain wave information of the plurality of persons. Respective light output devices emit the light based on the light control parameter.

Suppose, for example, a plurality of people's brain wave information is communicated to a relay. From each brain wave information, it can observe whether the individuals are generating the α wave more, or the β wave more. The relay calculates a light control parameter; the higher is the number of people feeling stress, the higher is the parameter value. Given the above-described suppositions and everybody in a certain workshop are bearing the present light output device, if the workshop is stressful the light output devices generate light output powerfully. Thus the present system offers a useful tool for improving the job environment. The above descriptions are intended to show just an exemplary possibility of application. The field of application for the present system is not limited to the above, but it can be used in many more ways.

INDUSTRIAL APPLICABILITY

As described in the above, the light output devices in the present invention generate the light outputs based on a plurality of pieces of external information representing the status of things at the light output devices' users. This helps facilitating a natural and appropriate communication among a plurality of forming a group.

The invention claimed is:

1. A light output device for communicating with another light output device, the light output device comprising:
    an external information receiver for receiving first external information, wherein the first external information is a first portion of external information transmitted from a source outside of the light output device;
    an external information acquisition unit for acquiring second external information, wherein the second external information is a second portion of the external information and the second external information is different than the first external information;
    a light output unit for outputting light; and
    a light output controller for controlling, based on a relation between information related to a condition of a user of the other light output device included into the first external information and information related to a condition of a user of the light output device included into the second external information, a light output of the light output unit to be in one or more output states selected from among three or more output states.

2. The light output device of claim 1, wherein
    the light output unit comprises a light output tool for outputting light;
    the external information includes type information, which is information indicating an information type, and an information value, which is a value exhibited in the type information; and
    the light output controller controls the light output of the light output tool, based on a type information and an information value contained in the first external information, and a type information and an information value contained in the second external information.

3. The light output device of claim 2, further comprising a type information memory for storing type information of the external information; wherein
    the light output controller instructs the light output unit to output the light only when the type information contained in the first external information corresponds to the type information stored in the type information memory.

4. The light output device recited in claim 1, said device further comprising:
    an external information memory for storing a plurality of pieces of the external information containing the first external information and the second external information, wherein the light output controller controls the light output of the light output unit based on the plurality of pieces of the external information stored in the external information memory.

5. The light output device recited in claim 1, further comprising an external information transmitter for transmitting the second external information.

6. The light output device recited in claim 1, wherein the light output controller controls the light output to be one light intensity level among three or more light intensity levels.

7. The light output device recited in claim 1, wherein the light output controller instructs a color of the light output to be one color among three or more colors.

8. The light output device recited in claim 1, wherein the light output controller controls the intensity of light displayed across a surface of a display to be one intensity of light selected from three or more different intensities of light.

9. The light output device recited in claim 1, wherein the external information includes information indicating speed of data input at an input apparatus through which the data is input.

10. The light output device recited in claim 1, wherein the external information contains information indicating a CPU loading rate, wherein the CPU is included in the source outside of the light output device.

11. The light output device recited in claim 1, wherein the external information contains location information which is information related to the location of at least one of the light output device and a second light output device.

12. The light output device recited in claim 1, wherein the external information contains pressure information which is information related to a pressure of how strongly a second light output device is grasped by a user of the second light output device.

13. The light output device recited in claim 1, wherein the external information contains heartbeat pulse information which is information indicating pulse counts of a heartbeat of a user of a second light output device.

14. The light output device recited in claim 1, wherein the external information contains body temperature information which is information indicating a body temperature of a user of a second light output device.

15. The light output device recited in claim 1, wherein the external information contains blood sugar level information which is information indicating a blood sugar level of a user of a second light output device.

16. The light output device recited in claim 1, wherein the external information contains health condition information which is information on a health condition of a user of a second light output device.

17. The light output device recited in claim 1, wherein the external information contains PH value information which is information related to a PH value of a user of a second light output device.

18. The light output device recited in claim 1, wherein the external information contains revolution information which is information related to at least one of a revolution speed and a number of revolutions of a revolving device coupled to a second light output device.

19. The light output device recited in claim 1, wherein the external information contains brain wave information which is information related to a brain wave of a user of a second light output device.

20. The light output device recited in claim 1, wherein a shape of said light output device is one of cubic, rectangular or spherical.

21. A light output device for communicating with another light output device or a relay, the light output device comprising:

an external information acquisition unit for acquiring first external information, wherein the first external information is a first portion of external information transmitted from a source outside of the light output device;

an external information transmitter for transmitting the first external information acquired at the external information acquisition unit to the other light output device or the relay for relaying the first external information between the light output device and the other light output device;

a light output unit for outputting light;

a parameter receiver for receiving a light control parameter indicating a relation between information related to a condition of a user of the light output device included into the first external information and information related to a condition of a user of the other light output device included into a second external information, wherein the second external information is a second portion of the external information and the second external information is different than the first external information; and a light output controller for controlling, based on the light control parameter, an output of the light at the light output unit to be one or more output states selected from among three or more output states.

22. The light output device of claim 21, wherein the light output unit comprises a light output tool for outputting light;

the external information includes type information, which is information indicating an information type, and an information value, which is a value exhibited in the type information; and the light output controller controls the output of light at a plurality of the light output tools based on type information and an information value contained in the light control parameter.

23. The light output device of claim 22, further comprising a type information memory, which stores at least one of the type information contained in the external information and the type information contained in the light control parameter; wherein the light output controller instructs the light output unit to output light only when the type information contained in the light control parameter corresponds to the type information stored in the type information memory.

24. The light output device recited in claim 21, wherein the external information transmitter transmits a plurality of pieces of the external information, and the light output controller controls the light output at the light output unit based on a plurality of the light control parameters in the parameter receiver.

25. The light output device recited in claim 21, wherein the light output controller controls the light output to be one light intensity level among three or more light intensity levels.

26. The light output device recited in claim 21, wherein the light output controller instructs a color of the light output to be one color among three or more colors.

27. The light output device recited in claim 21, wherein the light output controller controls the intensity of light displayed across a surface of a display to be one intensity of light selected from three or more different intensities of light.

28. The light output device recited in claim 21, wherein the external information includes information indicating speed of data input at an input apparatus through which the data is input.

29. The light output device recited in claim 21, wherein the external information contains information indicating a CPU loading rate, wherein the CPU is included into the source outside of the light output device.

30. The light output device recited in claim 21, wherein the external information contains location information which is information related to the location of a second light output device.

31. The light output device recited in claim 21, wherein the external information contains pressure information which is information related to a pressure of how strongly a second light output device is grasped by a user of the second light output device.

32. The light output device recited in claim 21, wherein the external information contains heartbeat pulse information which is information indicating heartbeat pulse counts of a user of a second light output device.

33. The light output device recited in claim 21, wherein the external information contains body temperature information which is information indicating a body temperature of a user of a second light output device.

34. The light output device recited in claim 21, wherein the external information contains blood sugar level information which is information indicating a blood sugar level of a user of a second light output device.

35. The light output device recited in claim 21, wherein the external information contains health condition information which is information on a health condition of a user of a second light output device.

36. The light output device recited in claim 21, wherein the external information contains PH value information which is information related to a PH value of a user of a second light output device.

37. The light output device recited in claim 21, wherein the external information contains revolution information which is information related to at least one of a revolution speed and a number of revolutions of a revolving device coupled to a second light output device.

38. The light output device recited in claim 21, wherein the external information contains brain wave information which is information related to a brain wave of a user of a second light output device.

39. The light output device recited in claim 21, wherein a shape of said light output device is one of cubic, rectangular or spherical.

40. A relay for receiving external information from a source outside of the relay and transmitting the external information to a light output device via an external information receiver for receiving first external information, the first external information being a first portion of the external information, the light output device comprising:
an external information acquisition unit for acquiring second external information, wherein the second external information is a second portion of the external information and the second portion is different than the first portion;
a light output unit for outputting light; and
a light output controller for controlling, based on the first external information and the second external information, a light output of the light output unit to be in one or more output states selected from among three or more output states, the relay comprising:
an external information receiver for receiving a sender identifier, which identifies a sender of the external information, and the external information;
a transmission control information memory which stores a transmission destination identifier for identifying an external information transmission destination and transmission control information which is a counterpart of the transmission destination identifier for one or more sets;
a transmission identifier acquisition unit for acquiring, from the transmission control information memory, the transmission destination identifier which is a counterpart of the sender identifier included in the external information received at the external information receiver; and
an external information transmitter for transmitting the external information received at the external information receiver to a transmission destination identified by the transmission destination identifier acquired at the transmission destination identifier acquisition unit.

41. A relay comprising
an external information receiver for receiving a plurality of pieces of external information from a plurality of external apparatuses;
a light control parameter determination unit for determining a light control parameter based on the plurality of pieces of external information; and
a parameter transmitter for transmitting a light control parameter determined at the light control parameter determination unit to a light output device comprising:
an external information acquisition unit for acquiring external information;
an external information transmitter for transmitting the external information acquired at the external information acquisition unit;
a light output unit for outputting light;
a parameter receiver for receiving a light control parameter; and
a light output controller for controlling, based on the light control parameter, an output of the light at the light output unit to be one or more output states selected from among three or more output states.

42. A relay comprising
an external information receiver for receiving history information, which is a plurality of pieces of external information about an external apparatus, from a plurality of external apparatus;
a light control parameter determination unit for determining a light control parameter based on the history information; and
a parameter transmitter for transmitting a light control parameter determined at the light control parameter determination unit to a light output device comprising:
an external information acquisition unit for acquiring external information;
an external information transmitter for transmitting the external information acquired at the external information acquisition unit;
a light output unit for outputting light;
a parameter receiver for receiving a light control parameter; and a light output controller for controlling, based on the light control parameter, an output of the light at the light output unit to be one or more output states selected from among three or more output states, wherein the external information transmitter transmits the external information, and the light output controller controls the light output at light output unit based on the plurality of light control parameters in the parameter receiver.

43. A computer-readable medium, including a program for making a computer execute a light output device control method the light output device communicating with another light output device, said method comprising the steps of
   (a) receiving first external information, wherein the first external information is a first portion of external information transmitted from a source outside of the light output device;
   (b) acquiring a second external information, wherein the second external information is a second portion of the external information and the second external information is different than the first external information; and
   (c) controlling a light output of the light output device based on a relation between information related to a condition of a user of the other light output device included into the first external information and information related to a condition of a user of the light output device included into the second external information.

44. The computer-readable medium of claim 43, wherein the external information includes type information which is information indicating a type of information, and an information value which is a value exhibited in the type information; and light output is controlled at step (c) based on type information and value information contained in the first external information, and type information and information value contained in the second external information.

45. The computer-readable medium of claim 44, which method further comprising the step of
   (d) storing type information of the external information; wherein
   at step (c), a light output controller is instructed to output the light only when the type information contained in the first external information corresponds to the stored type information.

46. The computer-readable medium of claim 45, wherein
   at step (c), the light output controller controls the light to be outputted based on a plurality of light output parameters;
   at step (d), a light output parameter identifier for identifying the plurality of light output parameters and type information are stored under a counterpart relationship; and
   at step (d), the computer is instructed to output the light in accordance with a light output parameter identified by the light output parameter identifier only when the type information contained in the first external information corresponds to the stored type information.

47. The computer-readable medium recited in claim 43, which method further comprising the step of
   (e) recording a plurality of pieces of the external information containing the first external information and the second external information; wherein
   at step (c), the light output is controlled based on the plurality of pieces of the external information.

48. The computer-readable medium recited in claim 43, which method further comprising the step of
   (f) transmitting the external information.

49. A computer-readable medium, including a program for making a computer execute a method of controlling a light output device, the light output device communicating with another light output device or relay, said method comprising the steps of
   (a) acquiring first external information, wherein the first external information is a first portion of external information transmitted from a source outside of the light output device;
   (b) transmitting the first external information to the other light output device or relay for relaying the first external information between the light output device and the other light output device;
   (c) receiving a light control parameter indicating a relation between information related to a condition of a user of the light output device included into the first external information and information related to a condition of a user of the other light output device included into a second external information, wherein the second external information is a second portion of the external information and the second external information is different than the first external information; and
   (d) controlling, based on the light control parameter, the output of light to be in one or more output states selected from among three or more output states.

50. The computer-readable medium of claim 49, wherein
   the external information includes type information which is information indicating an information type, and an information value which represents a value exhibited in the type information; and
   at step (d), the light output is controlled based on type information and information value contained in the light control parameter.

51. The computer-readable medium of claim 50, which method further comprising the step of
   (e) storing at least one of type information contained in the external information and type information of the light control parameter, wherein
   at step (d), light output is controlled only when type information contained in the light control parameter corresponds to the stored type information.

52. The computer-readable medium of claim 51, wherein
   at step (c), a plurality of light output methods are controlled;
   at step (e), a light output method identifier for identifying the plurality of light output methods and the stored type information are stored under a counterpart relationship; and
   at step (d), the light output is controlled in accordance with a light output method identified by the light output method identifier, only when type information contained in the light control parameter corresponds to the stored type information.

53. The computer-readable medium recited in claim 49, wherein
   step (b), further includes transmitting a plurality of pieces of the external information; and
   at step (d), the light output is controlled in accordance with a plurality of the light control parameters.

* * * * *